(12) United States Patent
Addison et al.

(10) Patent No.: US 11,419,558 B2
(45) Date of Patent: Aug. 23, 2022

(54) DETERMINING A LIMIT OF AUTOREGULATION

(71) Applicant: Covidien LP, Mansfield, MA (US)

(72) Inventors: Paul S. Addison, Edinburgh (GB); Dean Montgomery, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 773 days.

(21) Appl. No.: 15/980,235

(22) Filed: May 15, 2018

(65) Prior Publication Data

US 2018/0338731 A1 Nov. 29, 2018

Related U.S. Application Data

(60) Provisional application No. 62/510,303, filed on May 24, 2017.

(51) Int. Cl.
*A61B 5/00* (2006.01)
*A61B 5/021* (2006.01)
(Continued)

(52) U.S. Cl.
CPC .......... *A61B 5/7246* (2013.01); *A61B 5/0205* (2013.01); *A61B 5/02125* (2013.01);
(Continued)

(58) Field of Classification Search
None
See application file for complete search history.

(56) References Cited

U.S. PATENT DOCUMENTS

| 4,688,577 A | 8/1987 | Bro |
| 5,579,774 A | 12/1996 | Miller et al. |

(Continued)

FOREIGN PATENT DOCUMENTS

| CN | 100399990 A | 12/2006 |
| DE | 10331027 A1 | 1/2005 |

(Continued)

OTHER PUBLICATIONS

Chuan et al., "Is cerebrovascular autoregulation associated with outcomes after major noncardiac surgery? A prospective observational pilot study," Acta Anaesthesiol Scand., Aug. 5, 2018, 10 pp.
(Continued)

*Primary Examiner* — Jay B Shah
(74) *Attorney, Agent, or Firm* — Shumaker & Sieffert, P.A.

(57) ABSTRACT

In some examples, a device includes processing circuitry configured to receive first and second signals indicative of first and second physiological parameters and determine a trendline function based on values of first and second physiological parameters. The processing circuitry is further configured to determine transformed values of the first physiological parameter based on the trendline function. The processing circuitry is configured to determine correlation coefficient values for the transformed values of the first physiological parameter and the values of the second physiological parameter. The processing circuitry is further configured to determine a limit of autoregulation of the patient based on the correlation coefficient values. The processing circuitry is configured to determine an autoregulation status based on the estimate of the limit of autoregulation and output, for display, an indication of the autoregulation status.

15 Claims, 24 Drawing Sheets

(51) Int. Cl.
   G16H 50/20      (2018.01)
   A61B 5/0205    (2006.01)
   A61B 5/022     (2006.01)
   A61B 5/1455    (2006.01)
(52) U.S. Cl.
   CPC .......... *A61B 5/4064* (2013.01); *A61B 5/7239* (2013.01); *A61B 5/7275* (2013.01); *A61B 5/7425* (2013.01); *G16H 50/20* (2018.01); *A61B 5/021* (2013.01); *A61B 5/02225* (2013.01); *A61B 5/14553* (2013.01)

(56) References Cited

U.S. PATENT DOCUMENTS

| | | | |
|---|---|---|---|
| 6,438,399 | B1 | 8/2002 | Kurth |
| 6,599,251 | B2 | 7/2003 | Chen et al. |
| 6,875,176 | B2 | 4/2005 | Mourad et al. |
| 7,532,919 | B2 | 5/2009 | Soyemi et al. |
| 7,744,541 | B2 | 6/2010 | Baruch et al. |
| 7,998,075 | B2 | 8/2011 | Ragauskas et al. |
| 8,057,398 | B2 | 11/2011 | Mcnames et al. |
| 8,062,224 | B2 | 11/2011 | Ragauskas et al. |
| 8,211,022 | B2 | 7/2012 | Lo et al. |
| 8,366,627 | B2 | 2/2013 | Kashif et al. |
| 8,433,384 | B2 | 4/2013 | Bechtel et al. |
| 8,512,260 | B2 | 8/2013 | Grudic et al. |
| 8,556,811 | B2 | 10/2013 | Brady |
| 8,852,094 | B2 | 10/2014 | Al-ali et al. |
| 9,192,330 | B2 | 11/2015 | Lin et al. |
| 9,861,317 | B2 | 1/2018 | Ochs |
| 2002/0099295 | A1 | 7/2002 | Gil et al. |
| 2003/0219797 | A1 | 11/2003 | Zhao et al. |
| 2009/0326386 | A1 | 12/2009 | Sethi et al. |
| 2010/0010322 | A1* | 1/2010 | Brady ................... A61B 5/021 600/301 |
| 2010/0030054 | A1 | 2/2010 | Baruch et al. |
| 2011/0105912 | A1 | 5/2011 | Widman et al. |
| 2012/0004517 | A1 | 1/2012 | Starr et al. |
| 2012/0253211 | A1 | 10/2012 | Brady et al. |
| 2013/0144140 | A1 | 6/2013 | Frederick et al. |
| 2013/0190632 | A1 | 7/2013 | Baruch et al. |
| 2014/0073888 | A1 | 3/2014 | Kim |
| 2014/0278285 | A1 | 9/2014 | Marmarelis et al. |
| 2015/0230758 | A1 | 8/2015 | Ochs |
| 2016/0081563 | A1 | 3/2016 | Wiard et al. |
| 2016/0106372 | A1 | 4/2016 | Addison et al. |
| 2016/0162786 | A1 | 6/2016 | Grudic et al. |
| 2016/0220115 | A1 | 8/2016 | Fisher et al. |
| 2016/0324425 | A1 | 11/2016 | Addison et al. |
| 2016/0367197 | A1 | 12/2016 | Addison et al. |
| 2017/0105631 | A1 | 4/2017 | Addison et al. |
| 2018/0014791 | A1 | 1/2018 | Montgomery et al. |

FOREIGN PATENT DOCUMENTS

| | | | |
|---|---|---|---|
| RU | | 2465829 C1 | 11/2012 |
| WO | WO 2016015057 A1 | | 1/2016 |

OTHER PUBLICATIONS

International Preliminary Report on Patentability from International Application No. PCT/US2018/032749, dated Dec. 5, 2019, 12 pp.
Invitation to Pay Additional Fees from International Application No. PCT/US2018/032749, dated Aug. 3, 2018, 15 pp.
International Search Report and Written Opinion from International Application No. PCT/US2018/032749, dated Sep. 27, 2018, 20 pp.
Ameloot et al., "An observational near-infrared spectroscopy study on cerebral autoregulation in post-cardiac arrest patients: Time to drop 'one-size-fits-all' hemodynamic targets?," Resuscitation 90, 121-126, Jan. 2015.
Brady, MD, et al., "Monitoring Cerebrovascular Autoregulation Refining care goals in the ICU," Apr. 21, 2009, 15 pp.
Brady, MD et al., "Real-time continuous monitoring of cerebral blood flow autoregulation using near-infrared spectroscopy in patients undergoing cardiopulmonary bypass," Stroke 41, pp. 1951-1956, Feb. 2010.
Brady, MD et al., "A Dynamic Association Between Cavopulmonary Shunt Pressure and Cerebrovascular Autoregulation in an Infant With Congenital Heart Disease and Intracranial Hemorrhage," J. Cardiothorac. Vase. Anesth. Vo. 23, No. 2, pp. 215-218; Apr. 2009.
Brady, MD et al., "Continuous Measurement of Autoregulation by Spontaneous Fluctuations in Cerebral Perfusion Pressure: Comparison of 3 Methods," Stroke. 39, pp. 2531-2537; Sep. 2008.
Brady, MD et al., "Continuous Monitoring of Cerebrovascular Pressure Reactivity After Traumatic Brain Injury in Children," Pediatrics 124, e1205-e1212, Dec. 2009.
Brady, MD et al., "Continuous Time-Domain Analysis of Cerebrovascular Autoregulation Using Near-infrared Spectroscopy," Stroke 38, pp. 2818-2825; Oct. 2007.
Brady, MD et al., "Monitoring Cerebral Blood Flow Pressure Autoregulation in Pediatric Patients During Cardiac Surgery," Stroke 41, 1957-1962, Sep. 2010.
Brady, MD et al., "Noninvasive Autoregulation Monitoring With and Without Intracranial Pressure in the Naïve Piglet Brain," Anesth. Analg. vol. 111, No. 1, 191-195; Jul. 2010.
Budohoski, MD et al., "Bilateral Failure of Cerebral Autoregulation is Related to Unfavorable Outcome After Subarachnoid Hemorrhage," Neurocrit. Care 22, 65-73, Jul. 2014.
Budohoski, MD, et al., "The Relationship Between Cerebral Blood Flow Autoregulation and Cerebrovascular Pressure Reactivity After Traumatic Brain Injury," Neurosurgery 71, pp. 652-660 May 2012.
Calviere et al., "Prediction of Delayed Cerebral Ischemia After Subarachnoid Hemorrhage Using Cerebral Blood Flow Velocities and Cerebral Autoregulation Assessment," Neurocrit. Care, Feb. 2015.
Czosnyka, PhD, et al., "Intracranial pressure: More Than a Number," Neurosurg. Focus 22, E10, May 2007.
Czosnyka, PhD, et al., "Monitoring of Cerebrovascular Autoregulation: Facts, myths, and missing links," Neurocrit. Care 10, 373-386, Jan. 2009.
Czosnyka, PhD, et al., "Monitoring of Cerebral Autoregulation in Head-Injured Patients," Stroke. 27, 1829-1834, Oct. 1996.
Depreitere et al., "Pressure autoregulation monitoring and cerebral perfusion pressure target recommendation in patients with severe traumatic brain injury based on minute-by-minute monitoring data," J. Neurosurg. 120, pp. 1451-1457, Apr. 2014.
Dias et al., "Kidney-Brain Link in Traumatic Brain Injury Patients? A preliminary report," Neurocrit. Care, Oct. 2014, 12 pp.
Dias et al., "Optimal Cerebral Perfusion Pressure Management at Bedside: A Single-Center Pilot Study," Neurocrit. Care, Jan. 2015, 13 pp.
Diedler, MD et al., "The Limitations of Near-Infrared Spectroscopy to Assess CerebrovascularR: The Role of Slow Frequency Oscillations," Anesth. Analg. vol. 113 No. 4, pp. 849-857, Oct. 2011.
Donnelly et al., "Further understanding of cerebral autoregulation at the bedside: possible implications for future therapy," Expert Rev. Neurother. 15, pp. 169-185, Jan. 2015.
Eide, MD, PhD., et al. "Pressure-derived versus pressure wave amplitude-derived indices of cerebrovascular pressure reactivity in relation to early clinical state and 12-month outcome following aneurysmal subarachnoid hemorrhage," J. Neurosurg. 116, pp. 961-971, May 2012.
Gilmore et al., "Relationship between cerebrovascular dysautoregulation and arterial blood pressure in the premature infant," J. Perinatol. 31, pp. 722-729, Mar. 2011.
Hori et al., "Effect of carotid revascularization on cerebral autoregulation in combined cardiac surgery," Eur. J. Cardio-Thoracic Surg., Feb. 2015, 7 pp.
Howells et al., "An optimal frequency range for assessing the pressure reactivity index in patients with traumatic brain injury," J. Clin. Monit. Comput., pp. 97-105, Mar. 2014.
Howlett et al., "Cerebrovascular autoregulation and neurologic injury in neonatal hypoxic-ischemic encephalopathy," Pediatr. Res. vol. 74, No. 5, pp. 525-535, Nov. 2013.

(56) References Cited

OTHER PUBLICATIONS

Jaeger, MD et al., "Effects of cerebrovascular pressure reactivity-guided optimization of cerebral perfusion pressure on brain tissue oxygenation after traumatic brain injury," Crit. Care Med. vol. 38, No. 5, pp. 1343-1347, May 2010.

Jaeger, MD, et al., "Continuous monitoring of cerebrovascular autoregulation after subarachnoid hemorrhage by brain tissue oxygen pressure reactivity and its relation to delayed cerebral infarction," Stroke 38, pp. 981-986, Apr.-May 2007.

Kvandal et al., "Impaired cerebrovascular reactivity after acute traumatic brain injury can be detected by wavelet phase coherence analysis of the intracranial and arterial blood pressure signals," J. Clin. Monit. Comput. 27, pp. 375-383, May 2013.

Laflam et al., "Shoulder Surgery in the Beach Chair Position Is Associated with Diminished Cerebral Autoregulation but No. Differences in Postoperative Cognition or Brain Injury Biomarker Levels Compared with Supine Positioning," Anesth. Analg. vol. 120, No. 1, pp. 176-185, Jan. 2015.

Lang MD, PhD, et al., "A Review of Cerebral Autoregulation: Assessment and Measurements," Aust. Anaesth. 161-172, 2005, (Applicant points out, in accordance with MPEP 609.04(a), that the year of publication, 2005, is sufficiently earlier than the effective U.S. filing date, Mar. 5, 2018, so that the particular month of publication is not in issue.).

Lang et al., "Short pressure reactivity index versus long pressure reactivity index in the management of traumatic brain injury," J. Neurosurg. vol. 122, pp. 588-594, Mar. 2015.

Lang et al., "Continuous monitoring of cerebrovascular autoregulation: a validation study," J. Neurol. Neurosurg. Psychiatry 72, pp. 583-586, Jan. 2002.

Lee et al., "A pilot study of cerebrovascular reactivity autoregulation after pediatric cardiac arrest," Resuscitation 85, pp. 1387-1393, Jun. 2014.

Lee, J. K. et al., "Cerebral blood flow and cerebrovascular autoregulation in a swine model of pediatric cardiac arrest and hypothermia*," Crit. Care Med. vol. 39, No. 10, pp. 2337-2345, Oct. 2011.

Lee, MD et al., "Cerebrovascular Reactivity Measured by Near-Infrared Spectroscopy," Stroke 40, pp. 1820-1826, Oct. 2009.

Lee, MD, et al., "Noninvasive autoregulation monitoring in a swine model of pediatric cardiac arrest," Anesth. Analg. vol. 114, pp. 825-836, Apr. 2012.

Lewis et al., "Continuous Correlation Between Intracranial Pressure and Cerebral Blood Flow Velocity Reflects Cerebral Autoregulation Impairment During Intracranial Pressure Plateau Waves," Neurocrit. Care 21, pp. 514-525, May 2014.

Liu et al., "Comparison of frequency and time domain methods of assessment of cerebral autoregulation in traumatic brain injury," J. Cereb. Blood Flow Metab. 35, pp. 248-256, Nov. 2014.

Nasr et al., "Baroreflex and Cerebral Autoregulation Are Inversely Correlated," Circ. J. vol. 78, pp. 2460-2467, Oct. 2014.

Nasr et al., "Cerebral autoregulation in patients with obstructive sleep apnea syndrome during wakefulness," Eur. J. Neurol. 16, pp. 386-391, Mar. 2009.

Ono, MD et al., "Blood pressure excursions below the cerebral autoregulation threshold during cardiac surgery are associated with acute kidney injury," Crit. Care Med. 41, pp. 464-471, Feb. 2013.

Ono, MD et al., "Cerebral Blood Flow Autoregulation Is Preserved After Hypothermic Circulatory Arrest," Ann. Thorac. Surg. 96, pp. 2045-2053, Dec. 2013.

Ono, MD et al., "Duration and magnitude of blood pressure below cerebral autoregulation threshold during cardiopulmonary bypass is associated with major morbidity and operative mortality," J. Thorac. Cardiovasc. Surg. 147, p. 483-489, Jan. 2014.

Ono, MD et al., "Risks for impaired cerebral autoregulation during cardiopulmonary bypass and postoperative stroke," Br. J. Anaesth. 109, pp. 391-398, Jun. 2012.

Ono, MD et al., "Validation of a Stand-Alone Near-Infrared Spectroscopy System for Monitoring Cerebral Autoregulation During Cardiac Surgery," Anesth. Analg. vol. 116, No. 1, pp. 198-204, Jan. 2013.

Papademetriou et al., "Multichannel near infrared spectroscopy indicates regional variations in cerebral autoregulation in infants supported on extracorporeal membrane oxygenation," J. Biomed. Opt., vol. 17, p. 067008-1-067008-9, Jun. 2012.

Radolovich et al., "Pulsatile Intracranial Pressure and Cerebral Autoregulation After Traumatic Brain Injury," Neurocrit. Care 15, pp. 379-386, Dec. 2011.

Radolovich et al., "Reactivity of Brain Tissue Oxygen to Change in Cerebral Perfusion Pressure in Head Injured Patients, " Neurocrit. Care 10, pp. 274-279, Feb. 2009.

Reinhard, MD et al., "Cerebral Autoregulation in Carotid Artery Occlusive Disease Assessed From Spontaneous Blood Pressure Fluctuations by the Correlation Coefficient Index," Stroke 34, pp. 2138-2144, May 2003.

Reinhard, MD et al., "Cerebral dysautoregulation and the risk of ischemic events in occlusive carotid artery disease," J. Neurol. 255, pp. 1182-1189, Jun. 2008.

Schmidt et al., "Impaired autoregulation is associated with mortality in severe cerebral diseases" Clinical Neurosciences and Mental Health, 1 (Suppl. 1), May 2014, 6 pp.

Schmidt et al., "Asymmetry of cerebral autoregulation does not correspond to asymmetry of cerebrovascular pressure reactivity," Perspect. Med. 1-12, pp. 285-289, Sep. 2012.

Schmidt et al., "Cerebral Autoregulatory Response Depends on the Direction of Change in Perfusion Pressure," J. Neurotrauma 26, pp. 651-656, May 2009.

Severdija et al., "Assessment of dynamic cerebral autoregulation and cerebral carbon dioxide reactivity during normothermic cardiopulmonary bypass," Med. Biol. Eng. Comput. 53, pp. 195-203, Nov. 2014.

Smith, "Shedding light on the adult brain: a review of the clinical applications of near-infrared spectroscopy," Philos. Trans. R. Soc. A Math. Phys. Eng. Sci. 369, pp. 4452-4469 Oct. 2011.

Soul et al., "Fluctuating Pressure-Passivity Is Common in the Cerebral Circulation of Sick Premature Infants," Pediatric Research 61, No. 4, Nov. 2007, pp. 467-473.

Steiner, MD et al., "Continuous monitoring of cerebrovascular pressure reactivity allows determination of optimal cerebral perfusion pressure in patients with traumatic brain injury," Crit. Care Med. 30, pp. 733-738, Apr. 2002.

Steiner et al., "Near-Infrared Spectroscopy Can Monitor Dynamic Cerebral Autoregulation in Adults," Neurocrit. Care 10, pp. 122-128, Sep. 2008.

Tekes et al., "Apparent Diffusion Coefficient Scalars Correlate with Near-Infrared Spectroscopy Markers of Cerebrovascular Autoregulation in Neonates Cooled for Perinatal Hypoxic-Ischemic Injury," Am. J. Neuroradiol. 36, pp. 188-193, Jan. 2015.

Zheng et al., "Continuous Cerebral Blood Flow Autoregulation Monitoring in Patients Undergoing Liver Transplantation," Neurocrit. Care 17, pp. 77-84, Aug. 2012.

Zweifel et al., "Continuous Assessment of Cerebral Autoregulation With Near-Infrared Spectroscopy in Adults After Subarachnoid Hemorrhage," Stroke 41, pp. 1963-1968, Jan. 2010.

Zweifel et al., "Continuous time-domain monitoring of cerebral autoregulation in neurocritical care," Med. Eng. Phys. 36, 638-645, Feb. 2014.

Tsalach et al., "Cerebral Autoregulation Real-Time Monitoring," PLOS One, Aug. 29, 2016, 14 pp.

Chung MD, PhD et al., "Assessment of Noninvasive Regional Brain Oximetry in Posterior Reversible Encephalopahty Syndrome and Reversible Cerebral Vasoconstriction Syndrome," Journal of Intensive Care Medicine, vol. 31(6), Jan. 2016, pp. 415-419.

Lee et al., "Cerebrovascular Autoregulation in pediatric moyamoya Disease" Pediatric Anesthesia, 23, pp. 547-556, Jun. 2013.

Steppan, MD, et al., "Cerebral and Tissue Oximetryc" Best Pract Res Clin Anaesthesiol, Dec. 2014, pp. 429-439.

Brady et al., "A New Monitor of Pressure Autoregulation: What Does It Add?" International Anesthesia Research Society, Nov. 2015, vol. 121, No. 5, pp. 1121-1123.

Prabhakar et al., "Current concepts of optimal cerebral perfusion pressure in traumatic brain injury," J, Anaesthesiol Clin Pharmacol, Jul.-Sep. 2014, pp. 318-327.

(56) References Cited

OTHER PUBLICATIONS

Lang et al., "Continuous monitoring of cerebrovascular autoregulation: a validation study," J Neurol Neurosurg Psychiatry, pp. 583-586, Jan. 2002.
Lazaridis et al., Optimal cerebral perfusion pressure: are we ready for it? Neurological Research, vol. 35, No. 2, Nov. 12, 2013, pp. 138-148.
Joshi et al., "Predicting the Limits of Cerebral Autoregulation During Cardiopulmonary Bypass," Anesthesia-Analgesia, Mar. 2012, vol. 114, No. 3, pp. 503-510.
Olsen et al., "Validation of Transcranial Near-Infrared Spectroscopy for Evaluation of Cerebral Blood Flow Autoregulation," Journal of Neurosurgical Anesthesiology, pp. 280-285, Oct. 1996.
Addison et al., "Gradient adjustment method for better discriminating correlating and noncorrelating regions of physiological signals: application to the partitioning of impaired and intact zones of cerebral autoregulation," J Clin Moit Comput, Aug. 2016, 11 pp.
Montgomery et al., "Data clustering methods for the determination of cerebral autoregulation functionality," J Clin Monit Comput, Sep. 2015, 8 pp.
Brady et al., "The Lower Limit of Cerebral Blood Flow Autoregulation is Increased with Elevated Intracranial Pressure," vol. 108, No. 4, Apr. 2009.
Gao et al., "Mathematical considerations for modeling cerebral blood flow autoregulation to systemic arterial pressure," accessed on Sep. 19, 2016, accessed from http://ajpheart.physiology.org/., pp. H1023-H1031.
Hauerberg et al., "The Upper Limit of Cerebral Blood Flow Autoregulation in Acute Intracranial Hypertension," Journal of Neurosurgical Anesthesiology, vol. 10, No. 2, pp. 106-112, May 1998.
Hori et al., "Arterial pressure above the upper cerebral autoregulation limit during cardiopulmonary bypass is associated with post-operative delirium," British Journal of Anaesthesia Sep. 2014, pp. 1009-1017.
Kamar et al., "Detecting Cerebral Autoregulation Thresholds Using a Noninvasive Cerebral Flow Monitor," Ornim medical, May 2013, Portugal Poster, 1 pp.
Lucas et al., "Influence of Changes in Blood Pressure on cerebral Perfusion and Oxygenation," Hypertension, Oct. 2009, pp. 698-705.
Minassian et al., "Changes in intracranial pressure and cerebral autoregulation in patients with severe traumatic brain injury," vol. 30, Jul. 2002, pp. 1616-1622.
Pesek, MD, et al., "The upper limit of cerebral blood flow autoregulation is decreased with elevations in intracranial pressure," Neurosurgery, vol. 75, No. 2, Aug. 2014, pp. 163-170.
Sadoshima et al., "Upper Limit of Cerebral Autoregulation During Development of Hypertension in Spontaneously Hypertensive Rats—Effect of Sympathetic Denervation," vol. 16, No. 3, May-Jun. 1985, pp. 477-481.
Sadoshima et al., "Inhibition of Angiotensin—Converting Enzyme Modulates the Autoregulation of Regional Cerebral Blood Flow in Hypertensive Rats," vol. 23, No. 6, Part 1, Jun. 1994, pp. 781-785.
Strandgaard et al., "Upper Limit of Cerebral Blood Flow Autoregulation in Experimental Renovascular Hypertension in the Baboon," vol. 37, Aug. 1975, pp. 164-167.
Ragauskas et al., "Analysis of cerebrovascular autoregulation reactivity index electronic monitoring methods," vol. 114, No. 8, Jun. 2011, 6 pp.
Chiu et al., "Assessment of cerebral autoregulation using time-domain cross-correlation analysis," Computers Bio Med, Nov. 2001, pp. 471-480.
Larson et al., "Cerebrovascular autoregulation after rewarming from hypothermia in a neonatal swine model of asphyxic brain injury," J Appl Physiol. 115; pp. 1433-1442, Sep. 2013.
Petkus et al., "Novel Method and Device for Fully Non-Invasive Cerebrovascular Autoregulation Monitoring," Elektronika Ir Elektrotechnika, vol. 20, No. 8, pp. 24-29, Oct. 2014.
Olufsen et al., "Blood pressure and blood flow variation during postural change from sitting to standing: model development and validation," J Appl Physiol Oct. 2005, pp. 1523-1537.
Rangel-Castilla, MD, et al., "Cerebral pressure autoregulation in traumatic brain injury," Neurosurg Focus, vol. 25, Oct. 2008, 8 pp.
Addison, "A Review of Wavelet Transform Time-Frequency Methods for NIRS-Based Analysis of Cerebral Autoregulation," IEEE Reviews in Biomedical Engineering, vol. 8, 2015, pp. 78-85.
Moerman, M.D., Ph.D., et al., "Assessment of Cerebral Autoregulation Patterns with Near-infrared Spectroscopy during Pharmacological-induced Pressure Changes," Anesthesiology, vol. 123, No. 2, Aug. 2015, pp. 327-335.
U.S. Appl. No. 15/911,449, naming Paul S. Addison et al. as inventors, filed Mar. 5, 2018.
U.S. Appl. No. 15/962,438, naming Paul S. Addison et al. as inventors, filed Apr. 25, 2018.
U.S. Appl. No. 15/962,503, naming Paul S. Addison et al. as inventors, filed Apr. 25, 2018.
U.S. Appl. No. 15/962,468, naming Paul S. Addison et al. as inventors, filed Apr. 25, 2018.
U.S. Appl. No. 15/962,486, naming Dean Montgomery et al. as inventors, filed Apr. 25, 2018.

* cited by examiner

BP

TIME (SECONDS)

BP

TIME (SECONDS)

DETERMINING A LIMIT OF AUTOREGULATION

This application claims the benefit of U.S. Provisional Application No. 62/510,303, filed May 24, 2017, the entire content of which is incorporated by reference.

TECHNICAL FIELD

This disclosure relates to autoregulation of blood pressure, particularly cerebral autoregulation.

BACKGROUND

Cerebral autoregulation (CA) is the response mechanism by which an organism regulates cerebral blood flow over a wide range of systemic blood pressure changes through complex myogenic, neurogenic, and metabolic mechanisms. Autoregulation dysfunction may result from a number of causes including, stroke, traumatic brain injury, brain lesions, brain asphyxia, or infections of the central nervous system. Intact cerebral autoregulation function occurs over a range of blood pressures defined between a lower limit of autoregulation (LLA) and an upper limit of autoregulation (ULA). Thus the intact autoregulation zone may differ from patient to patient.

The Pearson coefficient, or cerebral oximetry index (COx), is derived from the correlation between cerebral oxygen saturation in the blood ($rSO_2$) and mean arterial pressure (MAP). COx relates to the regression line fit between $rSO_2$ and MAP over a time window, which may last three hundred seconds, in some examples. The COx method may be used to produce a picture of a patient's blood-pressure-dependent autoregulation status.

SUMMARY

This disclosure describes techniques for determining a limit of autoregulation (LA) such as the lower limit of autoregulation (LLA) and/or the upper limit of autoregulation (ULA) based on mean arterial pressure (MAP) and regional oxygen saturation ($rSO_2$). In some examples, the method may include transforming the values of $rSO_2$ by determining a gradient or trendline of the MAP-$rSO_2$ curve and applying the trendline values to the values of $rSO_2$. The method may further include determining one or more values of a cerebral oximetry index (COx) that measures the correlation between the MAP and the transformed values of $rSO_2$. Alternatively or additionally, the method may include determining COx values from the values of MAP and the untransformed values of $rSO_2$. The method may also include transforming the values of COx using a piecewise function or a continuous function.

Clause 1: In some examples, a device includes a display and processing circuitry configured to receive a first signal indicative of a first physiological parameter of a patient and a second signal indicative of a second physiological parameter of the patient. The processing circuitry is also configured to determine a trendline function based on values of the first physiological parameter and values of the second physiological parameter. The processing circuitry is further configured to determine transformed values of the first physiological parameter based on the trendline function. The processing circuitry is configured to determine correlation coefficient values for the transformed values of the first physiological parameter and the values of the second physiological parameter. The processing circuitry is also configured to determine a limit of autoregulation of the patient based on the correlation coefficient values and determine an autoregulation status of the patient based on the limit of autoregulation. The processing circuitry is further configured to output, for display via the display, an indication of the autoregulation status.

Clause 2: In some examples of clause 1, the processing circuitry is configured to determine the limit of autoregulation at least in part by determining a lower limit of autoregulation based on the correlation coefficient values.

Clause 3: In some examples of clause 1 or clause 2, the processing circuitry is configured to determine the limit of autoregulation at least in part by determining an upper limit of autoregulation based on the correlation coefficient values.

Clause 4: In some examples of any of clauses 1-3, the first physiological parameter includes an oxygen saturation of the patient and the second physiological parameter includes a blood pressure of the patient. The processing circuitry is configured to determine the trendline function at least in part by determining the trendline function based on the measurements of oxygen saturation in the blood of the patient and the blood pressure of the patient. The processing circuitry is configured to determine the transformed values of the first physiological parameter at least in part by determining transformed values of oxygen saturation in the blood of the patient. The processing circuitry is configured to determine the correlation coefficients at least in part by determining correlation coefficients for the transformed values of oxygen saturation in the blood of the patient and the blood pressure of the patient.

Clause 5: In some examples of any of clauses 1-4, the processing circuitry is configured to determine the trendline function at least in part by determining a best fit for the values of the first physiological parameter and the values of the second physiological parameter.

Clause 6: In some examples of any of clauses 1-5, the processing circuitry is configured to determine the transformed values of the first physiological parameter at least in part by determining transformed values of the first physiological parameter based a difference between each value of the first physiological parameter and a respective expected trendline value of the first physiological parameter.

Clause 7: In some examples of any of clauses 1-6, the processing circuitry is configured to determine the correlation coefficient values at least in part by binning each transformed value of the first physiological parameter based on a respective value of the second physiological parameter and determining an average correlation coefficient for each bin of a plurality of bins.

Clause 8: In some examples of any of clauses 1-7, the processing circuitry is further configured to determine an initial trendline function based on historical data, and the processing circuitry is configured to determine the trendline function at least in part by reducing an effect of the initial trendline function as the processing circuitry determines values of the first physiological parameter.

Clause 9: In some examples of any of clauses 1-8, the processing circuitry is further configured to determine that a total number of data points exceeds a threshold number, and the processing circuitry is configured to determine the trendline function and determine the transformed values of the first physiological parameter in response to determining that the total number of data points exceeds the threshold number.

Clause 10: In some examples, a device includes a display and processing circuitry configured to receive a first signal indicative of a first physiological parameter of a patient and a second signal indicative of a second physiological parameter of the patient. The processing circuitry is also configured to determine untransformed correlation coefficient values for values of the first physiological parameter and values of the second physiological parameter. The processing circuitry is further configured to determine transformed correlation coefficient values based on the untransformed correlation coefficient values. The processing circuitry is configured to determine a limit of autoregulation of the patient based on the transformed correlation coefficient values and determine an autoregulation status of the patient based on the limit of autoregulation. The processing circuitry is further configured to output, for display via the display, an indication of the autoregulation status.

Clause 11: In some examples of clause 10, the processing circuitry is configured to determine the transformed correlation coefficient values at least in part by applying a transform function to the untransformed correlation coefficient values.

Clause 12: In some examples of clause 11, the processing circuitry is configured to apply the transform function at least in part by determining that a first untransformed correlation coefficient value exceeds a threshold value and determining a transformed correlation coefficient value equal to a predetermined value in response to determining that the untransformed correlation coefficient value exceeds the threshold value.

Clause 13: In some examples of clause 11 or clause 12, the processing circuitry is configured to apply the transform function at least in part by determining that a second untransformed correlation coefficient value is less than a threshold value and applying a linear function to the second untransformed correlation coefficient value to determine a second transformed correlation coefficient value in response to determining that the second untransformed correlation coefficient value is less than the threshold value.

Clause 14: In some examples of any of clauses 10-13, the processing circuitry is further configured to determine that a total number of data points exceeds a threshold number. The processing circuitry is configured to determine the transformed correlation coefficient values in response to determining that the total number of data points exceeds the threshold number.

Clause 15: In some examples, a method includes receiving, by processing circuitry of a device and from sensing circuitry, a first signal indicative of a first physiological parameter of a patient and a second signal indicative of a second physiological parameter of the patient. The method further includes determining, by the processing circuitry, a trendline function based on values of the first physiological parameter and values of the second physiological parameter. The method includes determining, by the processing circuitry, transformed values of the first physiological parameter based on the trendline function. The method also includes determining, by the processing circuitry, correlation coefficient values for the transformed values of the first physiological parameter and the values of the second physiological parameter. The method further includes determining, by the processing circuitry, a limit of autoregulation based on the correlation coefficient values.

Clause 16: In some examples of clause 15, receiving the first signal comprises receiving an oxygen saturation signal of the patient, and receiving the second signal comprises receiving a blood pressure signal of the patient. Determining the trendline function comprises determining the trendline function based on the measurements of oxygen saturation in the blood of the patient and the blood pressure of the patient. Determining the transformed values of the first physiological parameter comprises determining transformed values of oxygen saturation in the blood of the patient. Determining the correlation coefficient values comprises determining correlation coefficient values for the transformed values of oxygen saturation in the blood of the patient and the blood pressure of the patient.

Clause 17: In some examples of clause 15 or clause 16, determining the trendline function includes determining a best fit for the values of the first physiological parameter and the values of the second physiological parameter.

Clause 18: In some examples of any of clauses 15-17, determining the transformed values of the first physiological parameter includes determining transformed values of the first physiological parameter based a difference between each value of the first physiological parameter and a respective expected trendline value of the first physiological parameter.

Clause 19: In some examples of any of clauses 15-18, the method also includes determining an initial trendline function based on historical data. Determining the trendline function comprises reducing an effect of the initial trendline function while determining values of the first physiological parameter.

Clause 20: In some examples of any of clauses 15-19, the method also includes determining that a total number of data points exceeds a threshold number. Determining the trendline function and determining the transformed values of the first physiological parameter are in response to determining that the total number of data points exceeds the threshold number.

Clause 21: In some examples, a method includes receiving, by processing circuitry of a device and from sensing circuitry, a first signal indicative of a first physiological parameter of a patient and a second signal indicative of a second physiological parameter of the patient. The method further includes determining, by the processing circuitry, untransformed correlation coefficient values for values of the first physiological parameter and values of the second physiological parameter. The method also includes determining transformed correlation coefficient values based on the untransformed correlation coefficient values. The method includes determining a limit of autoregulation based on the transformed correlation coefficient values and determining an autoregulation status of the patient based on the limit of autoregulation. The method further includes determining, by the processing circuitry, a limit of autoregulation based on the correlation coefficient values.

Clause 22: In some examples of clause 21, determining the transformed correlation coefficient values comprises applying a transform function to the untransformed correlation coefficient values.

Clause 23: In some examples of clause 22, applying the transform function comprises determining that a first untransformed correlation coefficient value exceeds a threshold value and determining a transformed correlation coefficient value equal to a predetermined value in response to determining that the untransformed correlation coefficient value exceeds the threshold value.

Clause 24: In some examples of clauses 22 or clause 23, applying the transform function comprises determining that a second untransformed correlation coefficient value is less than a threshold value and applying a linear function to the second untransformed correlation coefficient value to determine a second transformed correlation coefficient value in response to determining that the second untransformed correlation coefficient value is less than the threshold value.

Clause 25: In some examples, a system includes means for receiving a first signal indicative of a first physiological parameter of a patient; means for receiving a second signal indicative of a second physiological parameter of the patient means for determining a trendline function based on values of the first physiological parameter and values of the second physiological parameter; means for determining transformed values of the first physiological parameter based on the trendline function; means for determining correlation coefficient values for the transformed values of the first physiological parameter and the values of the second physiological parameter; means for determining a limit of autoregulation of the patient based on the correlation coefficient values; means for determining an autoregulation status of the patient based on the limit of autoregulation; and means for outputting, for display, an indication of the autoregulation status.

Clause 26: In some examples, a system includes means for receiving a first signal indicative of a first physiological parameter of a patient; means for receiving a second signal indicative of a second physiological parameter of the patient, means for determining untransformed correlation coefficient values for values of the first physiological parameter and values of the second physiological parameter; means for determining transformed correlation coefficient values based on the untransformed correlation coefficient values; means for determining a limit of autoregulation of the patient based on the transformed correlation coefficient values; means for determining an autoregulation status of the patient based on the limit of autoregulation; and means for outputting, for display, an indication of the autoregulation status.

The details of one or more examples are set forth in the accompanying drawings and the description below. Other features, objects, and advantages will be apparent from the description and drawings, and from the claims.

DETAILED DESCRIPTION

Figure 1A:
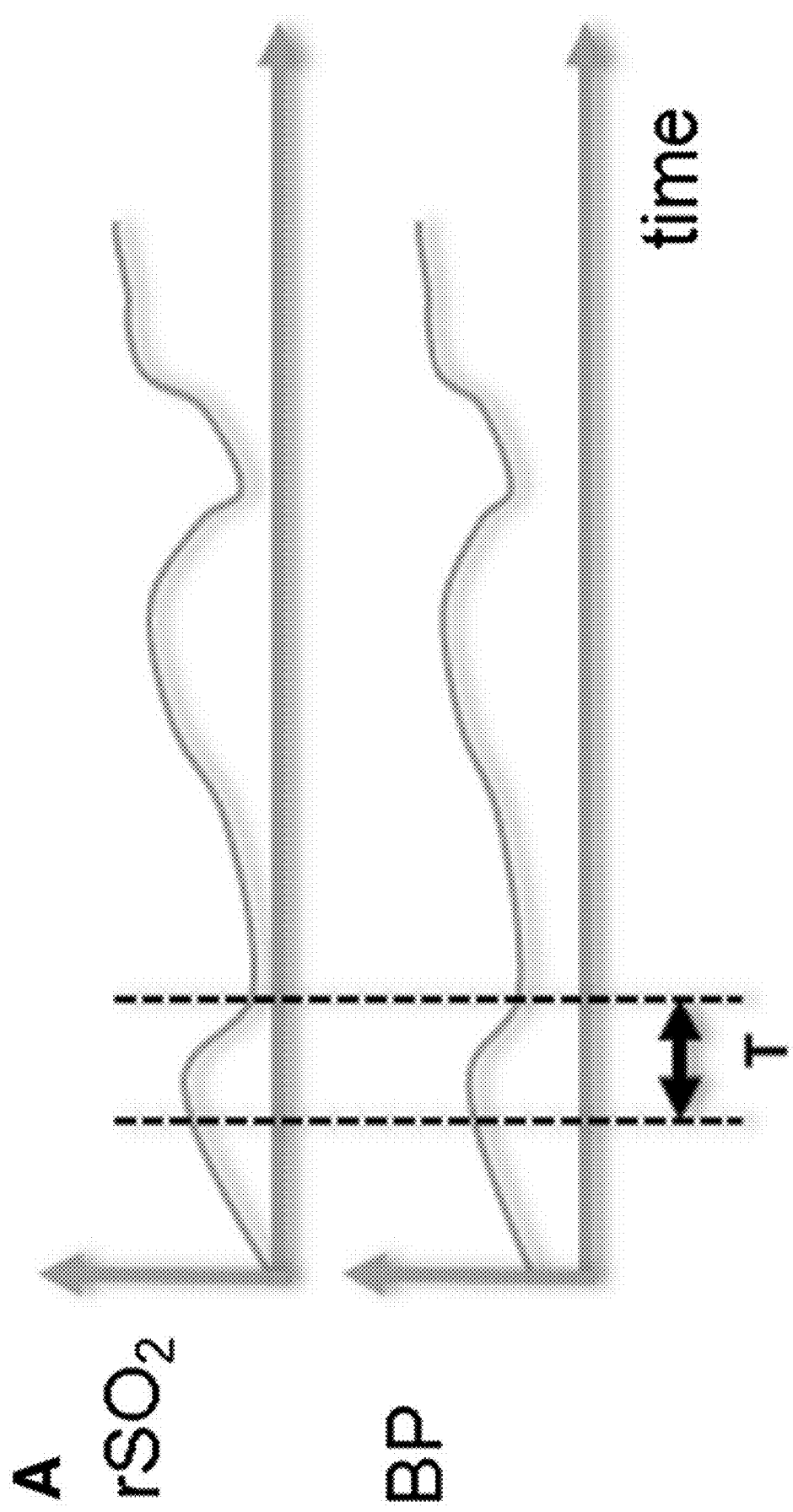
FIGS. 1A-1D are graphs illustrating the process of generating a cerebral oximetry index (COx) plot with COx values that are bounded by +1 and −1, in accordance with some examples of this disclosure.

This disclosure describes devices, systems, and techniques for determining an estimate of a limit of autoregulation based on a set of correlation coefficient values. Processing circuitry of a regional oximetry device may determine the set of correlation coefficient values based on sets of values of two physiological parameters. The processing circuitry may determine a limit of autoregulation based on transformed correlation coefficient values and/or transformed values of a physiological parameter. Accordingly, the processing circuitry may be able to determine a more accurate estimate of a limit of autoregulation, as compared to determining an estimate of the limit of autoregulation based on untransformed correlation coefficient values and untransformed values of a physiological parameter.

The transformed correlation coefficient values and/or transformed values of the physiological parameter may provide a more distinguishable indication of the boundaries of the intact region of autoregulation. For example, by using transformed values of a physiological parameter, the processing circuitry may be able to determine correlation coefficient values that more distinctly indicate the limits of autoregulation, as compared to correlation coefficient values based on untransformed values of the physiological parameter. The processing circuitry may determine a limit of autoregulation with higher confidence, as compared to another device that does not use transformed values.

The devices, systems, and techniques of this disclosure may allow for presenting a more accurate estimate of a limit of autoregulation of a patient and a more accurate indication of the autoregulation status of the patient. The presentation of more accurate and more stable information may result in increased confidence by a clinician viewing the presented information, which may lead to more informed decision making by the clinician. A clinician may lose confidence in the information presented by the processing circuitry if the information is less stable and/or less accurate. By transformed correlation coefficient values and/or transformed values of a physiological parameter, the processing circuitry may create a more distinct representation of the boundaries of the intact region of autoregulation. By determining an autoregulation status using the techniques of this disclosure, the processing circuitry may reduce the likelihood of an erroneous determination of autoregulation status.

The autoregulation status of a patient may be an indication that the cerebral autoregulation control mechanism of the patient is intact (e.g., functioning properly) or impaired (e.g., not functioning properly). A cerebral autoregulation control mechanism of the body may regulate cerebral blood flow over a range of systemic blood pressures. This range of systemic blood pressures may lie within a lower limit of autoregulation (LLA) and an upper limit of autoregulation (ULA). Outside of the LLA and the ULA, blood pressure directly drives CBF, and cerebral autoregulation function may thus be considered impaired. One method to determine the limits of autoregulation (e.g., the LLA and the ULA) noninvasively using near-infrared spectroscopy (NIRS) technology may include the cerebral oximetry index (COx) measure, which is a moving correlation index between mean arterial pressure (MAP) and regional oxygen saturation ($rSO_2$). The COx measure (e.g., the Pearson coefficient) is derived from the correlation between $rSO_2$ and MAP. COx relates to the regression line fit or linear correlation between $rSO_2$ and MAP over a time window having a particular length, such as three hundred seconds, in some examples. The COx method may be used to produce a representation of a patient's blood-pressure-dependent autoregulation status.

When the cerebral autoregulation is intact for a patient, there is typically no correlation between MAP and $rSO_2$. In contrast, MAP and $rSO_2$ typically directly correlate (e.g., the correlation index of COx is approximately 1) when the cerebral autoregulation is impaired. In practice, however, sensed data indicative of autoregulation may be noisy and/or there might be a slightly correlated relationship between variables (e.g., MAP and $rSO_2$) even when cerebral autoregulation is intact for the patient.

Some existing systems for monitoring autoregulation may determine a patient's autoregulation status based on various physiological parameter values (also referred to herein as physiological values). Such physiological values may be subject to various sources of error, such as noise caused by relative sensor and patient motion, operator error, poor quality measurements, drugs, or other anomalies. However, some existing systems for monitoring autoregulation may not reduce the various sources of error when utilizing the measured physiological values to determine the patient's autoregulation status. Furthermore, some existing systems may not determine and/or utilize a reliable metric to determine whether the autoregulation status calculated from the physiological values is reliable. Accordingly, the autoregulation status determined by such existing systems may be less accurate or less reliable.

In the intact region of autoregulation, there may be no correlation between MAP and $rSO_2$, whereas in the impaired region of autoregulation, the correlation index should approximate unity. In practice, however, the data may be noisy and/or the intact region may often exhibit a slightly positive relationship. This positive relationship may render traditional autoregulation limit calculations difficult to perform, resulting in the need for manual interpretation of the data using arbitrary thresholds. Further, the underlying mathematics of the technique may be asymmetric in terms of the results produced for impaired and intact regions and may be, in fact, not computable for the ideal case within the intact region.

A physician may monitor a patient's autoregulation through the use of various monitoring devices and systems that measure various physiological parameters. In certain aspects of the present disclosure, a regional oximetry device may be configured to monitor a patient's autoregulation by correlating measurements of the patient's blood pressure (e.g., arterial blood pressure) with measurements of the patient's oxygen saturation (e.g., regional oxygen saturation). In particular, the processing circuitry may derive COx values based at least in part on a linear correlation between the patient's blood pressure and oxygen saturation. In addition, in certain aspects of the present disclosure, the processing circuitry can monitor the patient's autoregulation by correlating measurements of the patient's blood pressure with measurements of the patient's blood volume (e.g., blood volume proxy). In particular, the processing circuitry can derive a hemoglobin volume index (HVx) based at least in part on a linear correlation between the patient's blood pressure and blood volume.

While features of the present disclosure are discussed with reference to COx, in other examples, various other linear correlations such as HVx may be determined to help evaluate a patient's autoregulation status. For example, a linear correlation between measurements of a patient's blood pressure and measurements of a patient's cerebral blood flow may derive a mean velocity index (Mx). As a further example, a linear correlation between measurements of a patient's blood pressure and measurements of a patient's intracranial pressure may derive a pressure reactivity index (PRx). In certain situations, these indexes may be utilized to determine or help evaluate a patient's autoregulation. The devices, systems, and techniques of this disclosure can also be applied to the determination of indices such as HVx, Mx, PRx, and/or any other indices, coefficients, and correlations. For example, processing circuitry may be configured to determine an estimate of a limit of autoregulation based on a set of HVx indices, a set of Mx indices, and/or a set of PRx indices.

Additional example details of the parameters that can be used for determining a limit of autoregulation may be found in commonly assigned U.S. Patent Application Publication No. 2016/0367197 filed on Jun. 16, 2016, entitled "Systems and Methods for Reducing Signal Noise When Monitoring Autoregulation," and commonly assigned U.S. Patent Application Publication No. 2017/0105631 filed on Oct. 18, 2016, entitled "System and Method for Providing Blood Pressure Safe Zone Indication During Autoregulation Monitoring," which are incorporated herein by reference in their entirety.

This disclosure describes a gradient adjustment method (GACOx) that may enhance the differences in COx values observed in the intact and impaired regions. Results from a porcine model, with eight subjects, are used to demonstrate that GACOx is successful in determining LLA values where traditional methods fail. In some examples, the derived GACOx indices exhibit a mean difference between the intact/impaired regions of 1.54±0.26 (mean±SD), compared to 0.14±0.10 for the traditional COx method. The GACOx may effectively polarize the COx data in order to better differentiate the intact and impaired zones and, in doing so, may make the determination of the LLA and ULA points a simpler and more consistent task. The method may lend itself to the automation of the robust determination of autoregulation zone limits. The gradient adjustment method may result in better discriminating between the correlating and non-correlating regions of physiological signals, such as the specific application of the partitioning of impaired and intact zones of cerebral autoregulation.

Figure 2:
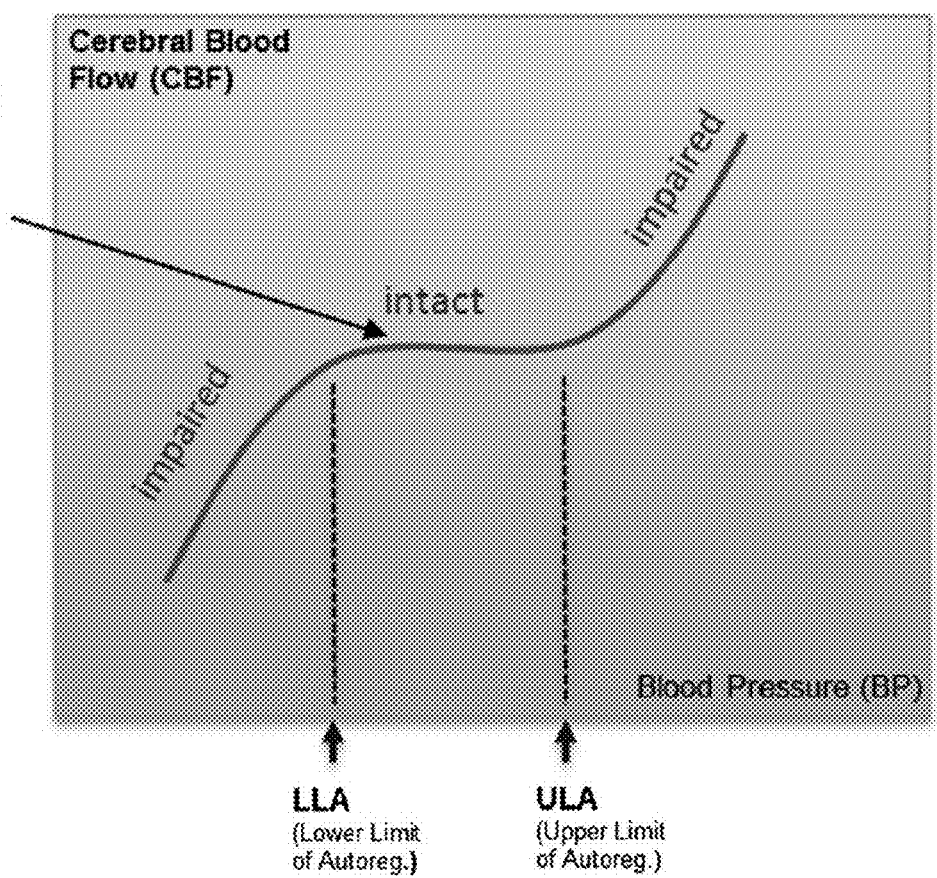
FIG. 2 is a graph illustrating cerebral blood flow as a function of blood pressure having an ideal curve with a flat (i.e., zero gradient) portion in the intact region.

The cerebral autoregulation control mechanism acts through complex myogenic, neurogenic, and metabolic mechanisms. This range spans a zone of intact autoregulation from the LLA to the ULA. Unregulated flow, and therefore impaired autoregulation, occurs at the extremes of blood pressure (i.e., below the LLA and above the ULA), where cerebral vasocontrol is no longer able to adequately control vascular resistance in response to further blood pressure changes. In these impaired regions, the blood pressure drives the flow and is therefore positively correlated with it; whereas in the intact region, cerebral control of blood flow is maintained in the event of blood pressure changes and no long-term correlation between the signals exists. This behavior is depicted in FIG. 2, which contains a schematic of the archetypal pressure-flow relationship for cerebral autoregulation. In this idealized depiction, the intact region displays a horizontal plateau indicating that no correlation between the parameters exists.

The correlation between the pressure drop across the brain-cerebral perfusion pressure—and cerebral blood flow may be quantified using a linear regression. The derived correlation coefficient, Mx, provides a measure of the coupling between pressure and cerebral flow. A common non-invasive proxy for Mx is COx: the cerebral oximetry index. COx is the correlation coefficient derived from the relationship between NIRS-based $rSO_2$ measurement and (MAP).

Figure 1B:
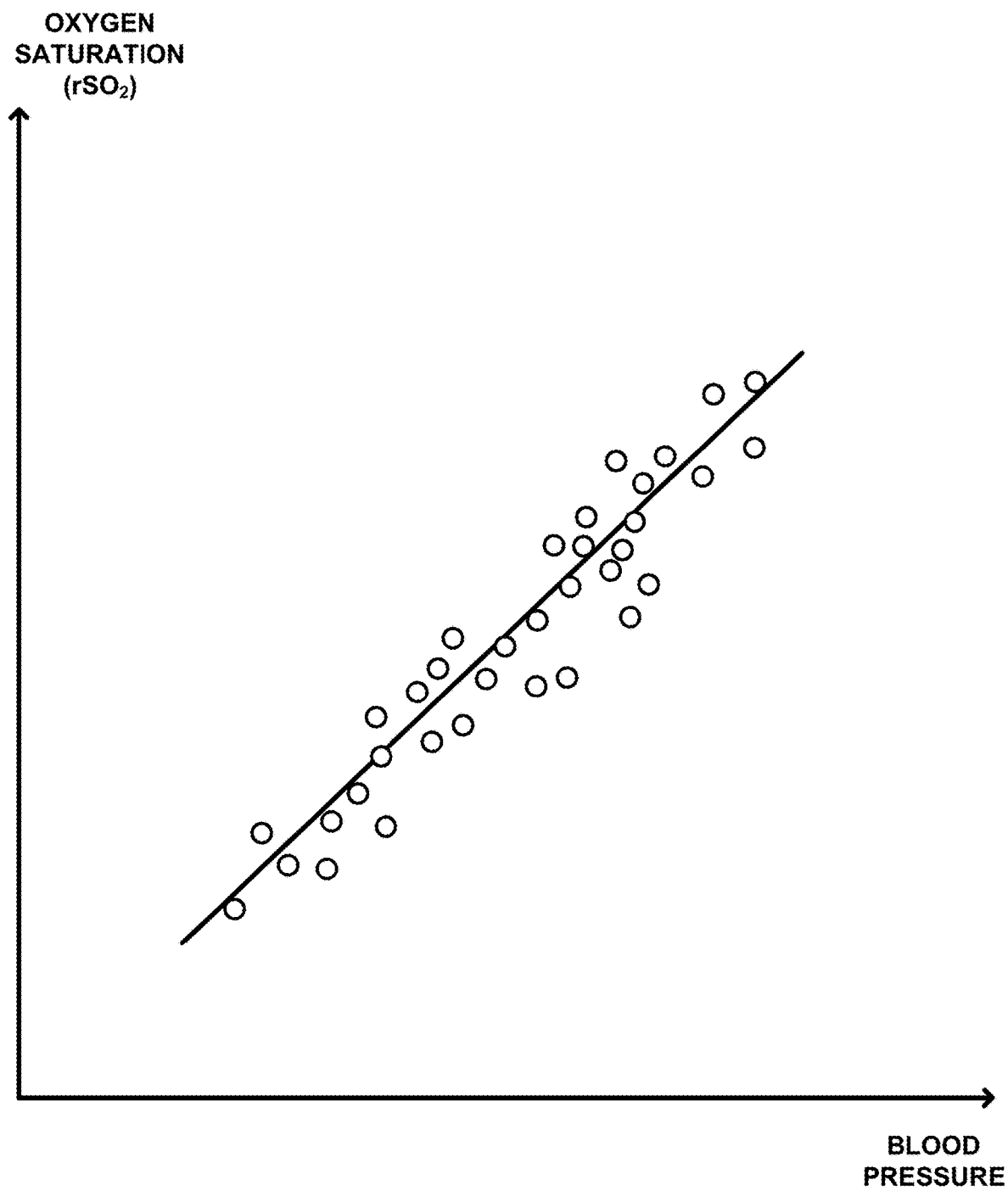

FIGS. 1A-1D are graphs illustrating the process of generating a cerebral oximetry index (COx) plot with COx values that are bounded by +1 and −1, in accordance with some examples of this disclosure. The method for determining COx is presented in FIGS. 1A-1D. The plot in FIG. 1A shows the analysis window of period T, which is run across the acquired $rSO_2$ and MAP signals. The data within this window may be plotted against each other as depicted in FIG. 1B. The window length is chosen to capture the characteristic periodicity of the physiological slow waves present in the blood pressure signal. In practice, the time window may span three hundred seconds, although other window lengths have been suggested. Linear regression of the data may then performed and the Pearson correlation coefficient determined for each window position, as shown in Equation (1):

$$R = cov(X,Y)/(\sigma_X \sigma_Y) \quad (1)$$

The vectors X and Y are the two signals under investigation, cov(X, Y) is the covariance between X and Y, and $\sigma_X$, $\sigma_Y$ denote standard deviations: replacing X and Y by MAP and $rSO_2$ defines the COx measure (similarly, using CPP and CBF results in the Mx measure. However, MAP may be a proxy for CPP and/or CBF velocity may be a proxy for CBF when computing Mx). The window may then be slid over the signal in incremental steps and the process repeated. In practice, this time step is around 5-10 seconds, which may be chosen to filter out low frequency components (including cardiac and respiratory modulations). At each step, a COx value may be determined and added to an aggregated COx plot (see FIG. 1C), and these values may then be used to form the COx plot often used in practice, where the values may be binned in 5 mmHg increments (see FIG. 1D). A strong positive correlation may exist between MAP and $rSO_2$ in regions of autoregulatory impairment, hence the COx values may tend to a value of unity. Regions of intact autoregulation, however, may produce no correlation between $rSO_2$ and changes in blood pressure and hence the correlation coefficient (COx) may be zero in the intact region. In this ideal case, a step change in the binned COx values may occur when transitioning from intact to impaired regions at the LLA or ULA. In practice, however, the binned data may be generally noisy and a COx threshold value somewhere between 0 and +1 may be used to differentiate the correlating and non-correlating portions of the plot. Values used in studies reported elsewhere in the literature for this threshold are 0.3, 0.4 and 0.5.

FIG. 2 is a graph illustrating cerebral blood flow as a function of blood pressure having an ideal curve with a flat (i.e., zero gradient) portion in the intact region. There may be issues with the correlation method described above in two distinct areas: physiological and mathematical. First, the pressure-flow curve may not contain a central 'flat' region of zero gradient during intact cerebral autoregulation as depicted in the ideal case of FIG. 2. In practice, a positive gradient may exist in this region, although less steep than in the impaired region.

Figure 3:
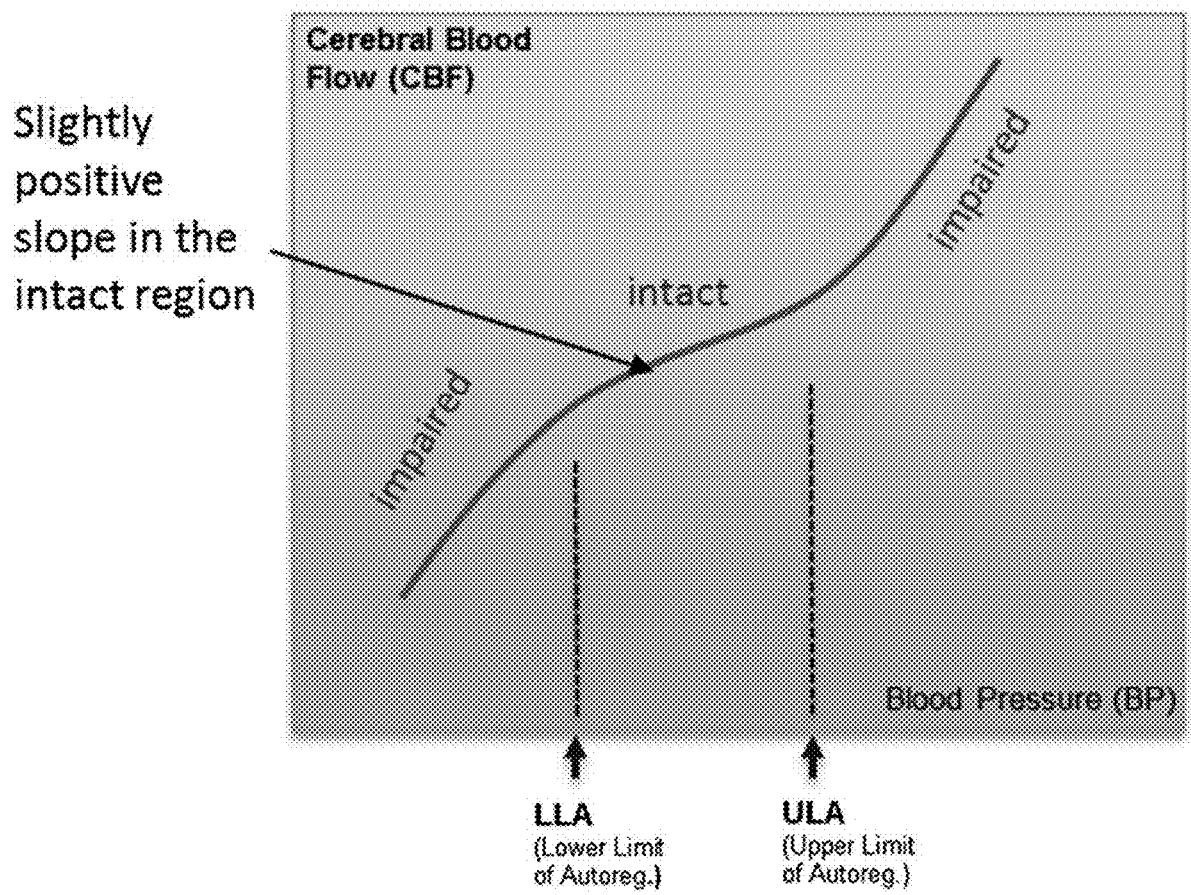
FIG. 3 is a graph illustrating cerebral blood flow as a function of blood pressure having a curve with a slightly positive relationship in the intact region.

FIG. 3 is a graph illustrating cerebral blood flow as a function of blood pressure having a curve with a slightly positive relationship in the intact region. The idea that there is no change in the range of intact autoregulation originates from Lassen, who described the existence of a constant plateau for values between 60 and 150 mmHg. However, the constant plateau concept may not always be true. A slope may exist in the intact region, which may provide enough evidence that brain perfusion in the intact region is not constant. A pressure-passive behavior above the LLA may be relatively common. The exact mechanism that causes the functional dependence of CBF has not been determined, but the assumption of zero slope in the intact region may not always be true. In the case of such behavior, the derived COx value in the intact region may also tend to unity, making it indistinguishable from regions of impaired autoregulation.

Figure 1C:
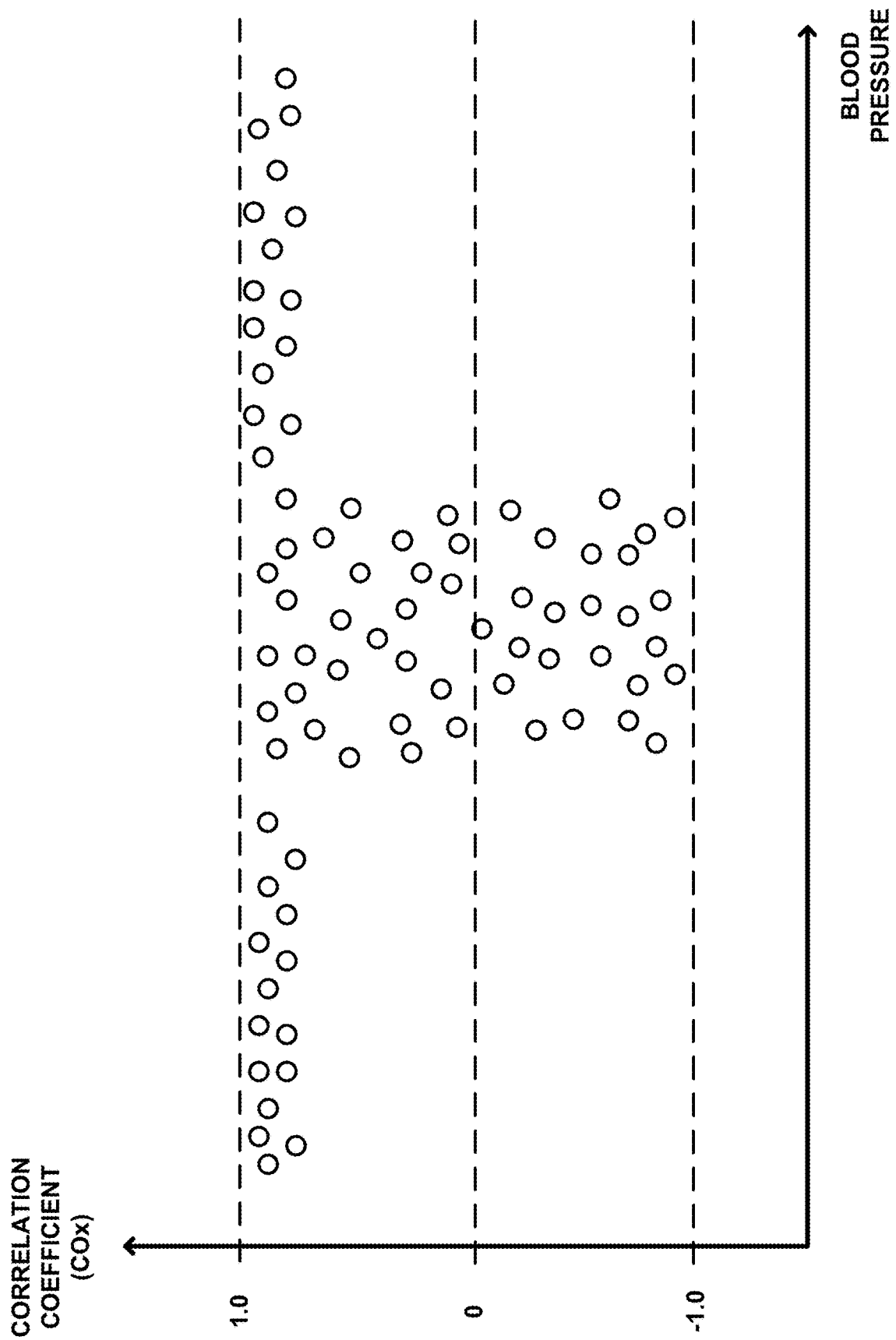
Figure 1D:
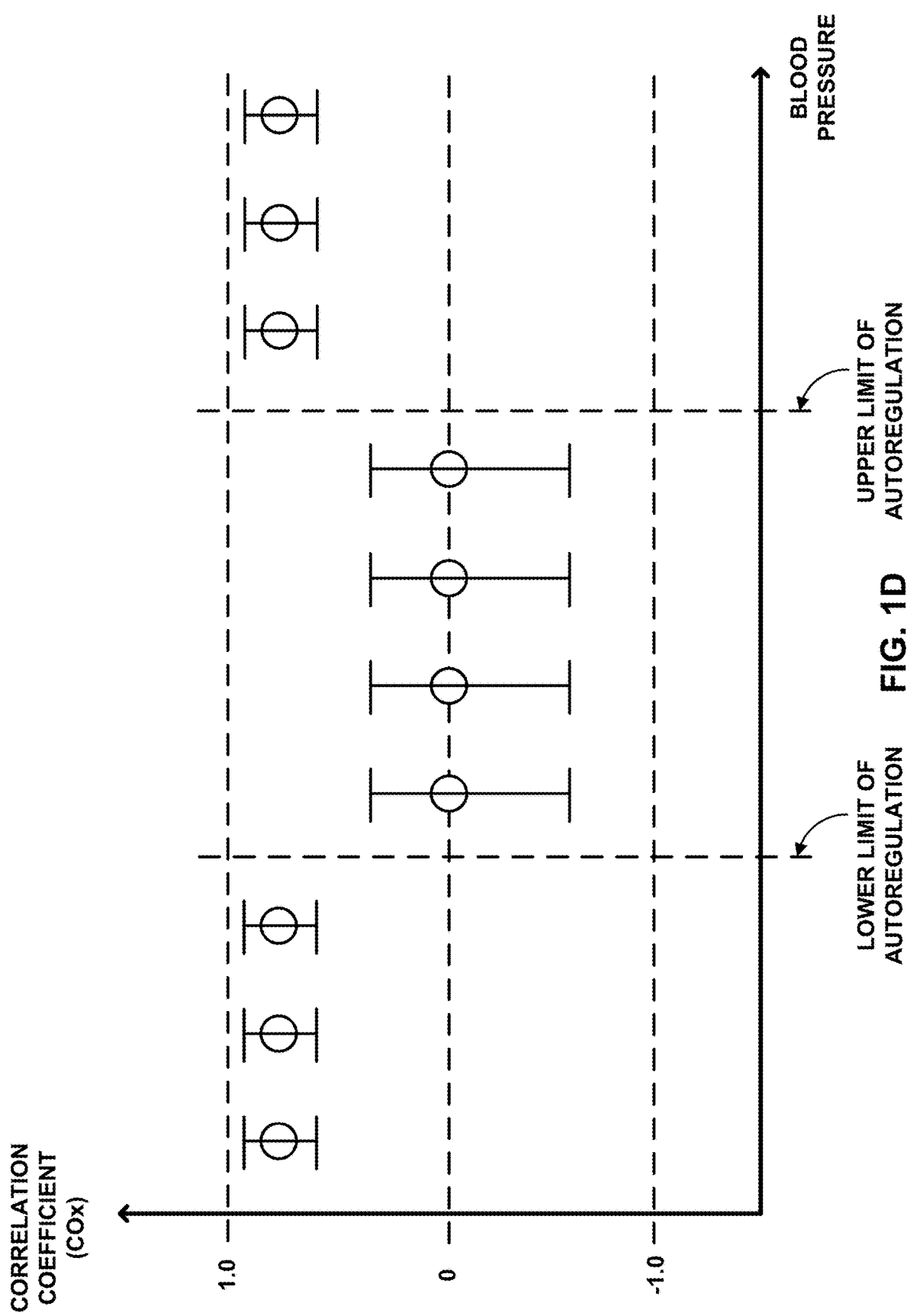

Second, the correlation method itself may not clearly define the two regions (even if an intact cerebral autoregulation region of zero slope is present in the data). A strong correlation may exist near unity for the impaired region as MAP and $rSO_2$ may trend strongly with each other. However, during the intact region, the two signals may be decoupled. Thus, for some time periods, both signals may be trending in the same direction, showing an apparent correlation; and in other time periods the two signals may be trending in the opposite direction, showing a negative apparent correlation. Further, there may be many periods where the two have a mix of trending and anti-trending behavior in the same time window. The COx value during intact cerebral autoregulation to vary from +1 to −1 randomly over time, with only the average value over time tending to zero (the expected distribution of the computed points prior to binning is depicted in FIG. 1C). The COx method may be asymmetric in its behavior according to zone. This may also be true for all such correlation-based methods: the correlation coefficient (Mx), hemoglobin volume index (HVx), the pressure reactivity index (PRx), laser-Doppler index (LDx), etc. Further, the Pearson correlation coefficient may, in theory, "blow up" for the ideal horizontal relationship between $rSO_2$ and BP. This can be seen from Equation (1), where the standard deviation of the $rSO_2$ signal may be zero and the index at that region may become undefined (the method therefore requires some noise in the data and/or a non-horizontal flat region in the curve for this not to occur).

Taking the above into account, this disclosure describes techniques for partitioning the intact and impaired cerebral autoregulation zones. The techniques may employ a gradient adjustment prior to performing the correlation analysis, which may shift the expectation from a strong value at unity and a mean value near zero for the determined correlation coefficients (COx) to strong values at +1 and −1, corresponding to impaired and intact regions respectively. The gradient adjustment may be based on the slope of a trendline that fits the $rSO_2$-MAP curve. This adjustment may facilitate partitioning of the data and hence aids determination of the LLA and ULA boundaries. The techniques of this disclosure may better discriminate correlating and non-correlating signal segments in data used to determine the status of cerebral autoregulation. However, the techniques may also be generally applicable in the analysis of any other signals where regions of correlation and non-correlation require identification.

Figure 4A:
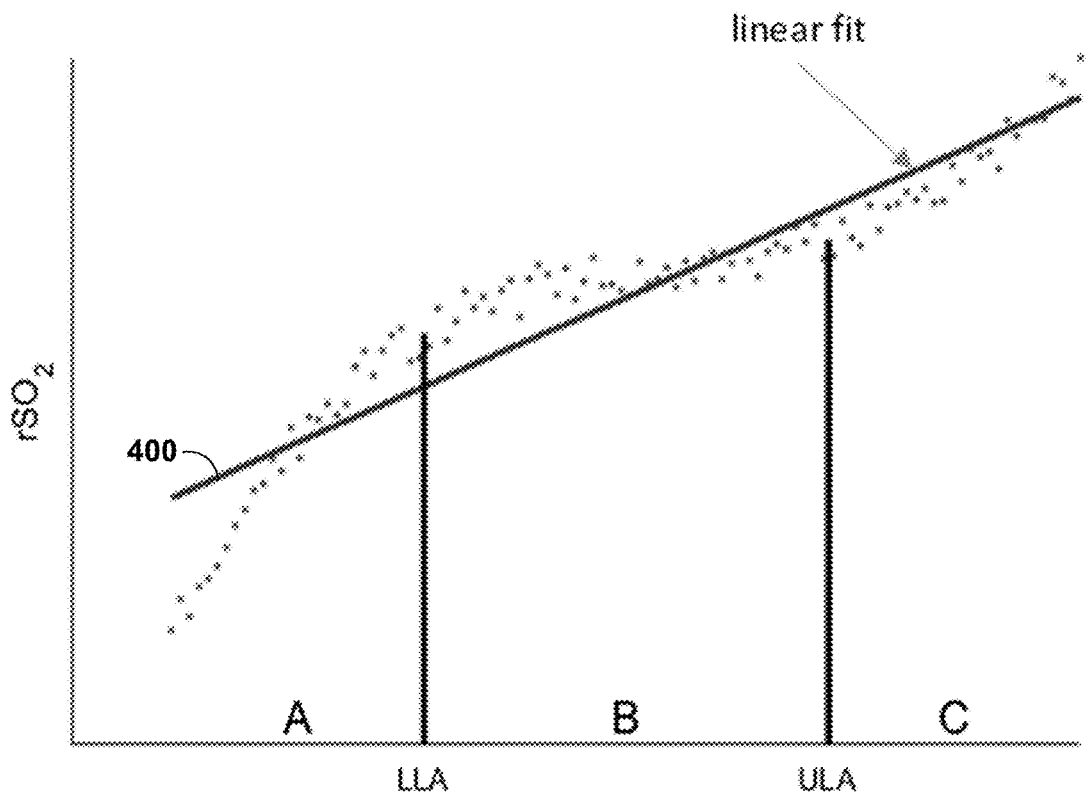
FIGS. 4A and 4B are graphs illustrating regional oxygen saturation measurement ($rSO_2$) as a function of mean arterial pressure (MAP) before and after applying a gradient adjustment, in accordance with some examples of this disclosure.
Figure 4B:
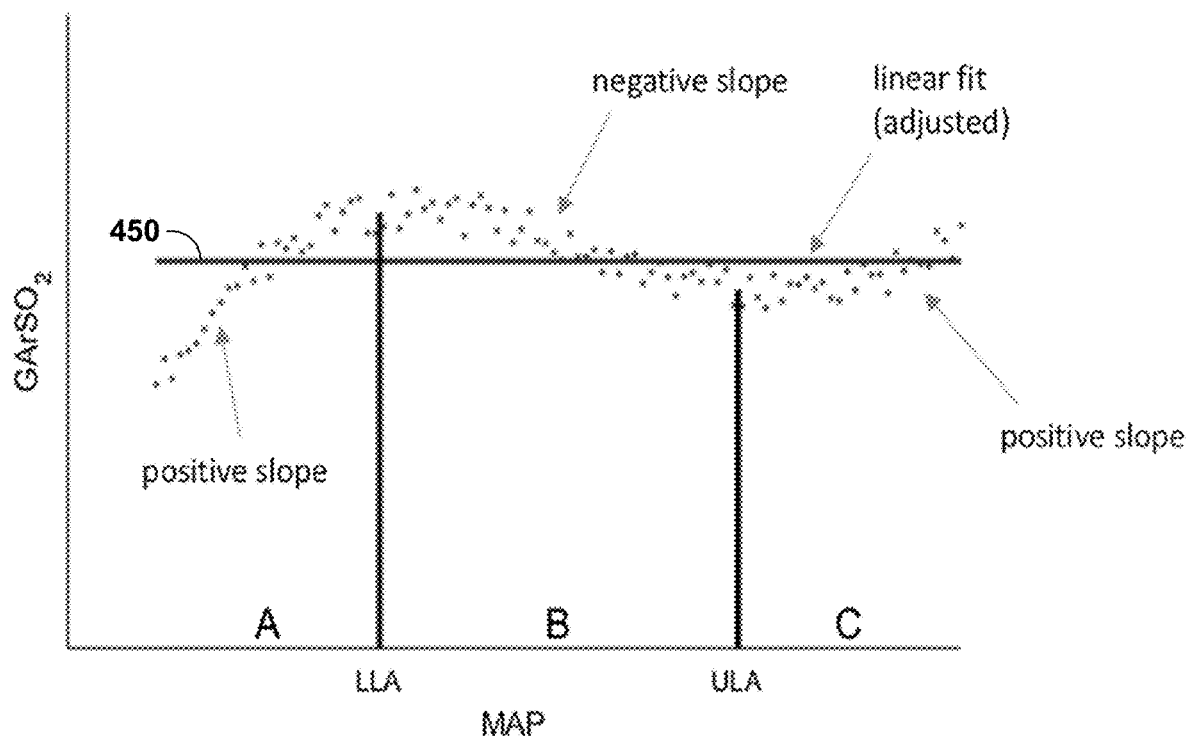

FIGS. 4A and 4B are graphs illustrating $rSO_2$ as a function of MAP before and after applying a gradient adjustment, in accordance with some examples of this disclosure. The gradient adjustment (GA) method may significantly enhance the delineation between impaired and intact autoregulation zones in the COx plot by manipulating the underlying relationship so that the intact region may have a distinct negative gradient while the impaired regions may still have a distinct positive gradient. In the method, which is illustrated schematically in FIGS. 4A and 4B, we may compensate for the possibility of a zero or positive gradient in the intact region B by transforming the $rSO_2$ values before determining the correlation. This is carried out by determining regression line 400 of the $rSO_2$-MAP curve, shown in FIG. 4A, and subtracting the corresponding values from the $rSO_2$ signal. Regression line 400 may be a trendline that is a best fit of the data, such as a line with minimized sum of squares of the differences between the data and regression line 400. Thus, regression line 400 may approximate the trend of the data in the $rSO_2$-MAP curve. Regression line 400 may be defined by a function given by Equation (2):

$$y(x) = mx + b \quad (2)$$

Figure 5A:
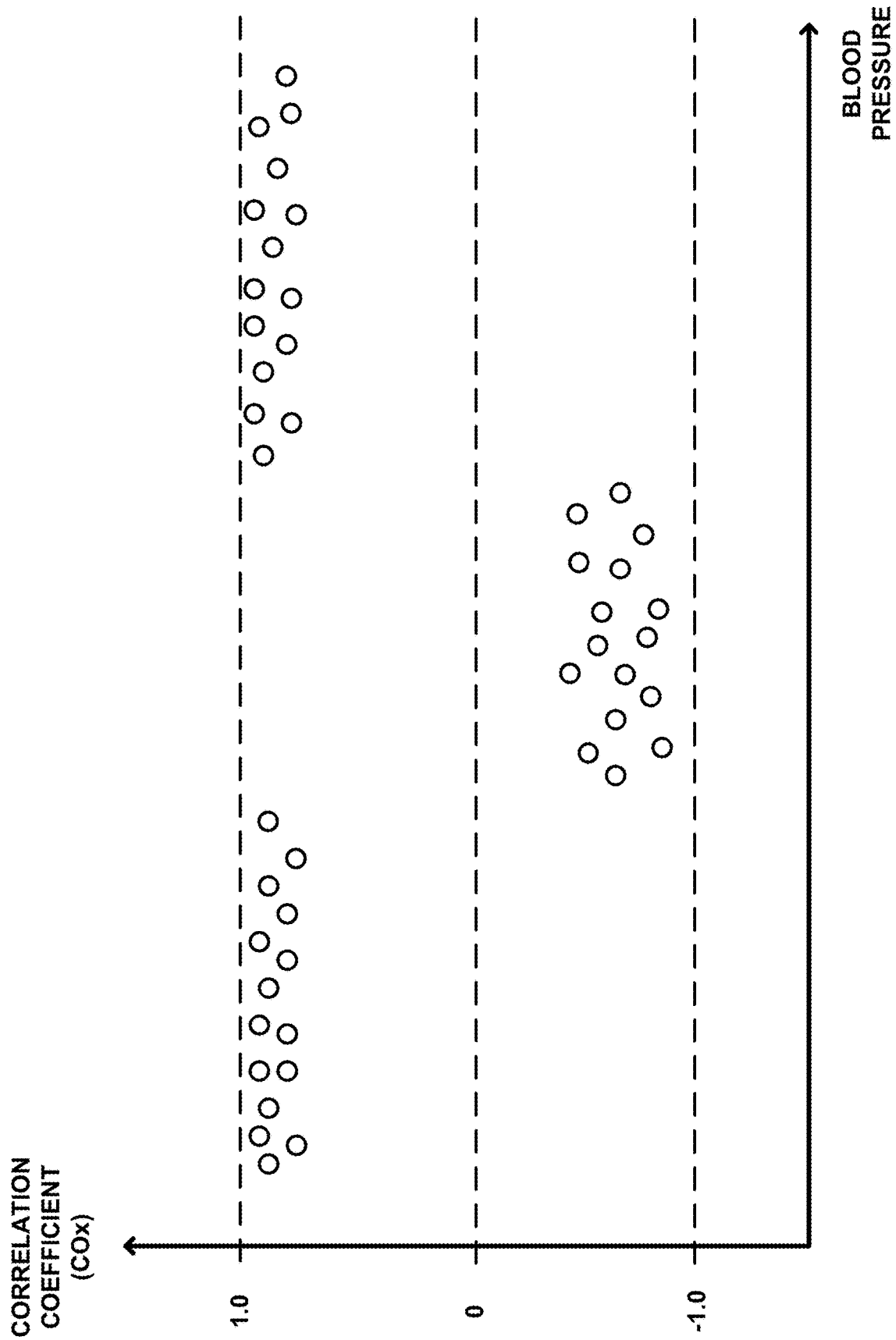
FIGS. 5A and 5B are graphs of GACOx as a function of blood pressure that illustrate the polarization of the intact and impaired data caused by the gradient adjustment of the COx data, in accordance with some examples of this disclosure.
Figure 5B:
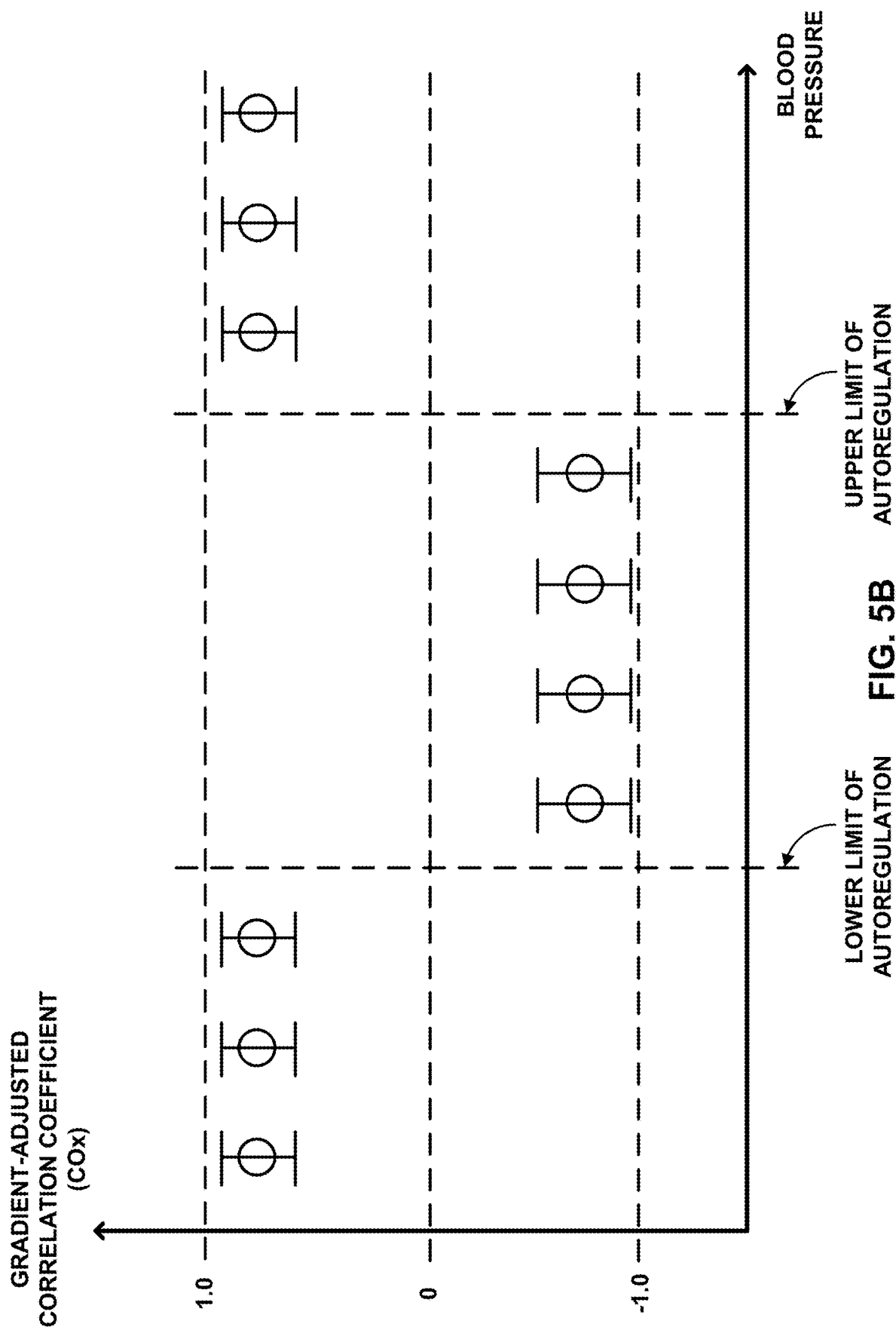

In Equation (2), y corresponds to $rSO_2$ values, x to MAP values, m is the slope (i.e., gradient) of the line and b the intersection of the line with the y axis. The gradient-adjusted $rSO_2$ ($GArSO_2$) may then be determined as shown in Equation (3):

$$GArSO_2(x_i) = rSO_2(x_i) - y(x_i) \quad (3)$$

Where $x_i$ is the MAP value for the corresponding i-th element in the data array and $y(x_i)$ is the corresponding value of $rSO_2$ on the regression line. As we expect the overall gradient to be greater than that of region B and less than A and C, this gradient adjustment may result in a strong negative slope of the data in region B, while maintaining positive slopes in regions A and C (see FIG. 4B). Regression line 450 may be an adjusted version of regression line 400 such that the distance between each data point of $rSO_2$ and regression line 400 may be equal to the distance between each data point of $GArSO_2$ and regression line 450. Thus, by using $GArSO_2$ values instead of the original $rSO_2$ values, and/or by using gradient-adjusted MAP (GAMAP) values instead of the original MAP values, a gradient-adjusted COx (GACOx) plot may be determined. The GACOx method may effectively polarize the COx data in order to better differentiate the intact and impaired zones and, in doing so, may make the determination of the LLA and ULA points a simpler and more consistent task. This polarization of the data to the +1 and −1 values is shown schematically in FIGS. 5A and 5B. FIGS. 5A and 5B are graphs of GACOx as a function of blood pressure that illustrate the polarization of the intact and impaired data caused by the gradient adjustment of the COx data, in accordance with some examples of this disclosure.

Figure 6:
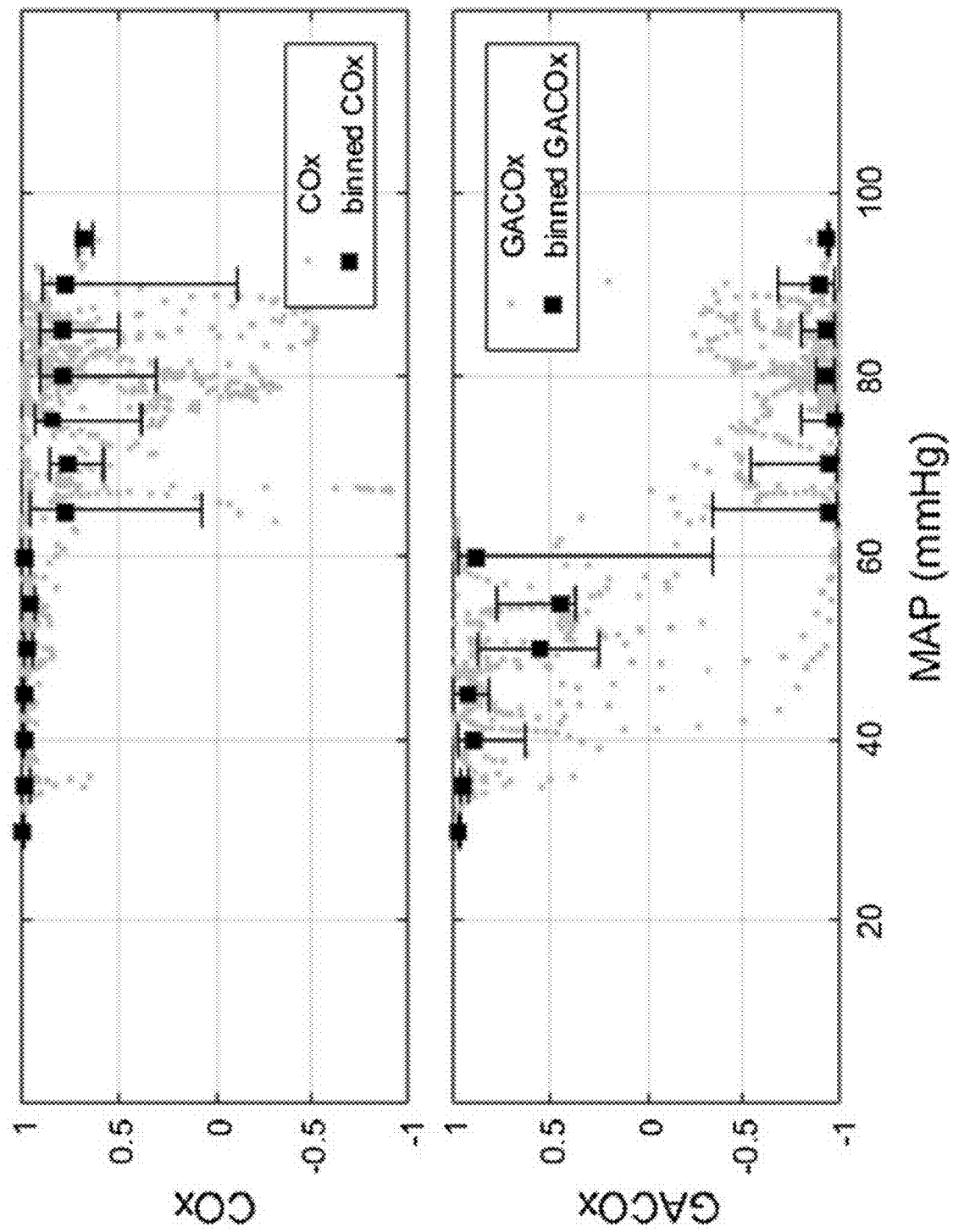
FIG. 6 depicts graphs showing an example COx plot and a corresponding GACOx plot for a single trial, in accordance with some examples of this disclosure.

FIG. 6 is an example COx plot and a corresponding GACOx plot for a single trial, in accordance with some examples of this disclosure. FIG. 6 shows an example of a traditional COx plot and a GACOx plot (this comprises one of the data sets used in the study described in detail below with respect to FIGS. 7 and 8). The traditional COx plot in the figure may be typical of data with a slightly positive gradient in the intact cerebral autoregulation region. It may exhibit tight clustering towards a value of unity across the whole blood pressure range, making the LLA relatively difficult to resolve using traditional methods of analysis. However, after the application of gradient adjustment, a clearly visible separation may appear between the points corresponding to the intact and impaired regions in the GACOx plot; the data may tend to cluster around values of 1 and −1 respectively.

The plots of FIG. 6 show the data that processing circuitry may use to determine the LLA. However, in some examples, the processing circuitry may use the same or similar techniques to determine the ULA. The MAP study data shown in FIG. 6 does not go high enough (e.g., more than eighty or ninety mmHg) for the COx values or the GACOx values to increase back to unity (+1). Therefore, the data shown in FIG. 6 may not have sufficiently high MAP values for the processing circuitry to determine a ULA. If the range of MAP values extends higher, then the GACOx may have headed back to +1. FIGS. 5A and 5B may show examples of data sets with sufficiently high MAP values or BP values for processing circuitry to determine a ULA.

Three reference methods were employed for the determination of the limits of autoregulation for comparison with GACOx: manual inspection and two automated algorithms. First, the manual method may involve printing out the COx plots for eight data sets determining the LLA from the plot. In the event of a disagreement among determinations, the manual LLA value for each animal was defined as the median of the three evaluations.

Second, for an automated algorithm, a value of 0.5 may be set as the limiting value for the transition between the low-impaired region and the intact region. The binned data may be inspected, starting with the lowest blood pressure bin, moving up a 5-mmHg bin at each increment. The LLA may be determined as the MAP value corresponding to the first binned COx below 0.5. Third, for another automated algorithm, the LLA may be determined when there are at least three consecutive binned values below the 0.5 threshold. This may be done to mitigate against false detections due to erroneous noisy data points below the threshold. The GACOx LLAs may be determined using both a manual and automated algorithm. For the automated algorithm, the threshold may be simply set to zero and the first point below zero may be determined as the LLA.

The analysis of the method presented herein was performed retrospectively based on data from an animal study originally designed to investigate the characterization of cerebral autoregulation. The study consisted of a healthy porcine model (N=8, 8 female), aged 8.4±0.5 weeks (mean±SD), with a weight of 13.3±1.7 kg (mean±SD). The protocol was reviewed and approved by the PCRS Animal Care and Use Committee. The study was conducted in GLP like fashion accordance with 21 CFR Part 58 at an Association for Assessment and Accreditation of Laboratory Animal Care (AAALAC) accredited site. The following standards in terms of appropriate use of animals for biomedical research and/or training were adhered to: The U.S. Animal Welfare Act amendment of 1976 (Title 9, Code of Federal Regulations, Chapter 1, Sub-chapter A, parts 1, 2 and 3) and the current U.S. National Institute of Health's Guide for the Care and Use of Laboratory Animals published by the National Research Council.

Fentanyl, isoflurane, propofol and vecuronium were used as anesthetic agents and heparin as an anticoagulant. NIRS sensors (INVOS SAFB-SM) were placed on the animals' head between the ears. These were attached to the monitor (INVOS 5100C oximeter, 5100C-PA preamp unit (Medtronic, Boulder, Colo.)). NIRS cerebral signals (both raw signals and the output $rSO_2$ signal) and a blood pressure signal were collected. The animal was ventilated with a tidal volume of 6-8 mL/kg, FiO2 was adjusted to maintain 95% arterial saturation and PEEP was 3 cmH2O. Respiratory rate was adjusted to maintain end-tidal CO2 between 38 and 45 mmHg. Heating pads were used to maintain normal body temperature as necessary.

The signals used in the analysis were acquired during episodes of induced hemorrhagic shock and vasoconstriction using an a-agent (norepinephrine). The protocol allowed mostly for blood pressure variations which resulted in multiple crossings of the LLA. A few high-pressure spikes were seen in the data but not enough to adequately define a ULA in most of the cases, hence only LLAs were considered in this study. The MAP was calculated from the raw blood pressure signal by an in-house peak detection algorithm which determines systolic and diastolic blood pressure on a beat-by-beat basis. This is averaged over ten seconds and output synchronously with $rSO_2$, which was acquired directly from the pre-amp signal from an INVOS™ 5100C regional oximeter (Medtronic, Boulder, Colo.).

A moving three-hundred-second window was employed to analyze the MAP and $rSO_2$ signals. This was incremented along the signals in a series often-second steps. The determined COx metric values were binned in 5 mmHg blood pressure increments, and the reference LLAs determined using the three methods described above. Bins with fewer than three data points were not considered as representative and were excluded from the analysis. Box plots were used to show the relative (aggregated) distributions of the COx and GACOx data either side of the determined LLAs. The difference in the median values of the COx and GACOx data was taken as a measure of the separation of the intact and impaired data.

Figure 7:
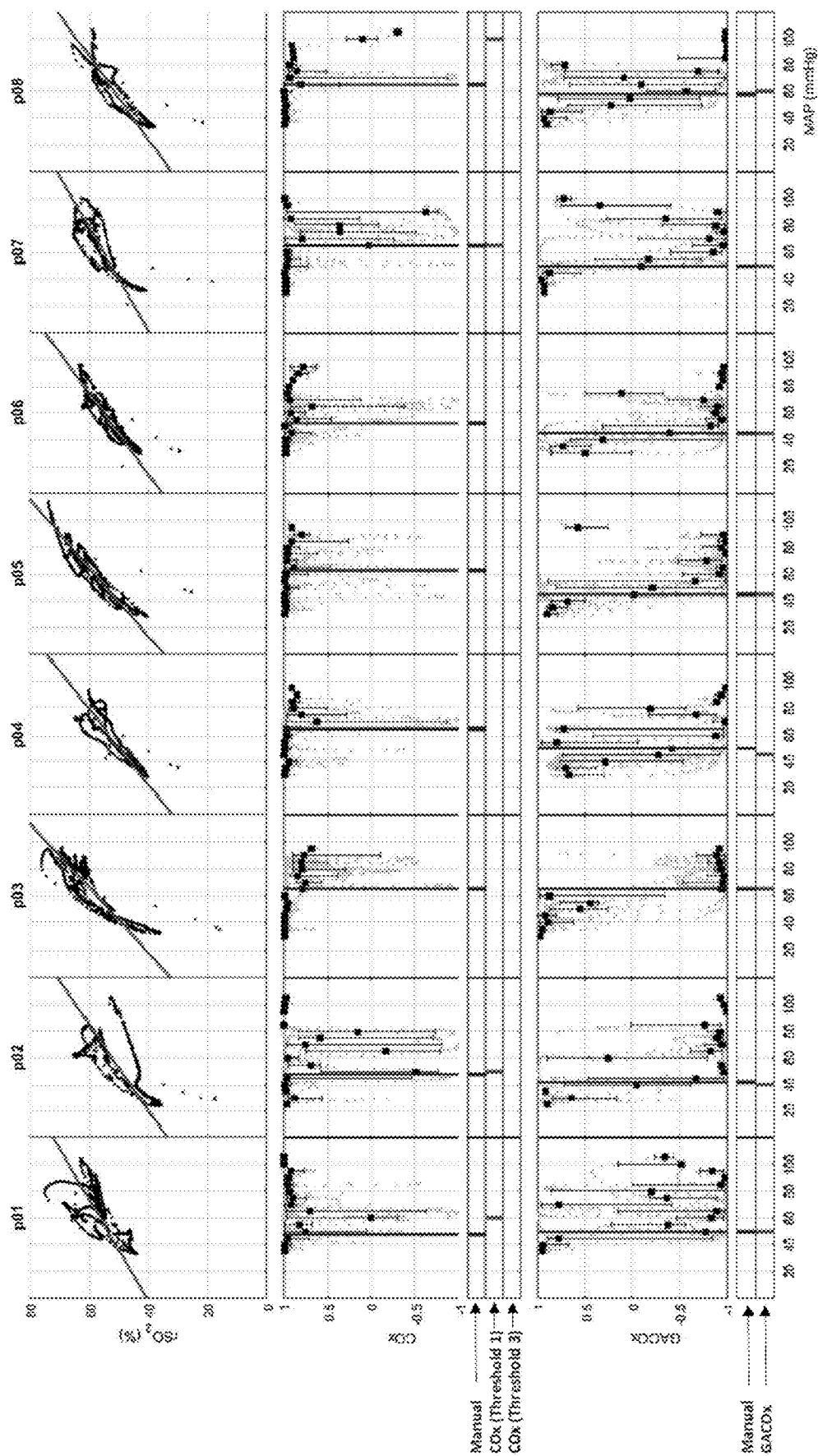
FIG. 7 illustrates plots of $rSO_2$ versus MAP, implementation of the traditional COx method with manually selected lower levels of autoregulation (LLAs), and implementation of the GACOx method with manually selected LLAs, in accordance with some examples of this disclosure.

FIG. 7 illustrates plots of $rSO_2$ versus MAP, implementation of the traditional COx method with manually selected LLAs, and implementation of the GACOx method with manually selected LLAs, in accordance with some examples of this disclosure. FIG. 7 shows COx and GACOx plots for all the animals in the study described herein. The processing circuitry of this disclosure may also be configured to determine a ULA in a similar manner. The top row shows $rSO_2$ versus MAP plot with the regression line (i.e., trendline) used for the gradient adjustment method. The middle row shows a traditional COx method with the manually selected LLA (drawn through the data) and an indication strip below showing the locations of the manual LLA versus the LLAs determined by the automatic COx algorithms (threshold 1 and threshold 3). The bottom row shows GACOx method with the manually selected LLA (drawn through the data) and an indication strip below showing the locations of the manual LLA versus the LLA determined by the GACOx algorithm (COx cerebral oximetry index, GACOx gradient adjusted COx measure, LLA lower limit of autoregulation).

The plots include the LLAs determined using the manual reference method. The position of the LLAs determined from automated COx and GACOx algorithms described above are also indicated below each respective plot. The corresponding linear fits of the MAP versus $rSO_2$ data, used to adjust the indices, can also be seen in the top row plots. The GACOx plots may exhibit a clear transition from positive to negative values. This is in contrast to the traditional COx plots, where many of the transition regions may be difficult to discern, hence making LLA identification problematic. A summary of the determined LLAs using GACOx and the reference methods is provided in Table 1. It can be seen that both automated algorithmic methods, when used on the traditional COx plot, failed to identify a number of LLAs due to data not transiting below the threshold of 0.5 (in fact, the 'Threshold 3' algorithm failed for all cases). However, the GACOx algorithm produced LLAs for all data sets which can be seen from FIG. 7 to be very close in value to those determined manually (5 out of the 8 LLAs are in complete agreement with a mean difference of 1.25 mmHg and a maximum difference of 5 mmHg).

TABLE 1

LLAs computed using various approaches.

| Method | p01 | p02 | p03 | p04 | p05 | p06 | p07 | p08 |
|---|---|---|---|---|---|---|---|---|
| COx (manual) | 48 | 48 | 65 | 65 | 63 | 52 | 65 | 65 |
| COx algorithm (threshold1) | 60 | 50 | FAIL | FAIL | FAIL | FAIL | 65 | 100 |
| COx algorithm (threshold3) | FAIL | FAIL | FAIL | FAIL | FAIL | FAIL | FAIL | FAIL |
| GACOx (manual) | 50 | 42 | 65 | 50 | 45 | 45 | 50 | 58 |
| GACOx algorithm | 50 | 40 | 65 | 45 | 45 | 45 | 50 | 60 |

Figure 8:
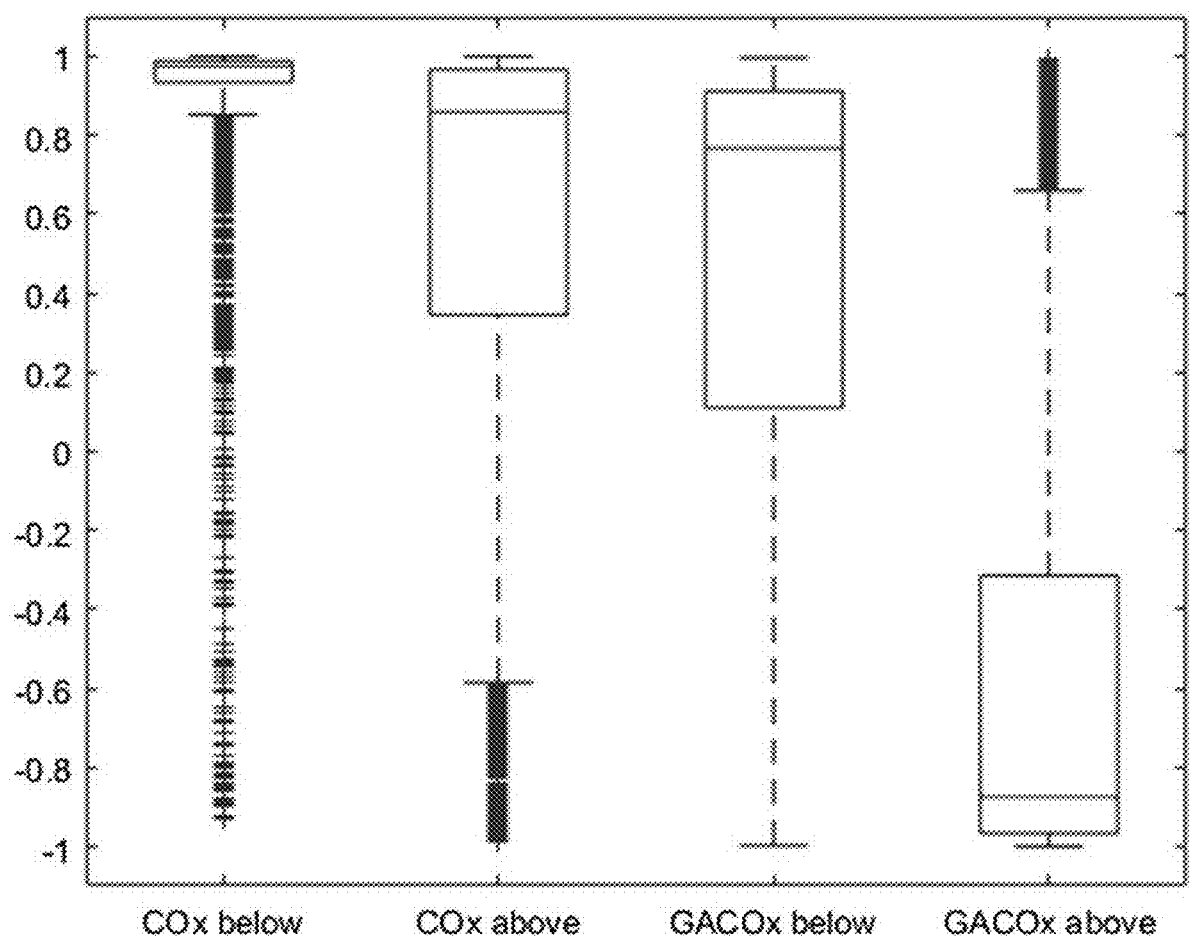
FIG. 8 is a graph illustrating a box plot of COx and GACOx values below and above the manually derived LLAs, in accordance with some examples of this disclosure.

FIG. 8 illustrates a box plot of COx and GACOx values below and above the manually derived LLAs, in accordance with some examples of this disclosure. FIG. 8 shows the boxplots for the COx values and GACOx values split either side of their respective manually derived LLAs to highlight the differences between the data distributions in the impaired and intact regions. It may be observed that there is a significant overlap of COx data points either side of the LLA for the traditional method whereas a clear difference is apparent for the gradient adjustment method. The line inside the box represent the median, while the boxes edges represent the 25 and 75 percentiles. The whiskers represent values 1.5 times the box length. Data points outside this limit are plotted as outliers (COx cerebral oximetry index, GACOx gradient adjusted COx measure, LLA lower limit of autoregulation).

Table 2 contains the difference in the median values either side of the LLAs for the automated COx and GACOx methods for each of the eight studies. These range from 0.06 to 0.37 for the traditional method, whereas the gradient adjustment method ranges from 1.05 to 1.80 (dimensionless units). The mean±SD for this difference is 0.14±0.10 for the traditional COx and 1.54±0.26 for the GACOx.

TABLE 2

Difference of the median values above and below the manually derived LLAs for each case for the COx and GACOx data sets.

| Data set | COx | GACOx |
| --- | --- | --- |
| p01 | 0.07 | 1.54 |
| p02 | 0.16 | 1.76 |
| p03 | 0.19 | 1.80 |
| p04 | 0.10 | 1.05 |
| p05 | 0.06 | 1.69 |
| p06 | 0.09 | 1.33 |
| p07 | 0.37 | 1.74 |
| p08 | 0.10 | 1.42 |
| Mean | 0.14 | 1.54 |
| Standard deviation (SD) | 0.10 | 0.26 |

The use of traditional correlation measures for the identification of the intact and impaired regions of autoregulation may include inherent physiological and mathematical limitations. Physiologically, it may be difficult to differentiate between intact and impaired regions when a slightly positive slope exists in the intact region of the $rSO_2$-MAP plot. Two mathematical issues may exist: the asymmetric data clustering in the intact and impaired zones; and the computation of a correlation coefficient for the intact region with idealized data (with a horizontal curve) may lead to dividing by zero in Equation (1). The gradient adjusted method detailed in this disclosure was applied to data where the traditional COx method failed to identify an LLA in most of the data sets studied, even when a reasonably high threshold value of 0.5 was employed. A manual assessment of the data did find LLAs for all data sets, but this was critically dependent on the subjective interpretation of the reviewers and required a 'user-defined' threshold well above those currently used in the literature.

The gradient adjustment method may mitigate against the existence of a positive slope in the intact region by altering the underlying $rSO_2$-MAP relationship so that the intact region may exhibit a negative slope while the impaired regions retain a positive slope. In this way, the revised GACOx plot may exhibit a clear grouping of the data tending to +1 for impaired and −1 for intact autoregulation. This may allow for a more robust and reliable method for detecting the decision boundary at the LLA. In fact, in many cases, the method may facilitate the evaluation of otherwise undefinable limits using algorithms based on the traditional method (cf. Table 1, COx algorithms). Although thresholds were obtained manually from the traditional COx curves, these were based on the individual interpretation of the reviewer and required adjustment of perceived thresholds which were data dependent and markedly above those used in practice (0.3-0.5).

The gradient adjustment method may be applied to other correlation-based measures of autoregulation: for example, a blood volume signal, an ICP signal or a measure of flow velocity could be used in place of $rSO_2$ in order to apply this correction to HVx, PRx or Mx respectively (e.g. GAHVx, GAPRx, GAMx). The techniques work described herein may lead to alternative and adjunct techniques for traditional correlation-based methods for cerebral autoregulation. The method, for example, could prove useful for the determination of PRx where some studies have reported difficulties in differentiating between intact and impaired regimes exhibiting very small difference (typically a PRx value as small as 0.2 is associated with dysautoregulation, compared to 0.0 for intact autoregulation).

There are other COx analysis methods based on data clustering. For example, Table 3 compares a Gaussian mixture model (GMM) data clustering approach with the gradient adjustment method. The GMM method also successfully produced LLAs for all eight data sets, and the GMM method produced results very similar to the automated GACOx method, with a RMSD (root mean square of the difference) of 3.4 mmHg between both algorithms. However, the GMM method may be much more complex than the proposed gradient adjusted algorithm which, after gradient adjustment, requires only a simple threshold of zero to differentiate between intact and impaired zone data.

TABLE 3

Comparison of gradient adjustment and data clustering approaches for LLA determination.

| Method | p01 | p02 | p03 | p04 | p05 | p06 | p07 | p08 |
| --- | --- | --- | --- | --- | --- | --- | --- | --- |
| GACOx algorithm | 50 | 40 | 65 | 45 | 45 | 45 | 50 | 60 |
| GMM algorithm | 42 | 43 | 67 | 47 | 42 | 45 | 52 | 60 |

The intact region may display a positive slope and may therefore be a confounder to the traditional correlation-based COx approach. Moreover, distinct (paradoxical) negative slopes may also be observed in intact regions for cardiac surgery patients. In this instance, the traditional COx method may tend to produce values at +1 and −1 for the impaired and intact regions respectively and hence the gradient adjustment method described herein may not be necessary (although it could still prove useful in accentuating the difference in noisy data).

Application of the GACOx method to a real-time algorithm may include a sufficient number of points to establish a linear fit with statistical meaning. A minimum number of points spanning through a range of blood pressures may be needed for the method to be able to discern the main autoregulation function regions.

An aspect of the techniques of this disclosure may be based on data in both the impaired and intact regions to successfully alter the gradient so that the intact region after gradient adjustment is of a negative slope. This may not always be a problem, especially where an entire data set is analyzed retrospectively. However, in practice, in order to develop a real-time implementation, this issue may arise. As the COx curve is built up, the data may initially only be confined to one region (intact or impaired). In this case, gradient adjustment could, for example, be based on a historical knowledge of the expected gradients of impaired and intact regions.

Some of the examples above may have considered only the determination of the LLA. However, the processing circuitry described herein may alternatively or additionally be configured in accordance with the techniques of this disclosure to better determine the ULA. For example, the processing circuitry may be configured to determine a position of the ULA by determining an MAP value that is higher than the LLA at which the associated value of GACOx exceeds a threshold value, such as 0.3, 0.5, or 0.7, for example. FIGS. 4A and 4B show examples of an LLA and a ULA determined from the MAP and $rSO_2$ data.

However, real data can behave in a much more complex way than the traditional Lassen curve indicates, with both positive and negative correlations having been observed in practice between $rSO_2$ and MAP during intact autoregulation regimes. In some examples, the proposed gradient adjustment technique may be simple to implement and may significantly aid in the automatic extraction of the limits of autoregulation. An aspect of the techniques of this disclosure can be successfully applied to a pig study, with noticeable improvement in terms of successfully determining lower limit boundaries of autoregulation with values very close to those determined by manual inspection. Some aspects of the techniques of this disclosure may allow for automatically and robustly identifying of the limits of autoregulation.

Returning to FIG. 1D, the COx values have been plotted against MAP. The COx plot may exhibit a drop in typical values when transitioning from blood pressures (BPs) below the LLA to the intact region and similarly, at higher pressures, may exhibit a step increase when transitioning from the intact region to BPs above the ULA.

In the unbinned data (see FIG. 1C), there may be a pattern of COx values clumped at 1 in the impaired regions (below LLA and above ULA) and a spread of values from −1 to +1 in the intact region. The intact region of FIG. 2 relates to the intact (middle) region of FIG. 1C—the $rSO_2$-MAP data from the intact region of FIG. 2 is what generates the COx measure in the intact region. However, the intact region of FIG. 2 may not always be flat; rather, the curve may generally resemble the graph shown in FIG. 3. But this region may exhibit a negative gradient or a positive gradient (but less than the gradient of the impaired regions). Differences in the gradient of this part of the curve may skew the COx values obtained in the intact region. In fact, if a slightly positive gradient occurs, then values of COx may tend to unity and be less distinguishable or indistinguishable from regions of impaired autoregulation. This situation is shown in FIG. 3. In this situation, the autoregulation system is intact but may appear impaired when considering the COx values because the slope is slightly positive.

In some examples, the Pearson correlation coefficient may "blow up" for a horizontal relationship between $rSO_2$ and BP. This is shown in FIG. 2. For a horizontal relationship between $rSO_2$ and BP, i.e., no relationship at all between $rSO_2$ and BP, a flat curve may occur. However, if such a curve were to occur in practice then the Pearson coefficient could not be computed. The Pearson correlation coefficient is defined in Equation (1) above.

Where cov(X,Y) is the covariance between X and Y and $\sigma_X$ is the standard deviation of X. If the curve is horizontal, then $\sigma_Y$ equals zero and hence the correlation coefficient will be infinite. Therefore, in practice, there may be noise and a relatively random non-zero Pearson coefficient to result. Both the existence of a slightly positive gradient and a zero gradient are both, therefore, problematic. A strong negative gradient with high negative COx value may not be problematic as it corresponds to paradoxical relationship well known to be associated with intact autoregulation.

An aspect of the techniques of this disclosure may significantly enhance the delineation between impaired and intact autoregulation zones in the COx plot, by manipulating the underlying relationship so that slightly positive and zero gradients can be made negative while leaving the impaired regions with positive gradients. A method of this disclosure may compensate for the different gradients of region B of FIG. 4A by applying a transform to the $rSO_2$ values before determining the correlation. The overall gradient of the whole $rSO_2$-MAP curve (m) shown in FIG. 4A may be determined and used to transform the $rSO_2$ values in the y-direction. That is, the values of the overall line of best fit are subtracted from the $rSO_2$-MAP curve.

Figure 9A:
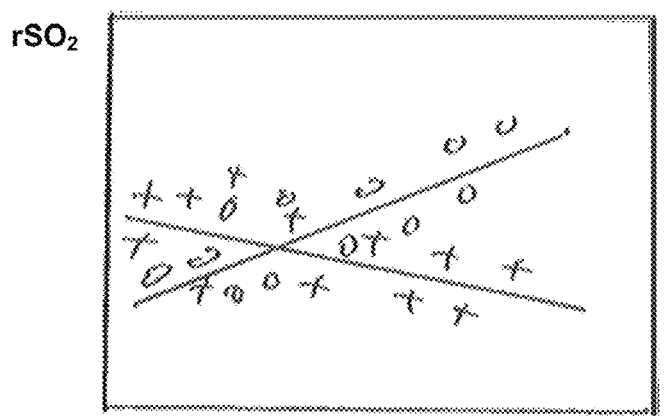
FIGS. 9A and 9B are example graphs illustrating transformed values of $rSO_2$ versus MAP for the intact region and an impaired region, in accordance with some examples of this disclosure.
Figure 9B:
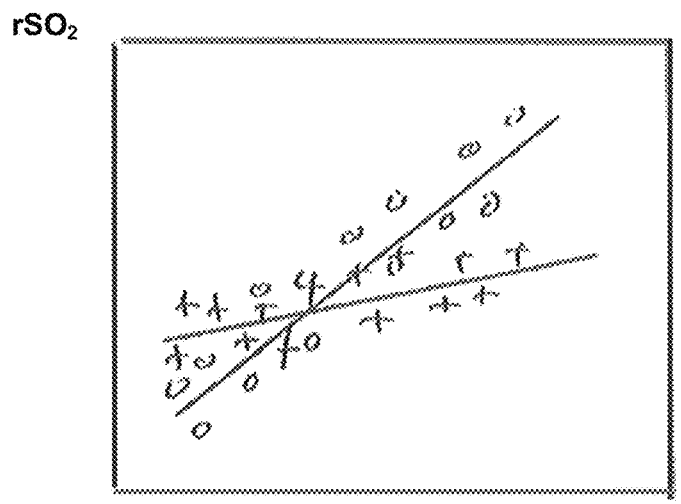

FIGS. 9A and 9B are example graphs illustrating transformed values of $rSO_2$ versus MAP for the intact region and an impaired region, in accordance with some examples of this disclosure. The overall gradient may be greater than that of region B and less than A and C, as shown in FIG. 4A. This may result in much lower (negative) correlation values in region B, while maintaining positive values in regions A and C. FIG. 9A shows the $rSO_2$-MAP data in a single COx window—the original data (marked by 'o') has a close to zero gradient corresponding to a slightly positive gradient in region B of FIG. 4A (intact autoregulation). The transformation of the data causes the sign of the gradient (and hence R) to flip, resulting in a negative COx value for the transformed data (marked by 'x'). FIG. 9B shows the process for a window with strong positive relationship (corresponding to region A or C of FIG. 4A) and should have an R value close to 1 for the original data (marked by 'o'). Shifting the y values results in the data maintaining a strong relationship, but with a slightly smaller, still positive, COx value for the transformed data (marked by 'x').

Figure 10:
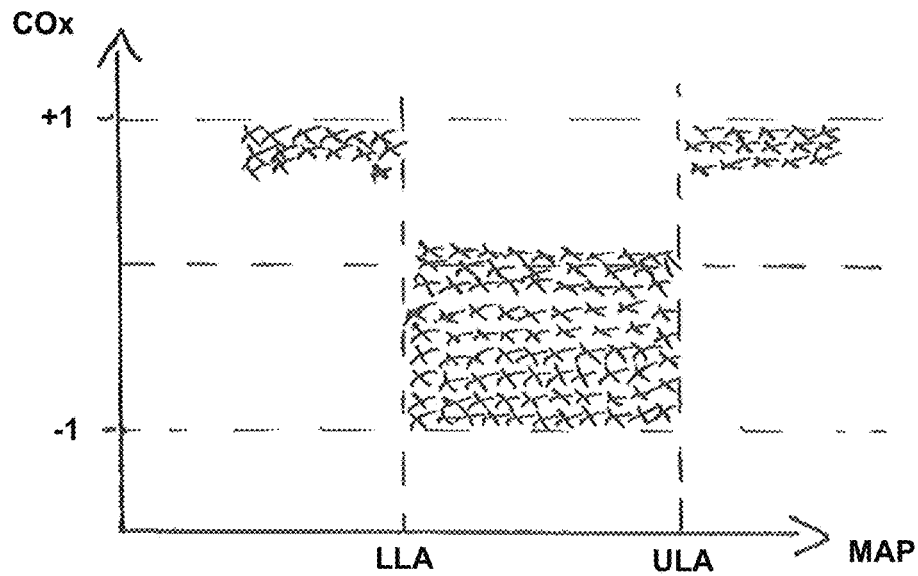
FIG. 10 is an example scatterplot of COx versus MAP, where the values of COx are based on the transformed values of $rSO_2$, in accordance with some examples of this disclosure.

FIG. 10 is an example scatterplot of COx versus MAP, where the values of COx are based on the transformed values of $rSO_2$, in accordance with some examples of this disclosure. FIG. 10 displays the transformed version of the COx versus MAP for the data of FIG. 1C: lower COx values in the intact region but values still close to +1 in the impaired regions. The scatterplot of FIG. 10 is a schematic illustrating binned data after applying a transformation function. Note that the intact region (between the LLA and the ULA) is now much lower and there is a more distinct jump in the COx values. This change in the plot enables more robust detection of the LLA and ULA points, i.e., it may now be easier to determine the blood pressures for which a person may have impaired autoregulation.

Figure 11A:
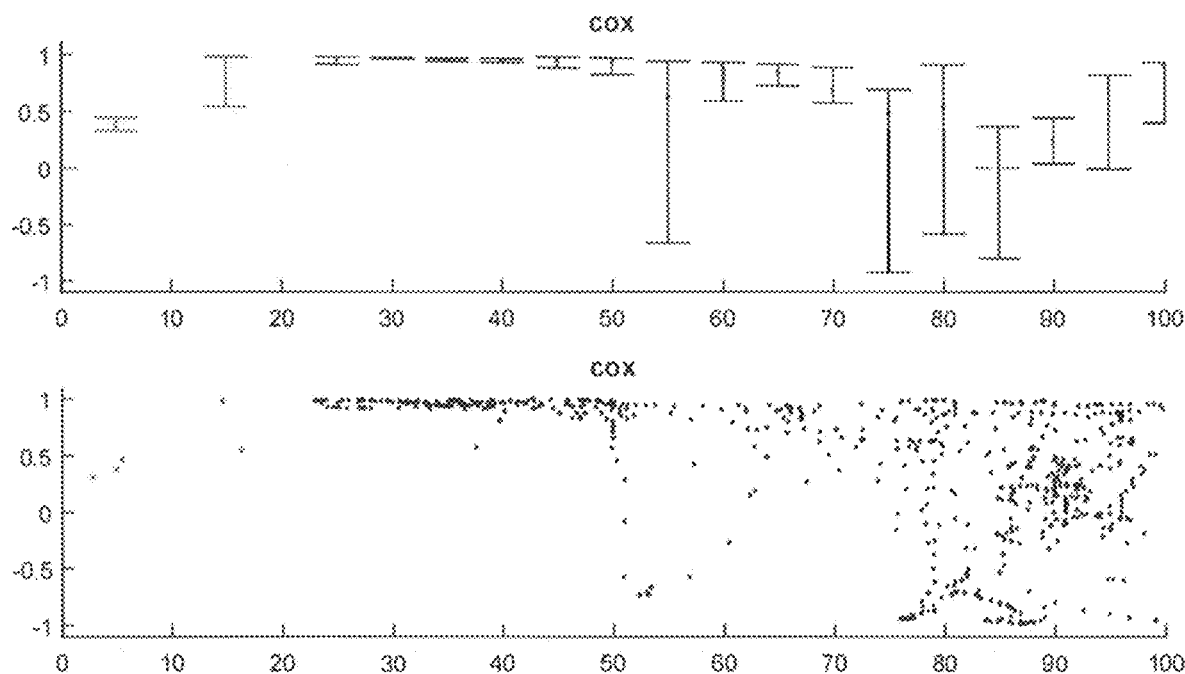
FIGS. 11A and 11B depict graphs illustrating binned and unbinned values of COx based on untransformed and transformed values of $rSO_2$, in accordance with some examples of this disclosure.
Figure 11B:
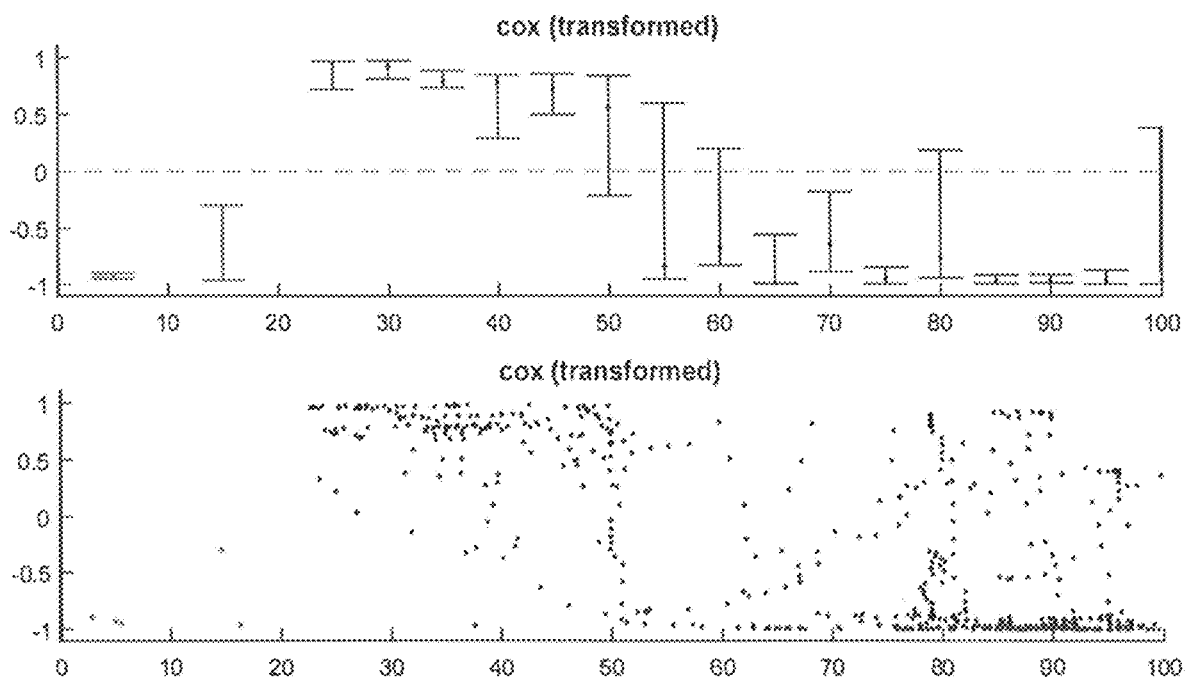

FIGS. 11A and 11B illustrate binned and unbinned values of COx based on untransformed and transformed values of $rSO_2$, in accordance with some examples of this disclosure. FIG. 11A shows the original COx data taken from a porcine model, and FIG. 11B shows the data from FIG. 11A after the transformation is applied. In each of FIGS. 11A and 11B, the top graph shows the binned data and the bottom graph shows the raw data. The plots of FIGS. 11A and 11B show the data that processing circuitry may use to determine the LLA. In some examples, the processing circuitry may also be configured to determine the ULA using the same or similar techniques.

In a method, the processing circuitry may use an average overall line (computed from historical data) before enough data from the current patient has been collected for the processing circuitry to determine a robust value for this patient. As the processing circuitry collects more data from the current patient, the processing circuitry can remove the effect of the precomputed gradient. The processing circuitry may be configured to determine an initial trendline function (e.g., a default trendline function) at the beginning of a monitoring session. As the processing circuitry determines values of the physiological parameters, the processing circuitry may be configured to reduce the effect of the initial trendline function. For example, the processing circuitry may be configured to use $$m = m_{patient} + m_{hist} \times \exp(-t/\tau) \text{ and} \quad (4)$$

$$c = c_{patient} + c_{hist} \times \exp(-t/\tau), \quad (5)$$

where $\tau$ is a decay rate, m_patient is derived from the current patient, m_hist is the precomputed value and t is the time. And m and c are the gradient and intercept of the fitted line (y=mx+c). In a method, the processing circuitry may be configured to conditionally apply or perform the transformation step, for example, when a confidence measure or a set of confidence measures are above a certain value. For example, the total number of data points used to determine the overall gradient may meet a threshold number before applying the transformation step. For example, the processing circuitry may be configured to determine the total number of data points during a monitoring session. Each data point can be associated with a MAP value, an $rSO_2$ value, and/or a COx value. In some examples, the processing circuitry is configured to determine the trendline function and the transformed values of the first physiological parameter only in response to determining that the total number of data points exceeds the threshold number.

In a method, the techniques, including gradient-adjusted oxygen saturation values and including gradient-adjusted correlation coefficient values, could be applied to other measures of autoregulation, for example, a blood volume signal, an ICP signal or a measure of flow velocity could be used in place of $rSO_2$ in order to apply this connection to HVx, PRx, or Mx.

Figure 12:
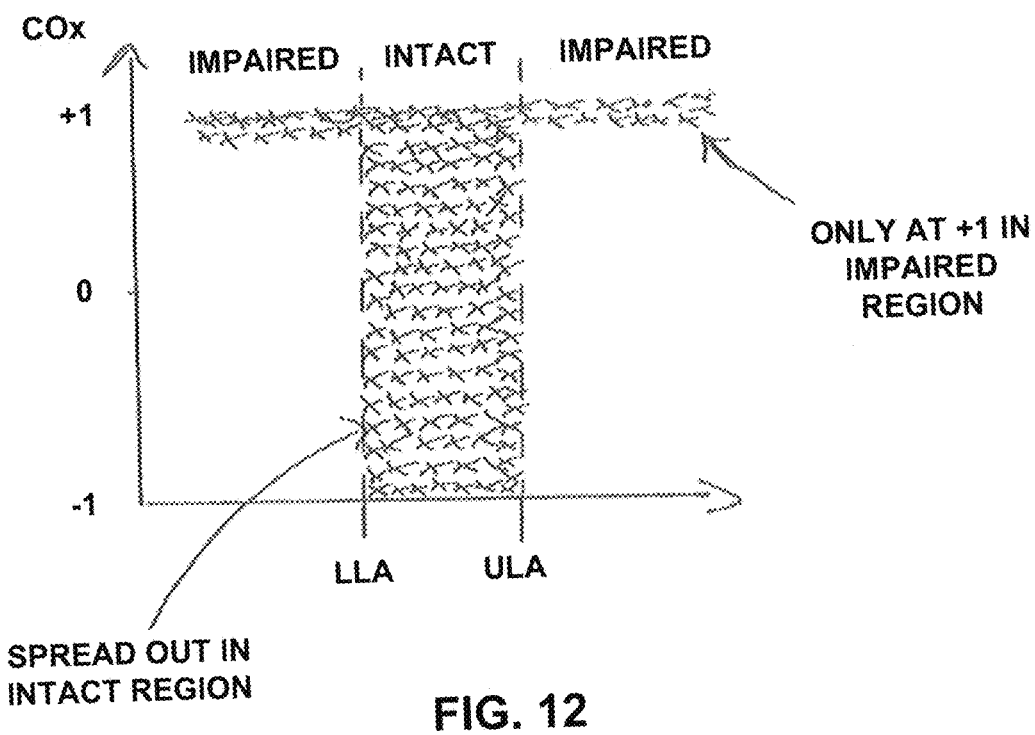
FIG. 12 is a graph illustrating untransformed values of COx in the impaired regions and the intact region, in accordance with some examples of this disclosure.

FIG. 12 illustrates untransformed values of COx in the impaired regions and the intact region, in accordance with some examples of this disclosure. One of the most prevalent ways of determining autoregulation status is using COx. COx may be determined as the Pearson Rank Coefficient between Mean Arterial Pressure (MAP) and $rSO_2$. In theory, a value of +1 may correspond to impaired autoregulation and a value of −1 to intact autoregulation. However, in practice, in the impaired regions COx may be very close to +1 and in the intact region COx may vary between +1 and −1. The COx measure may be biased towards positive values—this may mean that values of +1 are seen in both regions. This can be seen schematically in FIG. 12.

This disclosure presents a method for improving the COx measure by reweighting the values. This allows the computed COx values to be more heavily weighted towards +1 and −1 in a nonlinear fashion which makes it easier to determine the intact region. In this disclosure example results are presented for incorporating the reweighted COx measure. In a method, the COx measure may be reweighted by applying the following thresholds:

TABLE 4

Piecewise transform function to obtain modified COx.

| Original COx | Modified COx |
| --- | --- |
| Greater than Upper Threshold | +1 |
| Between Thresholds | Apply weak function |
| Below Lower Threshold | Apply strong function |

Figure 13:
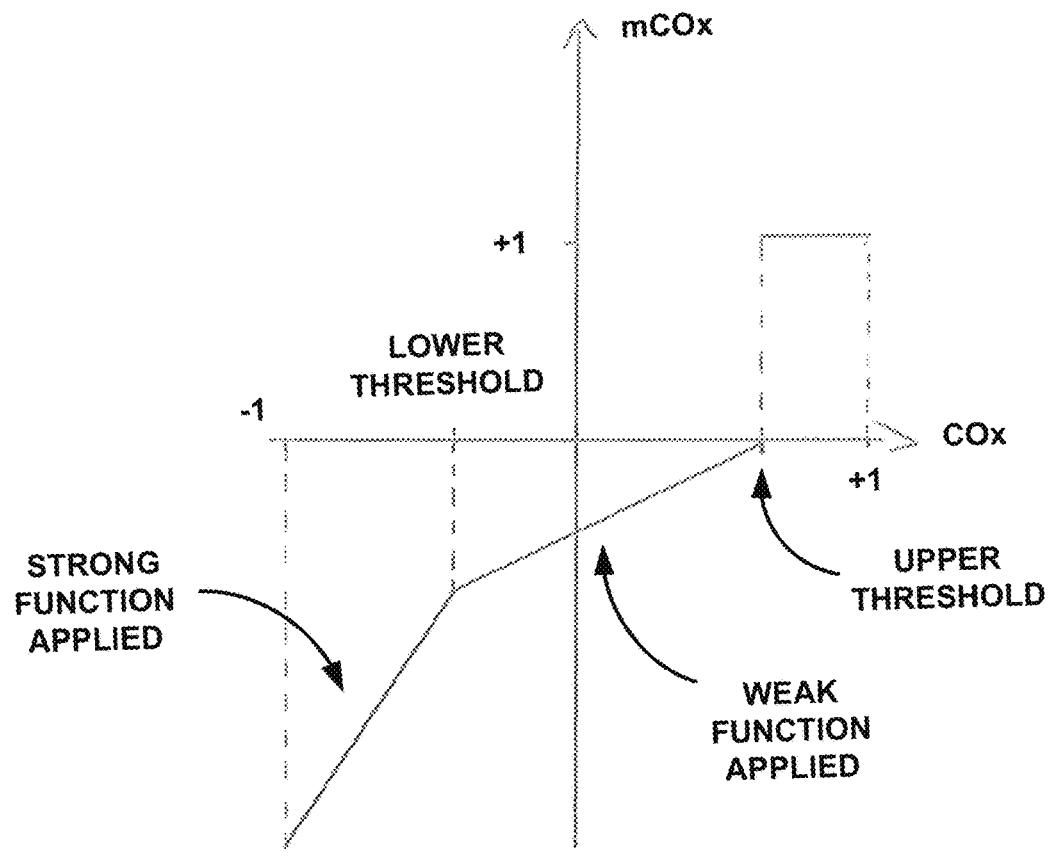
FIG. 13 is a graph illustrating the relationship between value of COx and modified COx based on a piecewise transform function for values of COx, in accordance with some examples of this disclosure.

FIG. 13 illustrates the relationship between value of COx and modified COx based on a piecewise transform function for values of COx, in accordance with some examples of this disclosure. At values of the correlation coefficient that exceed the threshold value, the modified (i.e., transformed) value may be equal to a predetermined value such as +1.0 or 0.9. The processing circuitry can use a weak function to accept the COx value and return a modified COx (mCOx) value such that the new value is considered intact. The processing circuitry may use the weak function to apply a different weighting based on the input COx value. For example, the weak function may be of the form mCOx=a*COx−(Threshold_upper), where a is some constant (see FIG. 13). This may result in a mCOx of zero at the upper threshold and a steadily more negative mCOx as COx decreases. Examples of the upper threshold may be 0.3, 0.4, 0.5, etc.

The processing circuitry can use a strong function to further downweight the COx values below a lower threshold. This strong function may be of the form mCOx=b*COx, where b>>a. Or this function may be a simple threshold i.e. mCOx=b. Example values for the lower threshold may be 0, −0.1, −0.2, −0.3, etc. FIG. 13 shows the relationship between COx and mCOx when such a scheme is applied.

Figure 14A:
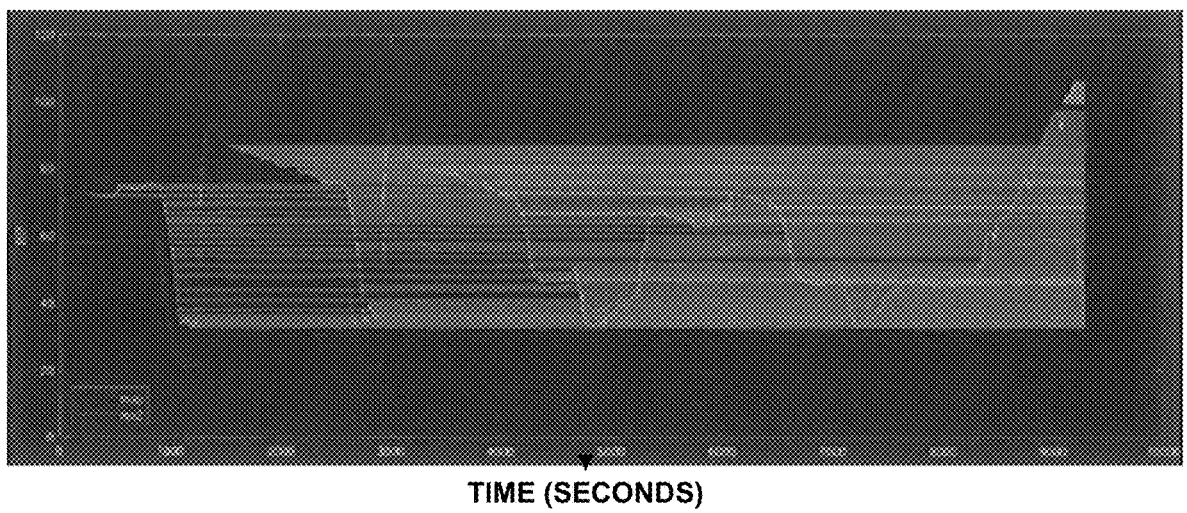
FIGS. 14A-14C are graphs illustrating blood pressure over time, showing the LLA based on values of COx and modified COx, in accordance with some examples of this disclosure.
Figure 14B:
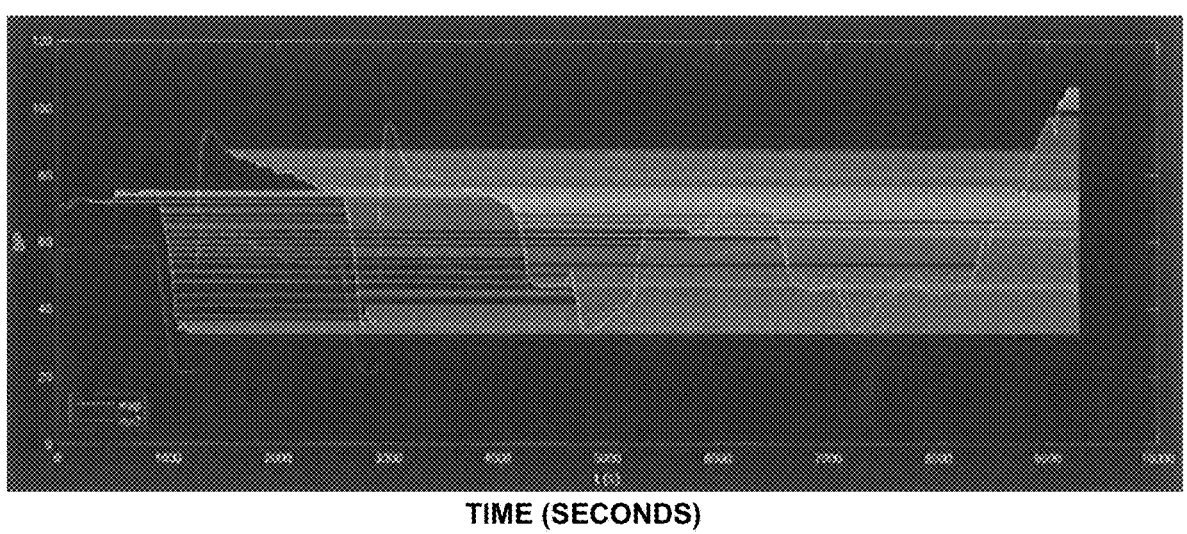
Figure 14C:
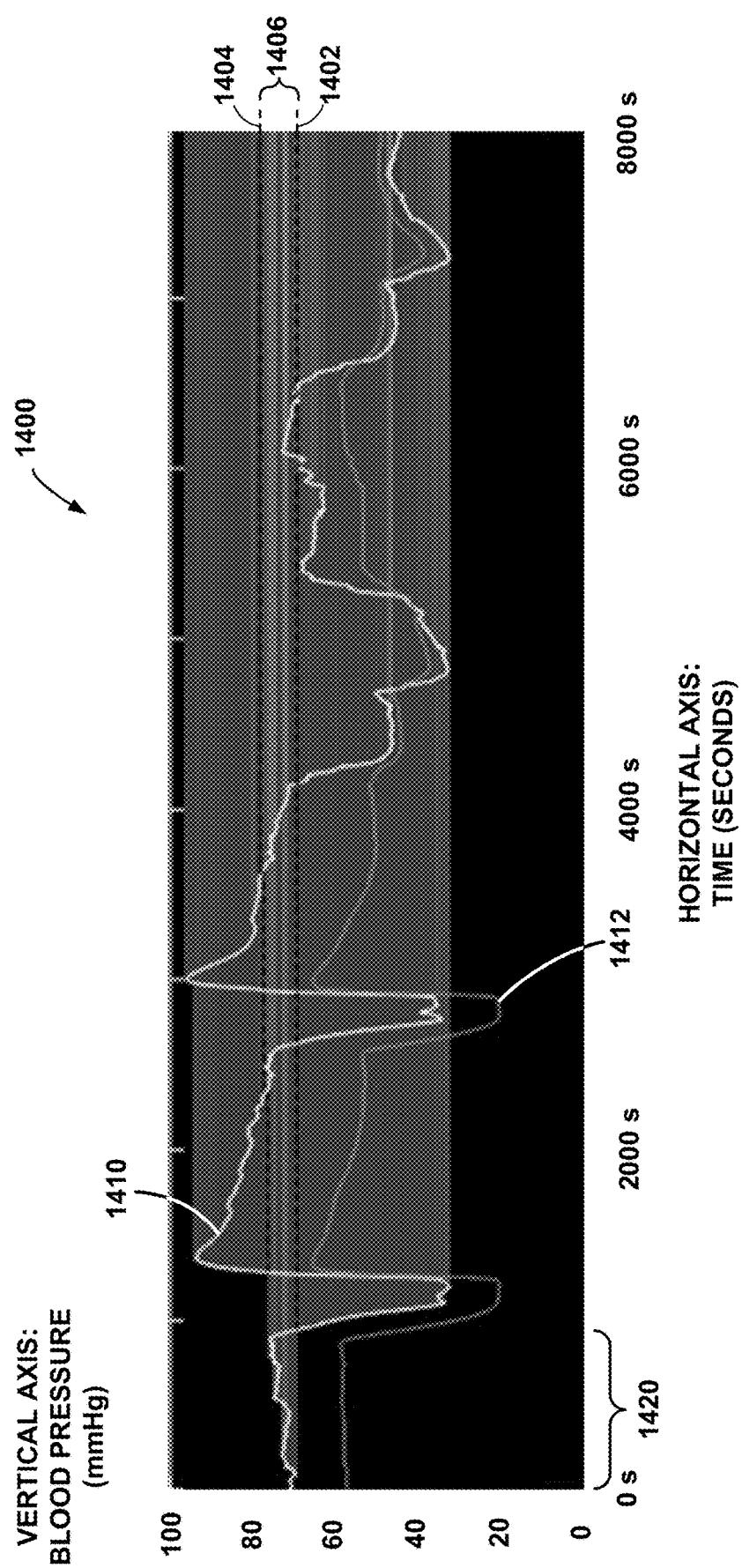

FIGS. 14A-14C are graphs illustrating blood pressure over time, showing the improvement in the identification of the intact zone of autoregulation through the use of the modified COx, in accordance with some examples of this disclosure. For the processing circuitry to identify the intact zone of autoregulation, the processing circuitry may be configured to determine the LLA and/or the ULA. FIG. 14A shows a method with COx and FIG. 14B shows a method with mCOx. FIG. 14B depicts a band with different shading, which corresponds to the intact region. The method much more readily identifies the intact region.

FIG. 14C is a graph 1400 illustrating blood pressure over time along with the lower and upper limits of cerebral autoregulation 1402 and 1404 (e.g., LLA 1402 and ULA 1404), in accordance with some examples of this disclosure. Graph 1400 is an example of a presentation of limits of cerebral autoregulation 1402 and 1404 and a cerebral autoregulation status by processing circuitry 1710 or 1714 via display 1715 or 2132. Processing circuitry 1710 can also present graph 1400 on, e.g., graphical user interface 2200.

Processing circuitry 1710 can generate and present graph 1400 to show blood pressure line 1410 of a patient over time, along with the estimates of the limits of cerebral autoregulation 1402 and 1404. Processing circuitry 1710 can also generate oxygen saturation line 1412 of the patient over time. Processing circuitry 1710 can also present an indication of cerebral autoregulation status in graph 1400 by, for example, presenting blood pressure line 1410 between or outside of LLA 1402 and ULA 1404. Intact area of cerebral autoregulation 1406 exists between LLA 1402 and ULA 1404.

In some examples, processing circuitry 1710 is configured to present intact area of cerebral autoregulation 1406 between LLA 1402 and ULA 1404 as a green color (e.g., an intact region of cerebral autoregulation). Processing circuitry 1710 can also present the region of graph 1400 above ULA 1404 and the region below LLA 1402 as red colors (e.g., impaired regions of cerebral autoregulation) which may or may not be different shades of red, for example. In response to determining a change in the relationship between a blood pressure and another physiological parameter of a patient, processing circuitry 1710 can move the lines associated with LLA 1402 and/or ULA 1404. Therefore, intact area of cerebral autoregulation 1406 may change position up or down and/or change the size.

In some examples, processing circuitry 1710 is configured to present an indication of the cerebral autoregulation status as a color, such as green or red. Processing circuitry 1710 may present the color on a graphical user interface such as graph 1400 or graphical user interface 2200 shown in FIG. 22. Processing circuitry 1710 may be configured to change the intensity of the color(s) in response to determining a change in a limit of cerebral autoregulation. Processing circuitry 1710 can change the intensity of the color based on the magnitude of the determined change in the limit of cerebral autoregulation. For example, in response to determining a relatively large change in a limit of cerebral autoregulation, processing circuitry 1710 may significantly reduce the intensity of the green color presented in intact area of cerebral autoregulation 1406. The less intense green color may indicate lower confidence in the estimates of limits of cerebral autoregulation 1402 and 1404.

Graph 1400 depicts LLA 1402 and ULA 1404 at approximately 68 and 75 mmHg, respectively. In response to determining that blood pressure line 1410 has a value between 68 and 75 mmHg, processing circuitry 1710 may present an indication of an intact cerebral autoregulation status, such as blood pressure line 410 within an area of green color between LLA 1402 and ULA 1404. Processing circuitry 1710 may also present an indication of the intact cerebral autoregulation status such as text (e.g., "autoregulation: intact").

Time period 1420 (e.g., the first eight hundred seconds) does not include an indication of LLA 1402 or ULA 1404 because processing circuitry 1710 may not yet have obtained sufficient data to determine LLA 1402 or ULA 1404. When blood pressure line 1410 drops below 60 mmHg, processing circuitry 1710 determines and presents LLA 1402 on graph 1400. When blood pressure line 1410 increases above 80 mmHg, processing circuitry 1710 determines and presents ULA 1404 on graph 1400.

Figure 15:
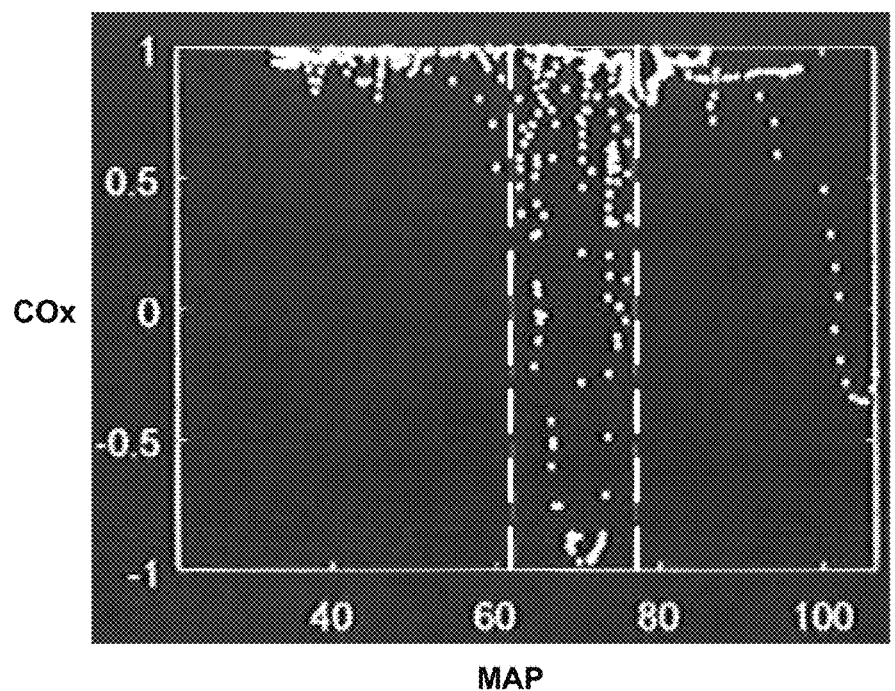
FIG. 15 is a graph illustrating values of COx versus measurements of MAP, in accordance with some examples of this disclosure.

FIG. 15 is a graph illustrating values of COx versus measurements of MAP, in accordance with some examples of this disclosure. FIG. 15 shows the standard COx curve with the white dashed lines demarcating the LLA and ULA found from FIG. 14B.

In a method, mCOx may be determined and used for the identification of the intact and impaired regions but never shown on the display—the original COx may be shown instead. In a method, additional functions may be applied when determining mCOx. For example, if COx>Threshold_upper, then we may measure the spread of the COx values at this blood pressure. If the values are spread out, then mCOx may be set to −1 and if the values are clustered near +1 at this blood pressure, then mCOx may be set to +1. For example, an entropy measure may be used.

Figure 16:
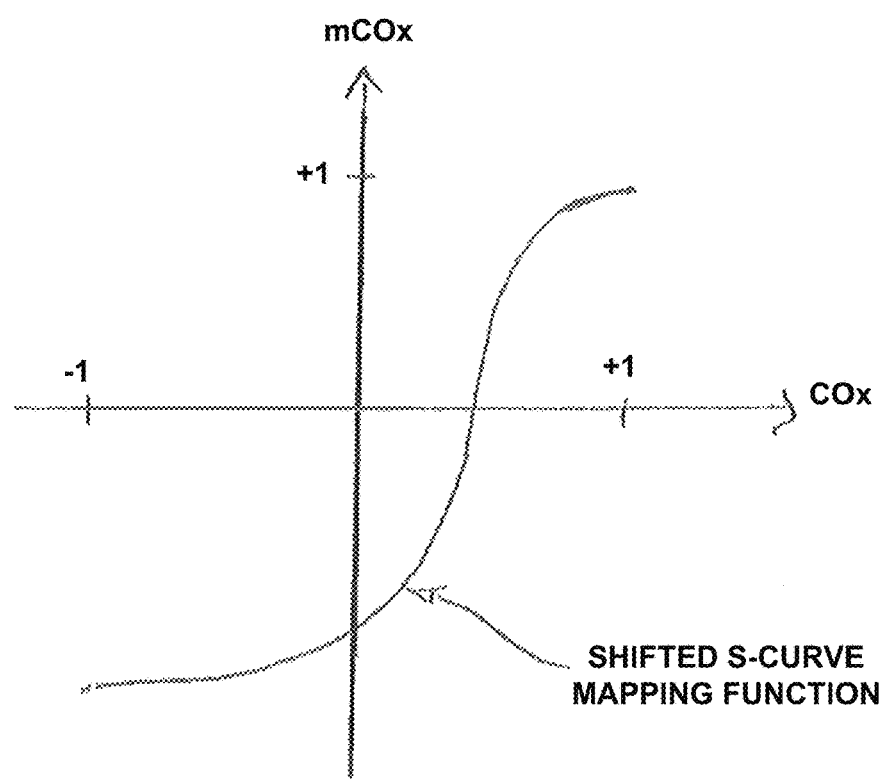
FIG. 16 is a graph illustrating a continuous transform function for values of COx, in accordance with some examples of this disclosure.

FIG. 16 illustrates a continuous transform function for values of COx, in accordance with some examples of this disclosure. In a method, no thresholds may be employed but rather a continuous mapping curve used. This is shown schematically in FIG. 16 as a shifted "S-curve" shape. In a method, the functional mapping (continuous or piece-wise) from COx to mCOx may be derived from historical data through trial and error iterations to determine the optimum mapping. In a method, the remapping may be applied to other con-elation based measures of autoregulation, such as HVx, Mx, and PRx.

Figure 17:
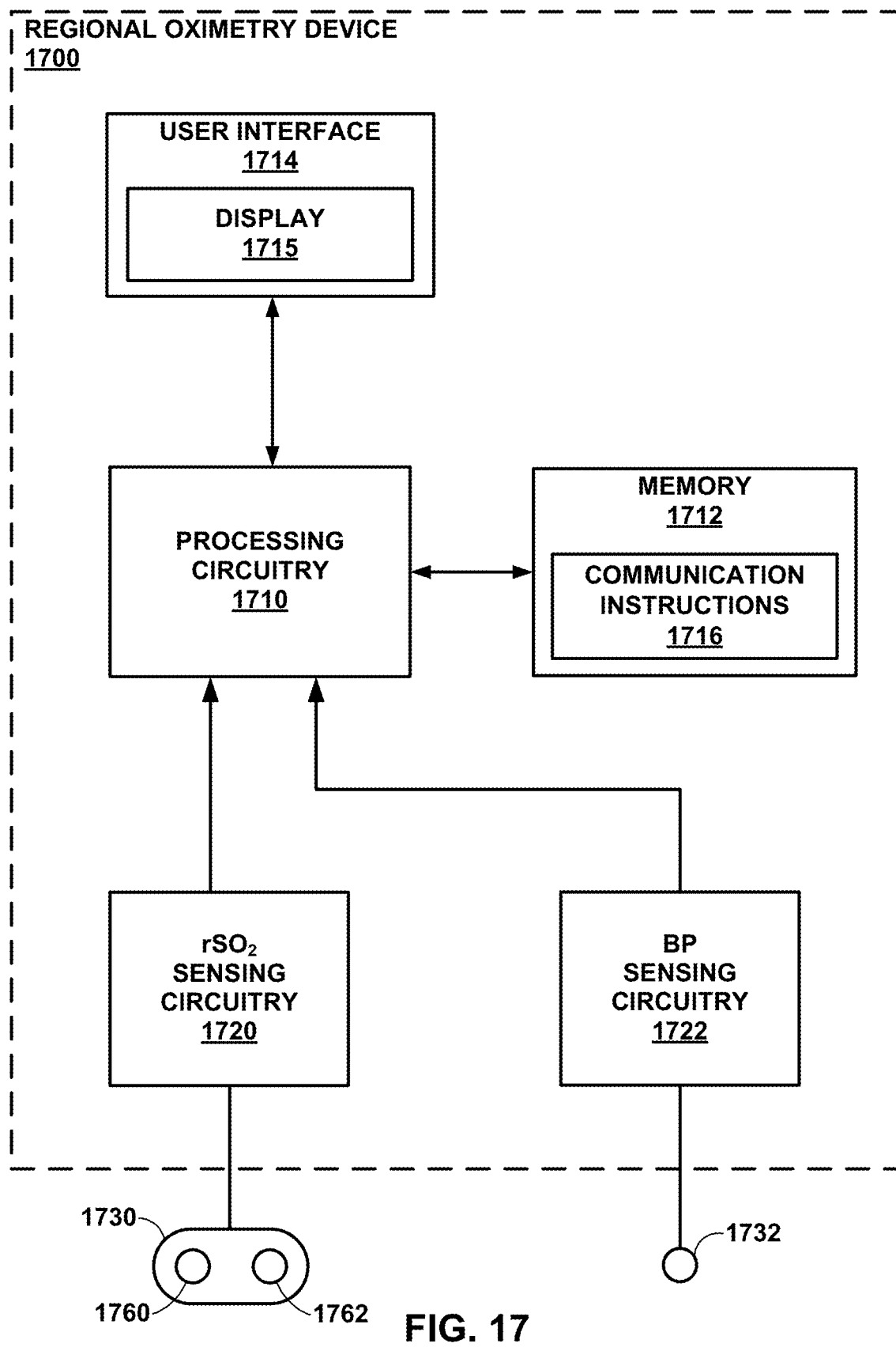
FIG. 17 is a conceptual block diagram of a device configured to determine limit(s) of autoregulation, in accordance with some examples of this disclosure.

FIG. 17 shows a conceptual block diagram of a regional oximetry device 1700 configured to determine limit(s) of autoregulation, such as an LLA and/or the ULA, in accordance with some examples of this disclosure. Regional oximetry device 1700 may include processing circuitry 1710, memory 1712, user interface 1714, rSO$_2$ sensing circuitry 1720, blood pressure (BP) sensing circuitry 1722, and sensing devices 1730 and 1732. In some examples, regional oximetry device 1700 may be configured to determine and display an LLA and/or the ULA of a patient during a medical operation, such as surgery, or fetal monitoring. A clinician may receive information regarding the LLA and/or the ULA via display 1715 and adjust treatment or therapy to the patient based on the cerebral autoregulation status information.

Processing circuitry 1710, as well as other processors, processing circuitry, controllers, control circuitry, and the like, described herein, may include one or more processors. Processing circuitry 1710 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 1710 may include multiple components, such as any combination of one or more microprocessors, one or more DSPs, one or more ASICs, or one or more FPGAs, as well as other discrete or integrated logic circuitry, and/or analog circuitry.

Example operations described above with respect to "processing circuitry" may be performed by processing circuitry 1710, in various examples. In some examples, processing circuitry 1710 may be configured to perform some or all of the operations of FIGS. 18-20. For example, processing circuitry 1710 may be configured to receive signals indicating measurements of physiological parameters from sensing circuitry 1720 and/or 1722. The physiological parameters may include blood pressure (e.g., mean arterial pressure) and regional oxygen saturation. In some examples, processing circuitry 1710 may be configured to determine a trendline function, which may include a gradient, based on the measurements of the physiological parameters. Processing circuitry 1710 may be configured to determine a transform function (see, e.g., FIGS. 4A and 4B) based on the trendline function and to apply a transform function to the measurements of the physiological parameters, as described herein.

Processing circuitry 1710 may be configured to determine cerebral oximetry indices based on the measured values of the physiological parameters or the transformed values of the physiological parameters. In some examples, processing circuitry 1710 may be configured to apply a second transform function (see, e.g., FIGS. 13 and 16) to the values of COx to determine transformed values of COx. Processing circuitry 1710 may be then configured to determine an LLA and/or a ULA based on the original values of COx or the transformed values of COx. Processing circuitry 1710 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 1710 may include multiple components, such as any combination of one or more microprocessors, one or more DSPs, one or more ASICs, or one or more FPGAs, as well as other discrete or integrated logic circuitry, and/or analog circuitry.

Memory 1712 may be configured to store measurements of physiological parameters, values of COx, and value(s) of an LLA and/or a ULA, for example. Memory 1712 may be configured to store data such as default gradients for a trendline function. Processing circuitry 1710 may be configured to use a default gradient to determine a transform function if processing circuitry 1710 has not received sufficient data to determine a gradient. In some examples, memory 1712 may store program instructions, such as communication instructions 1716, which may include one or more program modules, which are executable by processing circuitry 1710. When executed by processing circuitry 1710, such program instructions may cause processing circuitry 1710 to provide the functionality ascribed to it herein. The program instructions may be embodied in software, firmware and/or RAMware. Memory 1712 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 1714 may include display 1715 that displays the LLA and/or the ULA to a user. User interface 1714 and/or display 1715 may be configured to present a graphical user interface to a user, where each graphical user interface may include indications of values of one or more physiological parameters of a patient. For example, processing circuitry 1710 may be configured to present blood pressure values, physiological parameter values, and indications of autoregulation status (e.g., cerebral autoregulation status) of a patient via display 1715. In some examples, if processing circuitry 1710 determines that the autoregulation status of the patient is impaired, then processing circuitry 1710 may present a notification (e.g., an alert) indicating the impaired cerebral autoregulation status via display 1715. As another example, processing circuitry 1710 may present, via display 1715, estimates of $rSO_2$ for a patient, an estimate of the blood oxygen saturation ($SpO_2$) determined by processing circuitry 1710, pulse rate information, respiration rate information, blood pressure, any other patient parameters, or any combination thereof.

User interface 1714 and/or display 1715 may include a monitor, cathode ray tube display, a flat panel display such as a liquid crystal (LCD) display, a plasma display, a light emitting diode (LED) display, and/or any other suitable display. User interface 1714 and/or display 1715 may be part of a personal digital assistant, mobile phone, tablet computer, laptop computer, any other suitable computing device, or any combination thereof, with a built-in display or a separate display. User interface 1714 may also include means for projecting audio to a user, such as speaker(s). Processing circuitry 1710 may be configured to present, via user interface 1714, a visual, audible, tactile, or somatosensory notification (e.g., an alarm signal) indicative of the patient's autoregulation status and/or a notification indicative of the patient's limit(s) of autoregulation.

User interface 1714 may include or be part of any suitable device for conveying such information, including a computer workstation, a server, a desktop, a notebook, a laptop, a handheld computer, a mobile device, or the like. In some examples, processing circuitry 1710 and user interface 1714 may be part of the same device or supported within one housing (e.g., a computer or monitor). In other examples, processing circuitry 1710 and user interface 1714 may be separate devices configured to communicate through a wired connection or a wireless connection (e.g., communication interface 2190 shown in FIG. 21).

In some examples, display 1715 may be outside of regional oximetry device 1700, such as a tablet, smartphone, or computer monitor. User interface 1714 may be configured to display other data such as physiological parameters, COx values, and/or any other suitable data. In some examples, user interface 1714 may be configured to receive user input via a touchscreen, a keypad, or other mechanism for receiving input from a user. In some examples, regional oximetry device 1700 may include telemetry circuitry (not shown) for communicating wirelessly with one or more devices external to regional oximetry device 1700. Any appropriate communication protocols beyond RF communication may be used.

Sensing circuitry 1720 and 1722 may be configured to receive signals indicating physiological parameters from sensing devices 1730 and 1732 and communicate the physiological signals to processing circuitry 1710. Sensing device(s) 1730 and 1732 may include any sensing hardware configured to sense a physiological parameter of a patient, such as, but not limited to, one or more electrodes, optical receivers, blood pressure cuffs, or the like. Sensing circuitry 1720 and 1722 may be configured to convert the signals from sensing devices 1730 and 1732 to usable signals for processing circuitry 1710, such that processing circuitry 1710 is configured to receive signals generated by sensing circuitry 1720 and 1722. Sensing circuitry 1720 and 1722 may receive signals indicating physiological parameters from a patient, such as, but not limited to, blood pressure, regional oxygen saturation, blood volume, heart rate, and respiration. Sensing circuitry 1720 and 1722 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 1720 and 1722 and/or processing circuitry 1710 may include signal processing circuitry such as an analog to digital converter. Sensing devices 1730 and 1732 may include one or more electrodes, for example.

In some examples, oxygen saturation sensing device 1730 is a regional oxygen saturation sensor configured to generate an oxygen saturation signal indicative of blood oxygen saturation within the venous, arterial, and/or capillary systems within a region of the patient. For example, oxygen saturation sensing device 1730 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 1730 may include emitter 1760 and detector 1762. Emitter 1760 may include at least two light emitting diodes (LEDs), each configured to emit at different wavelengths of light, e.g., red or near infrared light. In some examples, light drive circuitry (e.g., within sensing device 1730, sensing circuitry 1720, and/or processing circuitry 1710) may provide a light drive signal to drive emitter 1760 and to cause emitter 1760 to emit light. In some examples, the LEDs of emitter 1760 emit light in the wavelength range of about 600 nanometers (nm) to about 1000 nm. In a particular example, one LED of emitter 1760 is configured to emit light at a wavelength of about 730 nm and the other LED of emitter 1760 is configured to emit light at a wavelength of about 810 nm. Other wavelengths of light may also be used in other examples.

Detector 1762 may include a first detection element positioned relatively "close" (e.g., proximal) to emitter 1760 and a second detection element positioned relatively "far" (e.g., distal) from emitter 1760. Light intensity of multiple wavelengths may be received at both the "close" and the "far" detector 1762. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 1730 may provide the regional oxygen saturation signal to processing circuitry 1710 or to any other suitable processing device to enable evaluation of the patient's autoregulation status.

In operation, blood pressure sensing device 1732 and oxygen saturation sensing device 1730 may each be placed on the same or different parts of the patient's body. For example, blood pressure sensing device 1732 and oxygen saturation sensing device 1730 may be physically separate from each other and may be separately placed on the patient. As another example, blood pressure sensing device 1732 and oxygen saturation sensing device 1730 may in some cases be part of the same sensor or supported by a single sensor housing. For example, blood pressure sensing device 1732 and oxygen saturation sensing device 1730 may be part of an integrated oximetry system configured to non-invasively measure blood pressure (e.g., based on time delays in a PPG signal) and regional oxygen saturation. One or both of blood pressure sensing device 1732 or oxygen saturation sensing device 1730 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 1700 is shown in FIG. 17, the components illustrated in FIG. 17 are not intended to be limiting. Additional or alternative components and/or implementations may be used in other examples.

Blood pressure sensing device 1732 may be any sensor or device configured to obtain the patient's blood pressure (e.g., arterial blood pressure). For example, blood pressure sensing device 1732 may include a blood pressure cuff for non-invasively monitoring blood pressure or an arterial line for invasively monitoring blood pressure. In certain examples, blood pressure sensing device 1732 may include one or more pulse oximetry sensors. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 1732 may be configured to generate a blood pressure signal indicative of the patient's blood pressure (e.g., arterial blood pressure) over time. Blood pressure sensing device 1732 may provide the blood pressure signal to sensing circuitry 1722, processing circuitry 1710, or to any other suitable processing device to enable evaluation of the patient's autoregulation status.

Processing circuitry 1710 may be configured to receive one or more signals generated by sensing devices 1730 and 1732 and sensing circuitry 1720 and 1722. The physiological signals may include a signal indicating blood pressure, a signal indicating oxygen saturation, and/or a signal indicating blood volume of a patient (e.g., an isosbestic signal). Processing circuitry 1710 may be configured to determine a set of values of a first physiological parameter and a set of values of a second physiological parameter based on two or more signals received by sensing devices 1730 and 1732 and sensing circuitry 1720 and 1722 and delivered to processing circuitry 1710. Sensing devices 1730 and 1732 and sensing circuitry 1720 and 1722 can deliver the physiological signals directly to processing circuitry 1710 or sensing circuitry 1720 and 1722 can modify the physiological signals (e.g., through pre-processing) before delivering signals to processing circuitry 1710. The first and second physiological parameters may include mean arterial pressure, oxygen saturation, and/or blood volume. Processing circuitry 1710 may associate each value in a set of values with a point in time. For example, processing circuitry 1710 may determine a value of mean arterial pressure at a particular time based on the characteristics of a blood pressure signal over a time interval.

Processing circuitry 1710 may be configured to determine a set of correlation coefficient values for the set of values of the first physiological parameter and for the set of values of the second physiological parameter. Processing circuitry 1710 may determine each correlation coefficient value for a sample of the values of the first physiological parameter and for a sample of the values of the second physiological parameter. For example, processing circuitry 1710 may determine each correlation coefficient value based on a Pearson coefficient that measures the strength and direction of a linear relationship between the values of the first physiological parameter and for a sample of the values of the second physiological parameter.

Processing circuitry 1710 may be configured to determine transformed values of the first physiological parameter and then determine correlation coefficient values based on the transformed values of the first physiological parameter and untransformed values of the second physiological parameter. Processing circuitry 1710 can determine transformed values of the first physiological parameter at least in part by determining a trendline function (see, e.g., FIGS. 4A and 4B) based on the values of the physiological parameters. For example, the trendline function may be a linear function, a polynomial function, an exponential function, a trigonometric function, a continuous function, a piecewise function, and/or any other suitable type of function. Processing circuitry 1710 can determine the trendline function using a best-fit algorithm to minimize the differences between the values of the first physiological parameter and the trendline function.

To transform the values of the first physiological parameter, processing circuitry 1710 may be configured to subtract each value of the first physiological parameter from the associated value along the trendline function. The difference between a value of the first physiological parameter and the associated value along the trendline function may be referred to as a gradient-adjusted value of the first physiological parameter (e.g., $GArSO_2$ or GAMAP) in some examples.

In some examples, processing circuitry 1710 is configured to determine correlation coefficient values based on the (transformed or untransformed) values of the physiological parameters. Processing circuitry 1710 may determine transformed correlation coefficient values using a transform function, which may be a linear function, a polynomial function, an exponential function, a trigonometric function, a continuous function, a piecewise function, and/or any other suitable type of function (see, e.g., FIGS. 13 and 16).

Using transformed values of a physiological parameter and/or transformed correlation coefficient values, processing circuitry 1710 may more accurately determine a limit of autoregulation. The transformation of values of a physiological parameter and/or correlation coefficient values may create a more distinct representation of a limit of autoregulation. For example, the graph shown in FIG. 6 shows how, by transforming the values of a physiological parameter, processing circuitry 1710 can create a more distinct representation of the lower limit of autoregulation. The graphs of FIGS. 11A, and 11B show how, by transforming correlation coefficient values, processing circuitry 1710 can create a more distinct representation of the lower limit of autoregulation.

Although other example devices, systems, and techniques are possible, processing circuitry 1710 may be configured to determine the limit of autoregulation based on COx values derived from MAP values and $rSO_2$ values. Alternatively, processing circuitry 1710 may determine the limit of autoregulation based on HVx values, BVS values, and/or $rSO_2$ values. Regional oximetry device 2100 of FIG. 21 includes additional detail on how processing circuitry 1710 can determine $rSO_2$ values based on a physiological signal received from sensing device 1730.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 1700 and 2100, processing circuitry 1710, 2110, 2114, and 2116, memories 1712 and 2120, displays 1715 and 2132, sensing circuitries 1720 and 1722, circuitries 2140 and 2145, sensing devices 1720, 1722, and 2150, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an application specific integrated circuit (ASIC), an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 1700 and 2100, processing circuitry 1710, 2110, 2114, and 2116, memories 1712 and 2120, sensing circuitries 1720 and 1722, and/or circuitries 2140 and 2145. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices 1700 and 2100, processing circuitry 1710, 2110, 2114, and 2116, memories 1712 and 2120, displays 1715 and 2132, sensing circuitries 1720 and 1722, circuitries 2140 and 2145, and/or sensing devices 1720, 1722, and 2150 may be programmed with various forms of software. The processing circuitry may be implemented at least in part as, or include, one or more executable applications, application modules, libraries, classes, methods, objects, routines, subroutines, firmware, and/or embedded code, for example. The processing circuitry may be configured to receive voltage signals, determine switching frequencies, and deliver control signals, for example.

Figure 18:
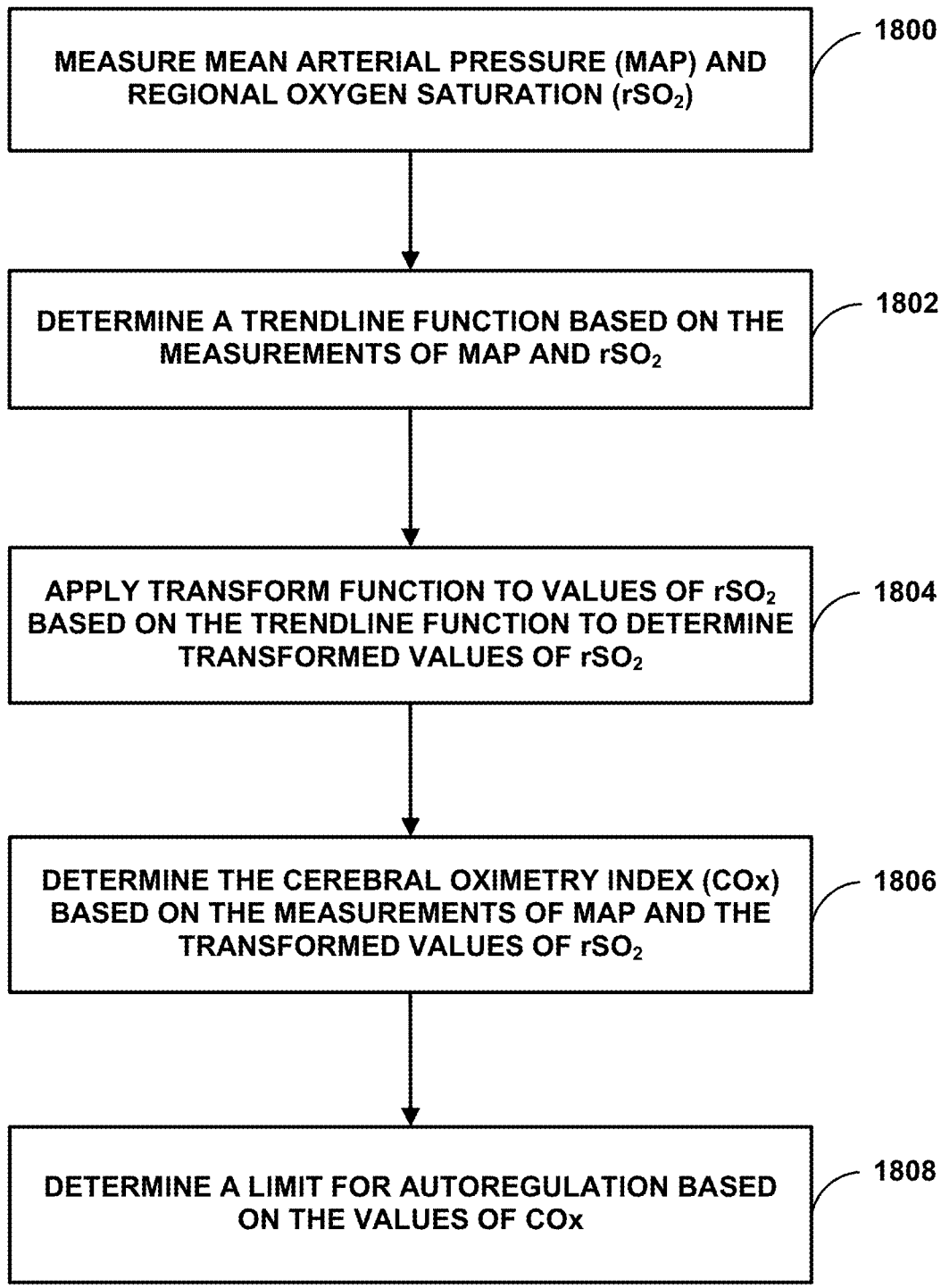
FIGS. 18 and 19 are flowcharts illustrating example techniques for determining limit(s) of autoregulation by applying a transform function to measurements of $rSO_2$, in accordance with some examples of this disclosure.

FIG. 18 is a flowchart illustrating example techniques for determining limit(s) of autoregulation such as an LLA and/or a ULA by applying a transform function to measurements of $rSO_2$, in accordance with some examples of this disclosure. In the example of FIG. 18, sensing devices 1730 and 1732 measure MAP and $rSO_2$ (1800), respectively, for a patient. The measurements may span a time duration, such as three hundred seconds, for example. In the example of FIG. 18 processing circuitry 1710 determines a trendline function based on the measurements of MAP and $rSO_2$ (1802). The trendline function may include a slope and a y-intercept for $rSO_2$.

Processing circuitry 1710 applies a transform function to values of $rSO_2$ based on the trendline function to determine transformed values of $rSO_2$ (1804). Processing circuitry 1710 may be configured to apply the transform function by subtracting the expected value of $rSO_2$ (i.e., the trendline value of $rSO_2$ for each value of MAP) from the measured value of $rSO_2$, for example. Processing circuitry 1710 determines COx values based on the measurements of MAP and the transformed values of $rSO_2$ (1806). Processing circuitry 1710 may be configured to group or bin each transformed value of $rSO_2$ with other transformed values of $rSO_2$. Each bin may span a range of MAP values, and a value of COx may be determined for each bin. Processing circuitry 1710 determines an LA based on the values of COx (1808). The processing circuitry may be configured to determine the LA by determining an LLA and/or determining a ULA. The LLA may be located at the lowest value of MAP at which the value of COx falls below a threshold, such as zero or 0.5. The ULA may be located at the highest value of MAP at which the value of COx or the value of GACOx falls below a threshold, such as zero or 0.5.

Figure 19:
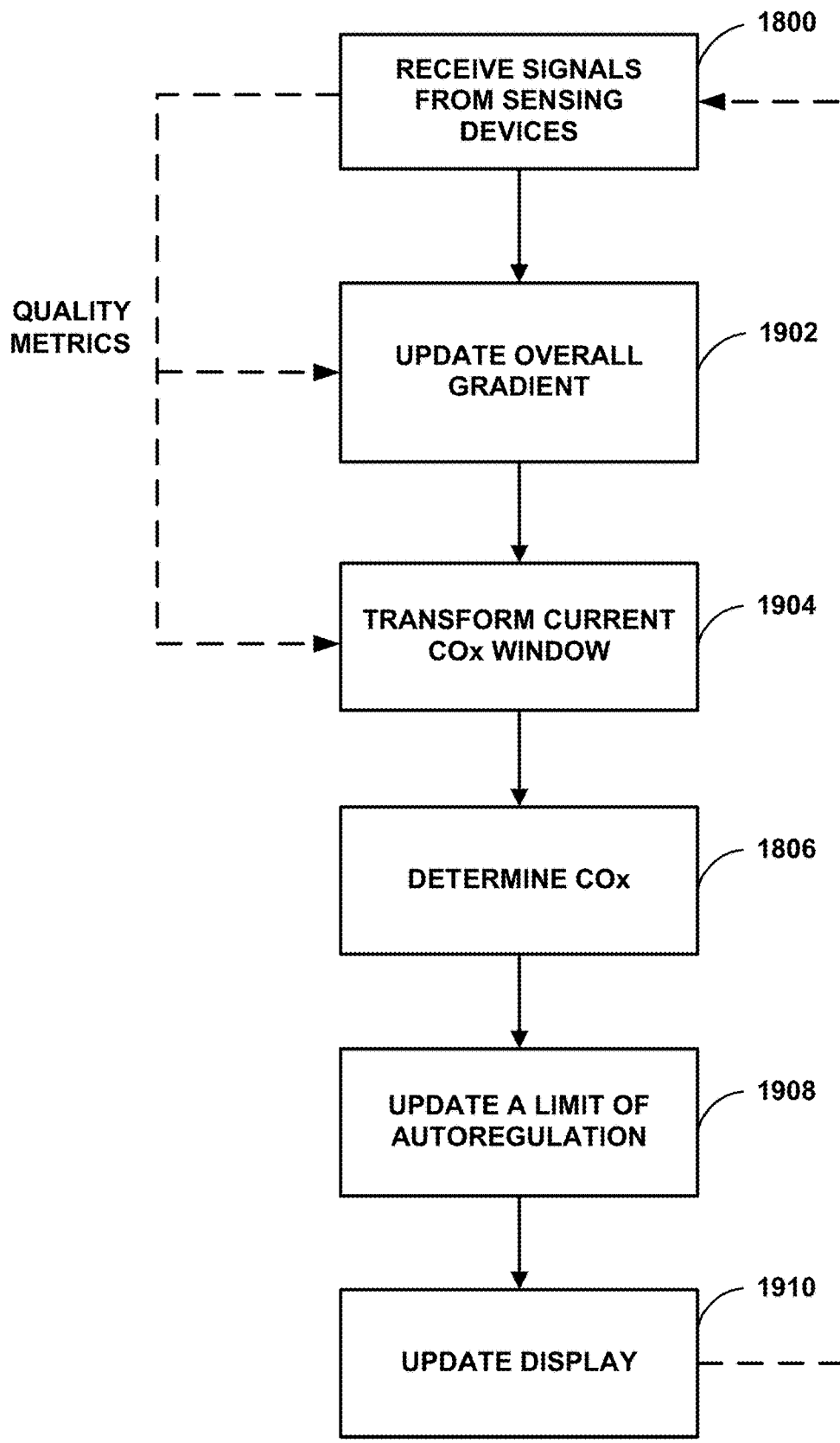

FIG. 19 is a flowchart illustrating example techniques for determining an LLA and/or a ULA by applying a transform function to measurements of $rSO_2$, in accordance with some examples of this disclosure. After receiving measurements of $rSO_2$ and MAP (1800), processing circuitry 1710 updates the overall gradient of the trendline function (1902) and transforms the current window of COx value(s) (1904). Processing circuitry 1710 may be configured to, as new $rSO_2$-MAP data becomes available, update and use the quality metrics of the LLA and/or the ULA to determine new COx value(s) (1806). Processing circuitry 1710 uses new COx value(s) to update the LA, such as the LLA and/or the ULA determination (1908). In some examples, the new COx value(s) may not cause a change in the determined value of the LLA and/or the ULA. Processing circuitry 1710 updates the display of the LLA and/or the ULA to the user (1910).

Figure 20:
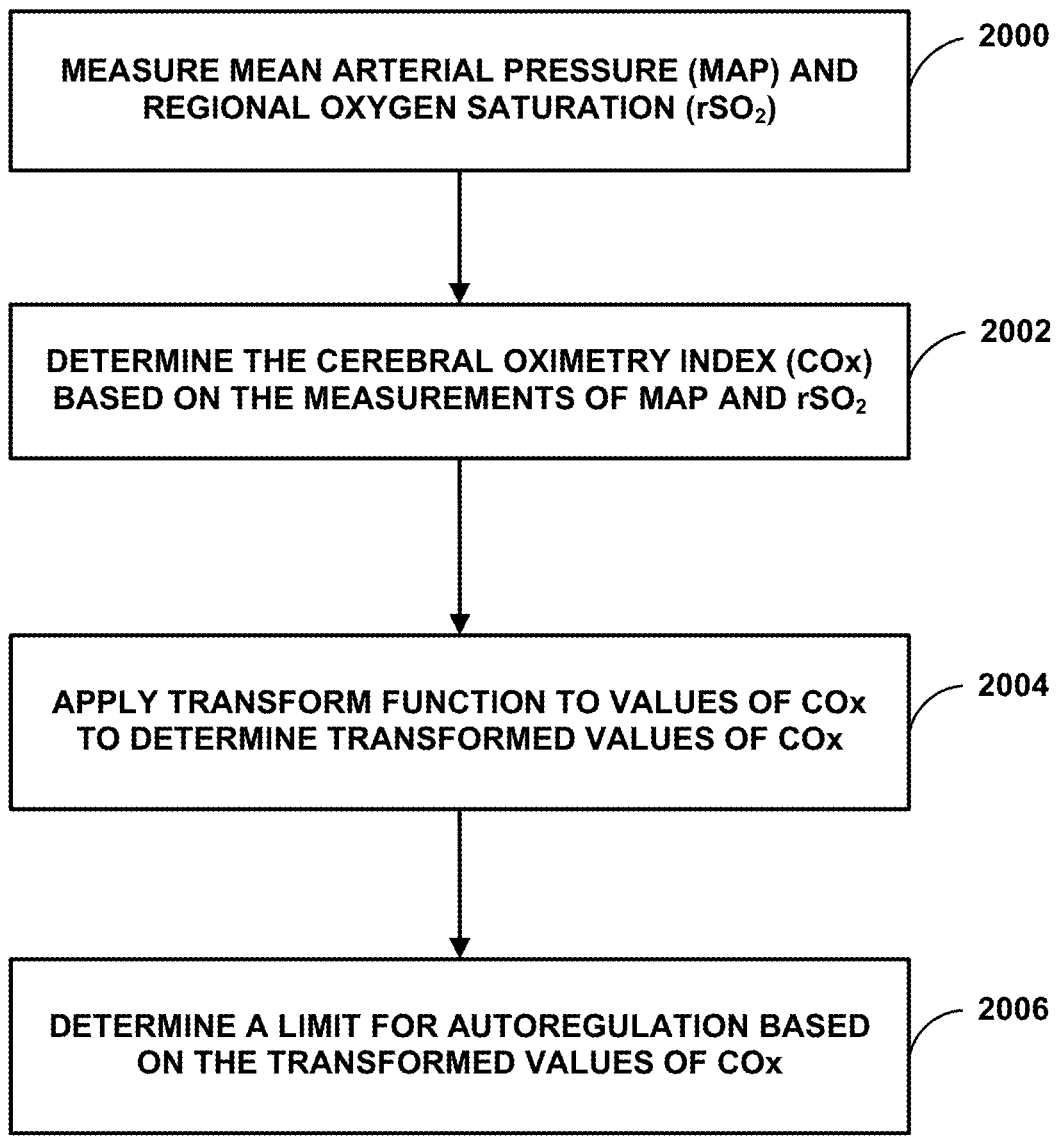
FIG. 20 is a flowchart illustrating example techniques for determining limit(s) of autoregulation by applying a transform function to measurements of COx, in accordance with some examples of this disclosure.

FIG. 20 is a flowchart illustrating example techniques for determining the LLA and/or the ULA by applying a transform function to measurements of COx, in accordance with some examples of this disclosure. In the example of FIG. 20, sensing devices 1730 and 1732 measure MAP and $rSO_2$ (2000), respectively, for a patient for a time duration, such as three hundred seconds. In the example of FIG. 20, processing circuitry 1710 determines value(s) of COx based on the measurements of MAP and $rSO_2$ (2002). In the example of FIG. 20, processing circuitry 1710 applies a transform function to the determined values of COx to determine transformed value(s) of COx (2004). In some examples, the transform function may include a linear piecewise function, as depicted in FIG. 13 or a continuous function as shown in FIG. 16. The transform function may accentuate the difference in COx near the LLA and/or the ULA. In the example of FIG. 20, processing circuitry 1710 determines the LLA and/or the ULA based on the values of COx (2006).

In some examples, processing circuitry 1710 is configured to determine a trendline function based on the measurements of MAP and $rSO_2$. Processing circuitry 1710 then applies a first transform function to values of $rSO_2$ based on the trendline function to determine transformed values of $rSO_2$. Processing circuitry 1710 determines untransformed COx values based on the measurements of MAP and the transformed values of $rSO_2$. Processing circuitry 1710 can then apply a second transform function to the untransformed COx values to determine transformed COx values. Processing circuitry 1710 can determine a limit of autoregulation based on the transformed COx values. Thus, processing circuitry 1710 can use a combination of the techniques shown in FIGS. 18 and 20 to determine a limit of autoregulation.

Figure 21:
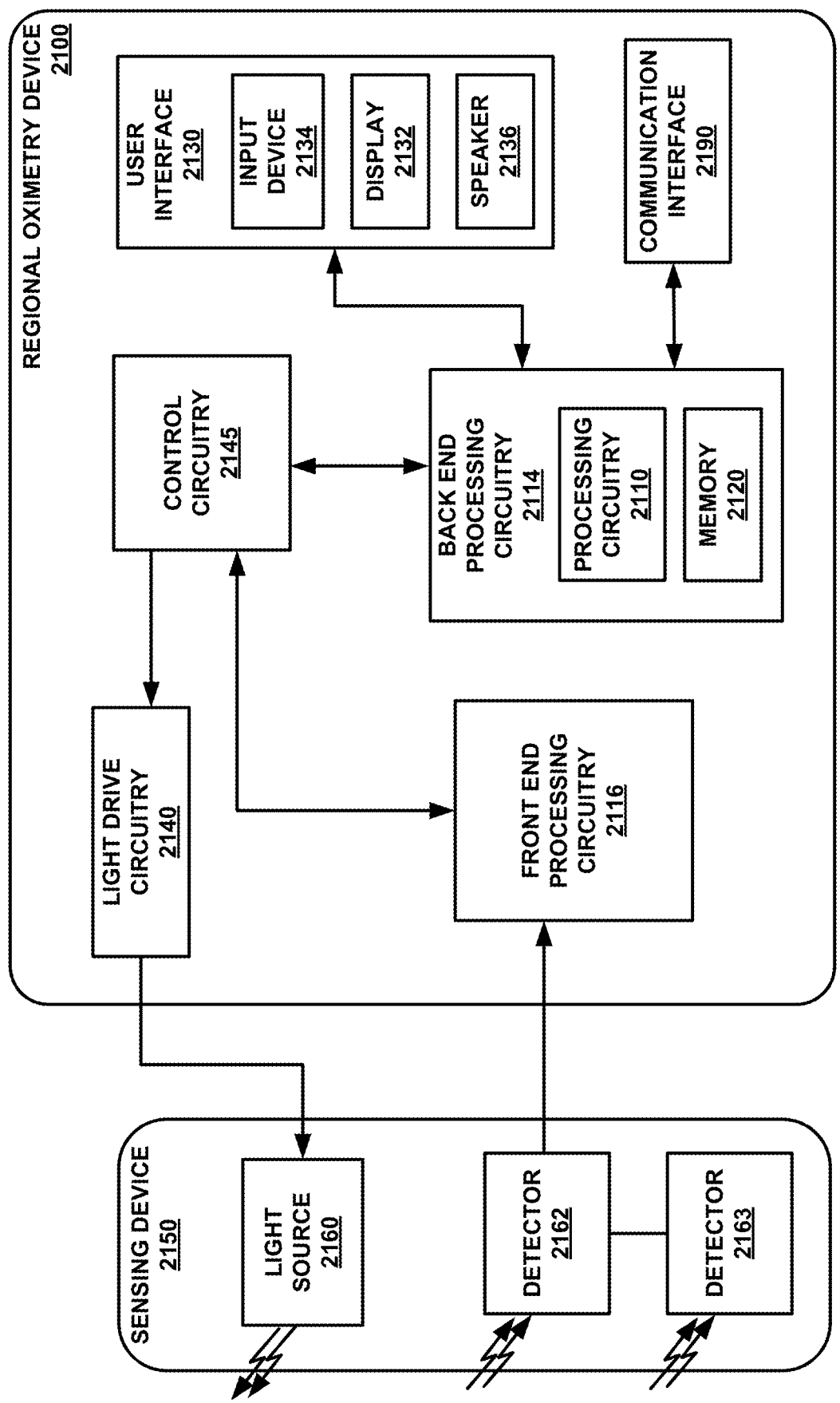
FIG. 21 is a conceptual block diagram illustrating an example regional oximetry device for monitoring the autoregulation status of a patient.

FIG. 21 is a conceptual block diagram illustrating an example regional oximetry 2100 device for monitoring the autoregulation status of a patient. In the example shown in FIG. 21, regional oximetry device 2100 is coupled to sensing device 2150 and may be collectively referred to as a regional oximetry system, which each generate and process physiological signals of a subject. In some examples, sensing device 2150 and regional oximetry device 2100 may be part of an oximeter. As shown in FIG. 21, regional oximetry device 2100 includes back-end processing circuitry 2114, user interface 2130, light drive circuitry 2140, front-end processing circuitry 2116, control circuitry 2145, and communication interface 2190. Regional oximetry device 2100 may be communicatively coupled to sensing device 2150. Regional oximetry device 2100 is an example of regional oximetry device 1700 shown in FIG. 17. In some examples, regional oximetry device 2100 may also include a blood pressure sensor and/or a blood volume sensor (e.g., sensing device 1732 shown in FIG. 17).

In the example shown in FIG. 21, sensing device 2150 includes light source 2160, detector 2162, and detector 2163. In some examples, sensing device 2150 may include more than two detectors. Light source 2160 may be configured to emit photonic signals having two or more wavelengths of light (e.g., red and infrared (IR)) into a subject's tissue. For example, light source 2160 may include a red light emitting light source and an IR light emitting light source, (e.g., red and IR light emitting diodes (LEDs)), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 2160 may include any number of light sources with any suitable characteristics. In examples in which an array of sensors is used in place of sensing device 2150, each sensing device may be configured to emit a single wavelength. For example, a first sensing device may emit only a red light while a second sensing device may emit only an IR light. In some examples, light source 2160 may be configured to emit two or more wavelengths of near-infrared light (e.g., wavelengths between 600 nm and 1000 nm) into a subject's tissue. In some examples, light source 2160 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 2162 and 2163 may be chosen to be specifically sensitive to the chosen targeted energy spectrum of light source 2160.

In some examples, detectors 2162 and 2163 may be configured to detect the intensity of multiple wavelengths of near-infrared light. In some examples, detectors 2162 and 2163 may be configured to detect the intensity of light at the red and IR wavelengths. In some examples, an array of detectors may be used and each detector in the array may be configured to detect an intensity of a single wavelength. In operation, light may enter detector 2162 after passing through the subject's tissue, including skin, bone, and other shallow tissue (e.g., non-cerebral tissue and shallow cerebral tissue). Light may enter detector 2163 after passing through the subject's tissue, including skin, bone, other shallow tissue (e.g., non-cerebral tissue and shallow cerebral tissue), and deep tissue (e.g., deep cerebral tissue). Detectors 2162 and 2163 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 2162 and 2163.

After converting the received light to an electrical signal, detectors 2162 and 2163 may send the detection signals to regional oximetry device 2100, where the detection signals may be processed and physiological parameters may be determined (e.g., based on the absorption of the red and IR wavelengths in the subject's tissue at both detectors). In some examples, one or more of the detection signals may be preprocessed by sensing device 2150 before being transmitted to regional oximetry device 2100. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 2145 may be coupled to light drive circuitry 2140, front-end processing circuitry 2116, and back-end processing circuitry 2114, and may be configured to control the operation of these components. In some examples, control circuitry 2145 may be configured to provide timing control signals to coordinate their operation. For example, light drive circuitry 2140 may generate one or more light drive signals, which may be used to turn on and off light source 2160, based on the timing control signals provided by control circuitry 2145. Front-end processing circuitry 2116 may use the timing control signals to operate synchronously with light drive circuitry 2140. For example, front-end processing circuitry 2116 may synchronize the operation of an analog-to-digital converter and a demultiplexer with the light drive signal based on the timing control signals. In addition, the back-end processing circuitry 2114 may use the timing control signals to coordinate its operation with front-end processing circuitry 2116.

Light drive circuitry 2140, as discussed above, may be configured to generate a light drive signal that is provided to light source 2160 of sensing device 2150. The light drive signal may, for example, control the intensity of light source 2160 and the timing of when light source 2160 is turned on and off. In some examples, light drive circuitry 2140 provides one or more light drive signals to light source 2160. Where light source 2160 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 2116 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 2116, which may convert the conditioned analog signals into digital signals. Front-end processing circuitry 2116 may operate on the analog or digital form of the detector signals to separate out different components of the signals. Front-end processing circuitry 2116 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 2116 may decrease the number of samples in the digital detector signals. In some examples, front-end processing circuitry 2116 may also remove dark or ambient contributions to the received signal.

Back-end processing circuitry 2114 may include processing circuitry 2110 and memory 2120. Processing circuitry 2110 may include an assembly of analog or digital electronic components and may be configured to execute software, which may include an operating system and one or more applications, as part of performing the functions described herein with respect to, e.g., processing circuitry 110. Processing circuitry 2110 may receive and further process physiological signals received from front-end processing circuitry 2116. For example, processing circuitry 2110 may determine one or more physiological parameter values based on the received physiological signals. For example, processing circuitry 2110 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 2110 may perform any suitable signal processing of a signal, such as any suitable band-pass filtering, adaptive filtering, closed-loop filtering, any other suitable filtering, and/or any combination thereof. Processing circuitry 2110 may also receive input signals from additional sources not shown. For example, processing circuitry 2110 may receive an input signal containing information about treatments provided to the subject from user interface 2130. Additional input signals may be used by processing circuitry 2110 in any of the determinations or operations it performs in accordance with back-end processing circuitry 2114 or regional oximetry device 2100.

Processing circuitry 2110 is an example of processing circuitry 110 and is configured to perform the techniques of this disclosure. For example, processing circuitry 2110 is configured to receive signals indicative of physiological parameters. Processing circuitry 2110 is also configured to determine values of physiological parameters based on the signals and determine correlation coefficient values based on the values of the physiological parameters. In some examples, processing circuitry 2110 may be configured to transform values of one of the physiological parameters and use the transformed values to determine correlation coefficient values. Processing circuitry 2110 is configured to then determine a limit of autoregulation based on the correlation coefficient values. Alternatively or additionally, processing circuitry 2110 may be configured to determine correlation coefficient values based on the untransformed values of the two physiological parameters and then determine transformed values of the correlation coefficients.

Memory 2120 may include any suitable computer-readable media capable of storing information that can be interpreted by processing circuitry 2110. In some examples, memory 2120 may store correlation coefficient values, threshold rates, threshold values, window lengths, reference absorption curves, reference sets, determined values, such as blood oxygen saturation, pulse rate, blood pressure, fiducial point locations or characteristics, initialization parameters, any other determined values, or any combination thereof, in a memory device for later retrieval. Back-end processing circuitry 2114 may be communicatively coupled with user interface 2130 and communication interface 2190.

User interface 2130 may include input device 2134, display 2132, and speaker 2136. User interface 2130 is an example of user interface 1714 shown in FIG. 17, and display 2132 is an example of display 1715 shown in FIG. 17. User interface 2130 may include, for example, any suitable device such as one or more medical devices (e.g., a medical monitor that displays various physiological parameters, a medical alarm, or any other suitable medical device that either displays physiological parameters or uses the output of back-end processing 2114 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 2134 may include any type of user input device such as a keyboard, a mouse, a touch screen, buttons, switches, a microphone, a joy stick, a touch pad, or any other suitable input device or combination of input devices. In other examples, input device 2134 may be a pressure-sensitive or presence-sensitive display that is included as part of display 2132. Input device 2134 may also receive inputs to select a model number of sensing device 2150, blood pressure sensor 2150 (FIG. 21), or blood pressure processing equipment. In some examples, processing circuitry 2110 may determine a threshold rate and/or a length of a window of time based on user input received from input device 2134.

Figure 22:
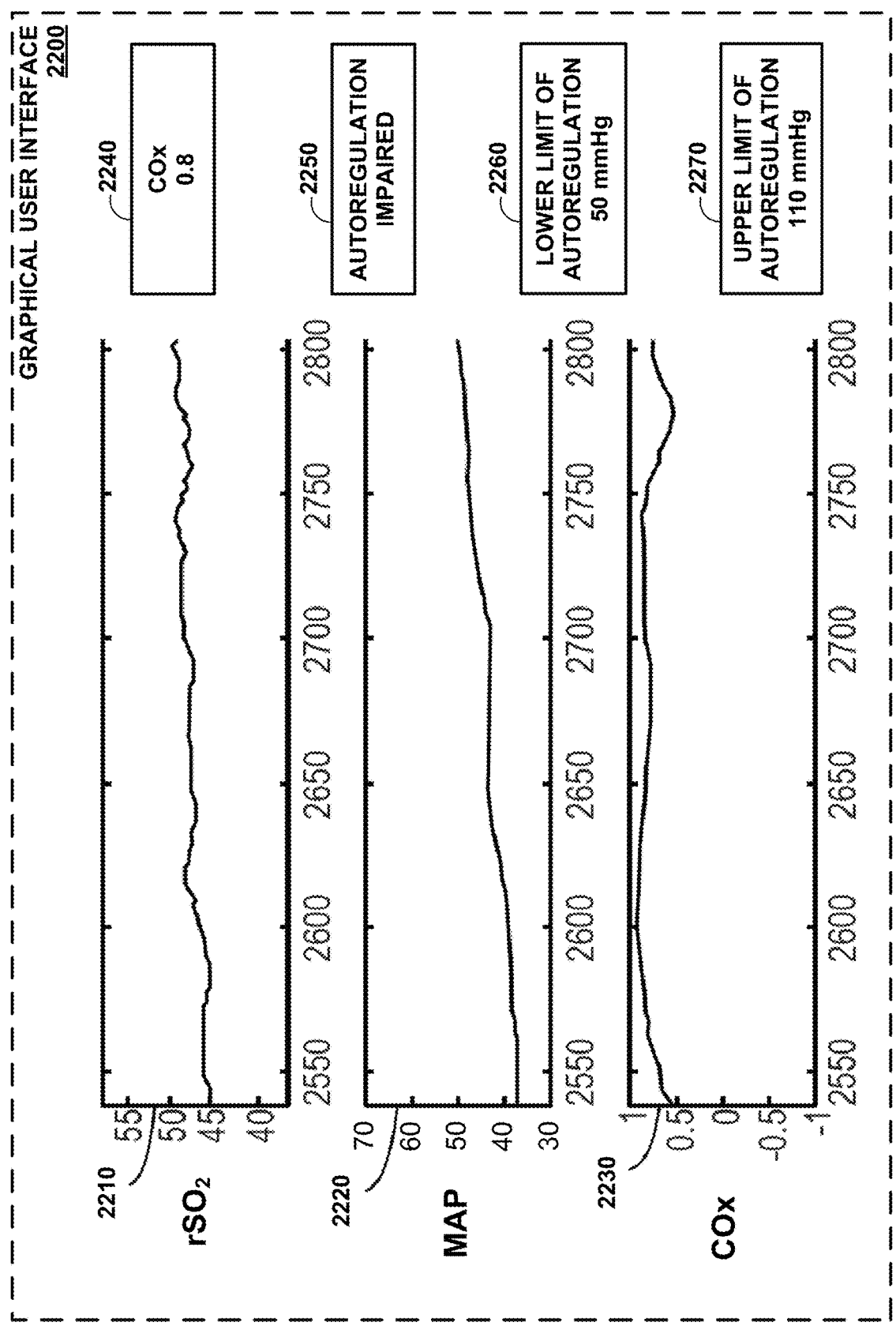
FIG. 22 illustrates an example graphical user interface including autoregulation information presented on a display.

In some examples, the subject may be a medical patient and display 2132 may exhibit a list of values which may generally apply to the subject, such as, for example, an oxygen saturation signal indicator, a blood pressure signal indicator, a COx signal indicator, a COx value indicator, and/or an autoregulation status indicator. Display 2132 may also be configured to present additional physiological parameter information. Graphical user interface 2200 shown in FIG. 22 is an example of an interface that can be presented via display 2132 of FIG. 21. Additionally, display 2132 may present, for example, one or more estimates of a subject's regional oxygen saturation generated by regional oximetry device 2100 (referred to as an "rSO$_2$" measurement). Display 2132 may also present indications of the upper and lower limits of autoregulation. Speaker 2136 within user interface 2130 may provide an audible sound that may be used in various examples, such as for example, sounding an audible alarm in the event that a patient's physiological parameters are not within a predefined normal range.

Communication interface 2190 may enable regional oximetry device 2100 to exchange information with external devices. Communication interface 2190 may include any suitable hardware, software, or both, which may allow regional oximetry device 2100 to communicate with electronic circuitry, a device, a network, a server or other workstations, a display, or any combination thereof. For example, regional oximetry device 2100 may receive MAP values and/or oxygen saturation values from an external device via communication interface 2190.

The components of regional oximetry device 2100 that are shown and described as separate components are shown and described as such for illustrative purposes only. In some examples the functionality of some of the components may be combined in a single component. For example, the functionality of front-end processing circuitry 2116 and back-end processing circuitry 2114 may be combined in a single processor system. Additionally, in some examples the functionality of some of the components of regional oximetry device 2100 shown and described herein may be divided over multiple components. For example, some or all of the functionality of control circuitry 2145 may be performed in front-end processing circuitry 2116, in back-end processing circuitry 2114, or both. In other examples, the functionality of one or more of the components may be performed in a different order or may not be required. In some examples, all of the components of regional oximetry device 2100 can be realized in processor circuitry.

FIG. 22 illustrates an example graphical user interface 2200 including autoregulation information presented on a display. FIG. 22 is an example of a presentation by processing circuitry 1710 on display 1715 shown in FIG. 17 or by processing circuitry 210 on display 232 shown in FIG. 2. Graphical user interface 2200 may be configured to display various information related to blood pressure, oxygen saturation, the COx index, limits of autoregulation, and/or autoregulation status. As shown, graphical user interface 2200 may include oxygen saturation signal indicator 2210, blood pressure signal indicator 2220, and COx signal indicator 2230. Graphical user interface 2200 may include COx value indicator 2240, autoregulation status indicator 2250, and limit of autoregulation indicators 2260 and 2270.

Blood pressure signal indicator 2220 may present a set of MAP values determined by processing circuitry 1710 of regional oximetry device 1700. In some examples, blood pressure signal indicator 2220 may present MAP values as discrete points over time or in a table. Blood pressure signal indicator 2220 may also present MAP values as a moving average or waveform of discrete points. Blood pressure signal indicator 2220 may present MAP values as a single value (e.g., a number) representing a current MAP value. Oxygen saturation signal indicator 2210 and COx signal indicator 2230 may also present rSO$_2$ values and COx values, respectively, as discrete points, in a table, as a moving average, as a waveform, and/or as a single value. In some examples, processing circuitry 1710 can present transformed rSO$_2$ values in indicator 2210 and/or transformed MAP values in indicator 2220.

COx signal indicator 2230 may present a set of correlation coefficient values determined by processing circuitry 1710. Processing circuitry 1710 may determine the correlation coefficient values as a function of the oxygen saturation values presented in oxygen saturation signal indicator 2210 and the MAP values presented in blood pressure signal indicator 2220. In some examples, a COx value at or near one indicates the autoregulation status of a patient is impaired, as shown in autoregulation status indicator 2250. In some examples, processing circuitry 1710 can present transformed COx values in indicator 2230.

Processing circuitry 1710 may determine a set of correlation coefficient values and associated values of a first physiological parameter using the values presented in indicators 2210, 2220, and/or 2230. Processing circuitry 1710 may determine a particular time period in indicators 2210 or 2220 during which a value of $rSO_2$ changes rapidly, a value of MAP changes rapidly, or a product of $rSO_2$ and MAP changes rapidly. Processing circuitry 1710 may be configured to select a COx value associated with the particular time period from the COx values shown in indicator 2230. Processing circuitry 1710 then determines an updated value for the selected COx value in response to determining that a value of $rSO_2$ changes rapidly, a value of MAP changes rapidly, or a product of $rSO_2$ and MAP changes rapidly.

Processing circuitry 1710 may be configured to determine an estimate of a limit of autoregulation based on (transformed or untransformed) correlation coefficient values across a time window for data collection. For example, the length of the time window may be 300 seconds, 250 seconds, 200 seconds, 150 seconds, 100 seconds, 50 seconds, and/or any other suitable length of time.

COx value indicator 2240 shows a COx value of 0.8, which may result in a determination by processing circuitry 1710 that the autoregulation status of the patient is impaired. Processing circuitry 1710 may be configured to present, as the COx value in COx value indicator 2240, the most recently determined COx value or a moving average of recently determined COx values. To determine the autoregulation status of a patient for presentation in autoregulation status indicator 2250, processing circuitry 1710 may determine whether the most recent MAP value shown in blood pressure signal indicator 2220 is between the limits of autoregulation presented in limit of autoregulation indicators 2260 and 2270.

Processing circuitry 1710 may present limit of autoregulation indicators 2260 and/or 2270 in terms of blood pressure, for example, mmHg. Processing circuitry 1710 can determine the limits of cerebral autoregulation (LLA and ULA) for presentation in indicators 2260 and 2270 based on a relationship between the blood pressure of a patient and another physiological parameter of the patient. For example, indicator 2250 and/or indicator 2260 may be highlighted when the LLA has been exceeded or indicator 2260 may be highlighted when the ULA has been exceeded. In other examples, a single indicator may present the type of limit that has been exceed by the MAP value. If the LLA or ULA change, processing circuitry 1710 may control user interface 2200 to change the value of the LLA or ULA in accordance with any change to that respective value.

Processing circuitry 1710 may determine an estimate of a lower limit of autoregulation presented in indicator 2260 and/or an estimate of an upper limit of autoregulation presented in indicator 2270. Processing circuitry 1710 may determine the estimates based on a set of correlation coefficient values including one or more updated values. Processing circuitry 1710 may be configured to generate a notification in response to determining that the MAP value is less than or equal to the estimate of the lower limit of autoregulation. Processing circuitry 1710 may output the notification in autoregulation status indicator 2250 as text, color, blinking, and/or any other suitable visible or audible manner.

Where processing circuitry 1710 is described herein as determining that a value is less than or equal to another value, this description may also include processing circuitry 1710 determining that a value is only less than the other value. Similarly, where processing circuitry 1710 is described herein as determining that a value is less than another value, this description may also include processing circuitry 1710 determining that a value is less than or equal to the other value. The same properties may also apply to the terms "greater than" and "greater than or equal to."

Various examples of the disclosure have been described. Any combination of the described systems, operations, or functions is contemplated. These and other examples are within the scope of the following claims.

What is claimed is:

1. A device comprising:
a display; and
processing circuitry configured to:
 receive a first signal indicative of a first physiological parameter of a patient;
 receive a second signal indicative of a blood pressure of the patient;
 determine a trendline function based on a best fit of values of the first physiological parameter sensed at the patient during a time period from a first time to a second time and blood pressure values sensed at the patient during the time period;
 determine transformed values of the first physiological parameter based on a slope of the trendline function and the values of the first physiological parameter sensed at the patient during the time period;
 determine correlation coefficient values indicating a correlation between the transformed values of the first physiological parameter and the blood pressure values;
 determine a lower limit of autoregulation of the patient based on the correlation coefficient values;
 determine that a blood pressure of the patient sensed at a third time is less than the lower limit of autoregulation; and
 output, for display via the display, an indication that the blood pressure of the patient sensed at the third time is less than the lower limit of autoregulation.

2. The device of claim 1, wherein the processing circuitry is configured to:
determine an upper limit of autoregulation based on the correlation coefficient values;
determine that a blood pressure of the patient sensed at a fourth time is less than the upper limit of autoregulation; and
output, for display via the display, an indication that the blood pressure of the patient sensed at the fourth time is less than the upper limit of autoregulation.

3. The device of claim 1,
wherein the first physiological parameter comprises an oxygen saturation of the patient,
wherein the processing circuitry is configured to determine the trendline function at least in part by determining the trendline function based on a best fit of values of the measurements of oxygen saturation in the blood of the patient sensed at the patient during the time period and the blood pressure of the patient sensed during the time period,
wherein the processing circuitry is configured to determine the transformed values of the first physiological parameter at least in part by determining transformed values of oxygen saturation in the blood of the patient, and wherein the processing circuitry is configured to determine the correlation coefficient values at least in part by determining correlation coefficient values for the transformed values of oxygen saturation in the blood of the patient and the blood pressure of the patient.

4. The device of claim 1, wherein the processing circuitry is configured to determine the slope of the trendline function at least in part by determining a best fit for the values of the first physiological parameter sensed at the patient during the time period and blood pressure values sensed at the patient during the time period.

5. The device of claim 1, wherein the processing circuitry is configured to determine the transformed values of the first physiological parameter at least in part by determining transformed values of the first physiological parameter based on a difference between each value of the first physiological parameter sensed at the patient during the time period and a respective expected trendline value of the first physiological parameter.

6. The device of claim 1, wherein the processing circuitry is configured to determine the correlation coefficient values at least in part by:
    binning each transformed value of the first physiological parameter based on a respective blood pressure value; and
    determining an average correlation coefficient value for each bin of a plurality of bins.

7. The device of claim 1,
    wherein the processing circuitry is further configured to determine an initial slope of a trendline function based on historical data, and
    wherein the processing circuitry is configured to determine the slope of the trendline function at least in part by reducing an effect of the initial trendline function as the processing circuitry determines values of the first physiological parameter.

8. The device of claim 1,
    wherein the processing circuitry is further configured to determine that a total number of data points exceeds a threshold number, and
    wherein the processing circuitry is configured to determine the slope of the trendline function and determine the transformed values of the first physiological parameter in response to determining that the total number of data points exceeds the threshold number.

9. A method comprising:
    receiving, by processing circuitry of a device and from sensing circuitry, a first signal indicative of a first physiological parameter of a patient;
    receiving, by the processing circuitry and from the sensing circuitry, a second signal indicative of a blood pressure of the patient;
    determining, by the processing circuitry, a trendline function based on a best fit of values of the first physiological parameter sensed at the patient during a time period from a first time to a second time and blood pressure values sensed at the patient during the time period;
    determining, by the processing circuitry, transformed values of the first physiological parameter based on a slope of the trendline function and the values of the first physiological parameter sensed at the patient during the time period;
    determining, by the processing circuitry, correlation coefficient values indicating a correlation between the transformed values of the first physiological parameter and the blood pressure values;
    determining, by the processing circuitry, that a blood pressure of the patient sensed at a third time is less than the lower limit of autoregulation; and
    outputting, by the processing circuitry, an indication that the blood pressure of the patient sensed at the third time is less than the lower limit of autoregulation.

10. The method of claim 9,
    wherein receiving the first signal comprises receiving an oxygen saturation signal of the patient,
    wherein determining the trendline function comprises determining the trendline function based on a best fit of values of the measurements of oxygen saturation in the blood of the patient sensed at the patient during the time period and the blood pressure of the patient sensed during the time period,
    wherein determining the transformed values of the first physiological parameter comprises determining transformed values of oxygen saturation in the blood of the patient, and
    wherein determining the correlation coefficient values comprises determining correlation coefficient values for the transformed values of oxygen saturation in the blood of the patient and the blood pressure of the patient.

11. The method of claim 9, wherein determining the trendline function comprises determining the best fit for the values of the first physiological parameter sensed at the patient during the time period and the blood pressure values sensed at the patient during the time period.

12. The method of claim 9, wherein determining the transformed values of the first physiological parameter comprises determining transformed values of the first physiological parameter based on a difference between each value of the first physiological parameter sensed at the patient during the time period and a respective expected trendline value of the first physiological parameter.

13. The method of claim 9, further comprising determining an initial slope of a trendline function based on historical data,
    wherein determining the slope of the trendline function comprises reducing an effect of the initial trendline function while determining values of the first physiological parameter.

14. The method of claim 9, further comprising determining that a total number of data points exceeds a threshold number,
    wherein determining the slope of the trendline function and determining the transformed values of the first physiological parameter are in response to determining that the total number of data points exceeds the threshold number.

15. The method of claim 9, further comprising: determining an upper limit of autoregulation based on the correlation coefficient values; determining that a blood pressure of the patient sensed at a fourth time is less than the upper limit of autoregulation; and outputting, for display via a display, an indication that the blood pressure of the patient sensed at the fourth time is less than the upper limit of autoregulation.

* * * * *